US010160810B2

(12) United States Patent
Moretta et al.

(10) Patent No.: US 10,160,810 B2
(45) Date of Patent: Dec. 25, 2018

(54) MONOCLONAL ANTIBODIES AGAINST NKG2A

(71) Applicants: INNATE PHARMA, S.A., Marseilles (FR); UNIVERSITY OF GENOVA, Genoa (IT)

(72) Inventors: Alessandro Moretta, Genoa (IT); Emanuela Marcenaro, Genova-Pegli (IT); Francois Romagne, Marseilles (FR); Pascale Andre, Marseilles (FR)

(73) Assignees: INNATE PHARMA, S.A., Marseilles (FR); UNIVERSITY OF GENOVA, Genoa (IT)

(*) Notice: Subject to any disclaimer, the term of this patent is extended or adjusted under 35 U.S.C. 154(b) by 494 days.

(21) Appl. No.: 14/594,353

(22) Filed: Jan. 12, 2015

(65) Prior Publication Data

US 2015/0125464 A1 May 7, 2015

Related U.S. Application Data

(62) Division of application No. 11/720,553, filed as application No. PCT/IB2005/004013 on Dec. 27, 2005, now Pat. No. 8,993,319.

(60) Provisional application No. 60/639,465, filed on Dec. 28, 2004, provisional application No. 60/639,832, filed on Dec. 28, 2004.

(51) Int. Cl.
*A61K 39/395* (2006.01)
*C07K 16/28* (2006.01)
*A61K 45/06* (2006.01)
*G01N 33/569* (2006.01)
*A61K 39/00* (2006.01)

(52) U.S. Cl.
CPC ...... *C07K 16/2896* (2013.01); *A61K 39/3955* (2013.01); *A61K 45/06* (2013.01); *C07K 16/2851* (2013.01); *G01N 33/56966* (2013.01); *A61K 2039/505* (2013.01); *A61K 2039/572* (2013.01); *C07K 2317/21* (2013.01); *C07K 2317/76* (2013.01); *G01N 2333/70596* (2013.01); *G01N 2500/04* (2013.01)

(58) Field of Classification Search
None
See application file for complete search history.

(56) References Cited

U.S. PATENT DOCUMENTS

| 5,489,525 | A | 2/1996 | Pastan |
| 5,859,205 | A | 1/1999 | Adair et al. |
| 5,876,950 | A | 3/1999 | Siadak et al. |
| 5,994,524 | A | 11/1999 | Matsushima et al. |
| 8,206,709 | B2 | 6/2012 | Spee et al. |
| 8,796,427 | B2 | 8/2014 | Spee et al. |
| 9,512,228 | B2 | 12/2016 | Soederstroem et al. |
| 2003/0095965 | A1 | 5/2003 | Van Beneden et al. |
| 2003/0171280 | A1 | 9/2003 | Soderstrom |
| 2005/0037002 | A1 | 2/2005 | Velardi et al. |
| 2009/0208416 | A1 | 8/2009 | Moretta et al. |
| 2011/0052606 | A1 | 3/2011 | Spee et al. |
| 2011/0229486 | A1 | 9/2011 | Moretta et al. |
| 2014/0161802 | A1 | 6/2014 | Soederstroem et al. |
| 2017/0073417 | A1 | 3/2017 | Soederstroem et al. |

FOREIGN PATENT DOCUMENTS

| CN | 1747969 | 3/2006 |
| CN | 101107269 | 10/2012 |
| EP | 1 036 327 | 9/2000 |
| JP | 3112485 | 5/1991 |
| JP | 3112486 | 5/1991 |
| JP | 3112487 | 5/1991 |
| JP | 2004-528824 | 9/2004 |
| JP | 3112484 | 8/2005 |
| WO | WO 1999/28748 | 6/1999 |
| WO | WO 01/71005 | 9/2001 |
| WO | WO 02/05122 | 1/2002 |
| WO | WO 02/50122 | 6/2002 |
| WO | WO 03/008449 | 1/2003 |
| WO | WO 03/095965 | 11/2003 |
| WO | WO 2004/003019 | 1/2004 |
| WO | WO 2004/056312 | 7/2004 |
| WO | WO2005/009465 | 2/2005 |
| WO | WO2005/105849 | 11/2005 |
| WO | WO 2006/070286 | 7/2006 |
| WO | WO 2007/042573 | 4/2007 |
| WO | WO 2008/009545 | 1/2008 |
| WO | WO 2009/092805 | 7/2009 |
| WO | WO 2011/104381 | 9/2011 |
| WO | WO 2012/172102 | 12/2012 |

OTHER PUBLICATIONS

Flodstrom et al., 2002, Scan. J. Immunol. vol. 55: 432-441.*
Khan et al., 2009, Nat. Rev. Rheum. vol. 5: 566-571.*
Isaksson et al., 2012, Eur. J. Immunol. vol. 42: 2555-2563.*
Benichou et al., 2011, Curr. Opin. Organ Transplant, vol. 16: 47-53.*
French et al., 2004, Arhtritis Res Ther vol. 6: 8-14.*
Jadidi-Niaragh et al., 2012, Scan. J. Immunol. vol. 76: 451-456.*
Hall et al., 2013, Nature, vol. 6: 1016-1026.*
Shum et al., 2002, J. Immunol. vol. 168: 240-252.*
Braud et al., 2003, Trends in Immunology, vol. 24: 162-164.*
Saverino et al., 1999, J. Immunol. vol. 162: 651-658.*
Jinushi et al., Nov. 2004, J. Immunol. vol. 173: 6072-6081.*

(Continued)

*Primary Examiner* — Amy E Juedes
(74) *Attorney, Agent, or Firm* — Saliwanchik, Lloyd & Eisenschenk

(57) ABSTRACT

The present invention relates to methods of treating immune disorders, particularly autoimmune or inflammatory disorders, and methods of producing antibodies and other compounds for use in therapeutic strategies for treating such disorders. Generally, the present methods involve the use of antibodies or other compounds that prevent the stimulation of NKG2A receptors on NK cells, leading to the lysis of dendritic cells that contribute to the pathology of the disorders.

5 Claims, 5 Drawing Sheets
Specification includes a Sequence Listing.

(56) References Cited

OTHER PUBLICATIONS

Leavenworth, J. et al. "Analysis of the cellular mechanism underlying inhibition of EAE after treatment with anti-NKG2A F(ab')$_2$," *PNAS*, 2010, pp. 1-6.

Durand, M. et al. "Monocytes From Patients With Osteoarthritis Display Increased Osteoclastogenesis and Bone Resorption," *Arthritis & Rheumatism*, Jan. 2013, pp. 148-158, vol. 65, No. 1.

Isaacs, J.D. et al. "Therapeutic agents for patients with rheumatoid arthritis and an inadequate response to tumour necrosis factor-α antagonists," *Expert Opinion on Biological Therapy*, 2009, pp. 1463-1475, vol. 9, No. 12.

Liao, K.P. et al. "Clinical predictors of erosion-free status in rheumatoid arthritis: a prospective cohort study," *Rheumatology Advance Access*, Mar. 29, 2011, pp. 1-7.

Saleem, B. et al. "Patients with RA in remission on TNF blockers: when and in whom can TNF blocker therapy be stopped?," *Annals of the Rheumatic Diseases*, 2010, pp. 1636-1642, vol. 69.

Zwerina, J. et al. "Single and Combined Inhibition of Tumor Necrosis Factor, Interleukin-1, and RANKL Pathways in Tumor Necrosis Factor-Induced Arthritis" *Arthritis and Rheumatism*, Jan. 2004, pp. 277-290, vol. 50, No. 1.

Roitt et al., *New methods of Immunoassay*, 1991, pp. 65-75.

D'Andrea, A. et al. "Regulation of T Cell Lymphokine Production by killer Cell Inhibitory Receptor Recognition of Self HLA Class I Alleles," *J. Exp. Med.*, Aug. 1996, pp. 789-794, vol. 184.

Pende, D. et al. "HLA-G recognition by human natural killer cells. Involvement of CD94 both as inhibitory and as activating receptor complex," *Eur. J. Immunol.*, 1997, pp. 1875-1880, vol. 27.

Perez-Villar, J. J. et al. "The CD94/NKG2-A Inhibitory Receptor Complex is Involved in Natural Killer Cell-Mediated Recognition of Cells Expressing HLA-G1," *The Journal of Immunology*, Mar. 14, 1997, vol. 158, pp. 5736-5743.

Presta, L.G. "Engineering of therapeutic antibodies to minimize immunogenicity and optimize function," *Advanced Drug Delivery Reviews*, 2006, pp. 640-656, vol. 58, No. 5-6.

Colman P. M., *Research in Immunology*, 1994, vol. 145, pp. 33-36.

Padlan, E. "Anatomy of the Antibody Molecule," *Molecular Immunology*, 1994, vol. 31, No. 3, pp. 169-217.

Portolano, S. et al. "Lack of Promiscuity in Autoantigen-Specific H and L Chain Combinations as Revealed by Human H and L 'Chain Roulette'," *The Journal of Immunology*, Feb. 1, 1993, vol. 150, No. 3, pp. 880-887.

Aramaki, T. et al. "A significantly impaired natural killer cell activity due to a low activity on a per-cell basis in rheumatoid arthritis" *Mod Rheumatol*, 2009, vol. 19, pp. 245-252.

Huss, R. S. et al. "Synovial Tissue—Infiltrating Natural Killer Cells in Osteoarthritis and Periprosthetic Inflammation" Dec. 2010, vol. 62, No. 12, pp. 3799-3805.

Schett, G. "Joint remodeling in inflammatory disease" *Ann Rheum Dis*, 2007, vol. 66, Suppl III, pp. iii42-iii44.

Dankbar, B. et al. "Hepatocyte Growth Factor Induction of Macrophage Chemoattractant Protein-1 and Osteophyte-Inducing Factors in Osteoarthritis" *Journal of Orthopaedic Research*, May 2007, vol. 25, pp. 569-577.

Lajeunesse, D. et al. "Osteoporosis and osteoarthritis: bone is the common battleground" *Medicographia*, 2010, vol. 32, No. 4, pp. 391-398.

Anonymous, "NK Cells Mini-Review" *Bio-Rad*, 2015, pp. 1-7.

Borrego, F. et al. "NK Cell CD94/NKG2A Inhibitory Receptors are Internalized and Recycle Independently of Inhibitory Signaling Processes" *The Journal of Immunology*, 2002, pp. 6102-6111, vol. 169.

Priggeon, C. et al. "Natural killer cells in the synovial fluid of rheumatoid arthritis patients exhibit a CD56bright,CD94bright,CD158negative phenotype," *Rheumatology*, 2003, vol. 42, No. 7, pp. 870-878.

Bagot, M. et al. "Functional Inhibitory Receptors Expressed by a Cutaneous T Cell Lymphoma-Specific Cytolytic Clonal T Cell Population" *Journal of Investigative Dermatology*, Dec. 2000, pp. 994-999, vol. 115, No. 6.

Bagot, M. et al. "CD4$^+$ Cutaneous T-cell Lymphoma Cells Express the p140—Killer Cell Immunoglobulin-like Receptor" *Blood*, Mar. 1, 2001, pp. 1388-1391, vol. 97, No. 5.

Biassoni, R. et al. "Molecular and Functional Characterization of NKG2D, NKp80, and NKG2C Triggering NK Cell Receptors in Rhesus and Cynomolgus Macaques: Monitoring of NK Cell Function during Simian HIV Infection" *Journal of Immunology*, 2005, pp. 5695-5705, vol. 174.

Carretero, M. et al. "The CD94 and NKG2-A C-type Lectins Covalently Assemble to Form a Natural Killer Cell Inhibitory Receptor for HLA Class I Molecules" *European Journal of Immunology*, 1997, pp. 563-567, vol. 27.

Costa, P. et al. "Differential Disappearance of Inhibitory Natural Killer Cell Receptors during HAART and Possible Impairment of HIV-1-Specific CD8 Cytotoxic T Lymphocytes" *Aids*, 2001, pp. 965-974, vol. 15.

Haedicke, W. et al. "Expression of CD94/NKG2A and Killer Immunoglobulin-Like Receptors in NK Cells and a Subset of Extranodal Cytotoxic T-cell Lymphomas" *Blood*, Jun. 1, 2000, pp. 3628-3630, vol. 95, No. 11.

Kamarashev, J. et al. "Differential Expression of Cytotoxic Molecules and Killer Cell Inhibitory Receptors in CD8+ and CD56+ Cutaneous Lymphomas" *American Journal of Pathology*, May 2001, pp. 1593-1598, vol. 158, No. 5.

Le Bouteiller, P. et al. "Engagement of CD160 Receptor by HLA-C is a Triggering Mechanism used by Circulating Natural Killer (NK) Cells to Mediate Cytotoxicity" *Proceedings of the National Academy of Sciences of the USA*, Dec. 24, 2002, pp. 16963-16968, vol. 99, No. 26.

Mavilio, D. et al. "Identification of NKG2A and NKp80 as Specific Natural Killer Cell Markers in Rhesus and Pigtailed Monkeys" *Blood*, Sep. 1, 2005, pp. 1718-1725, vol. 106, No. 5.

Mingari, M.C. et al. "HLA Class I-specific Inhibitory Receptors in Human T Lymphocytes: Interleukin 15-induced Expression of CD94/NKG2A in Superantigen- or Alloantigen-activated CD8$^+$ T Cells" *Proceedings of the National Academy of Sciences of the USA*, Feb. 1998, pp. 1172-1177, vol. 95.

Ponte, M. et al. "Inhibitory Receptors Sensing HLA-G1 Molecules in Pregnancy: Decidua-associated Natural Killer Cells Express LIR-1 and CD94/NKG2A and acquire p49, and HLA-G1-Specific Receptor" *Proceedings of the National Academy of Sciences of the USA*, May 1999, pp. 5674-5679, vol. 96.

Sivori, S. et al. "CD94 Functions as a Natural Killer Cell Inhibitory Receptor for Different HLA Class I Alleles: Identification of the Inhibitory Form of CD94 by the Use of Novel Monoclonal Antibodies" *European Journal of Immunology*, 1996, pp. 2487-2492, vol. 26.

Sivori, S. et al. "p46, a Novel Natural Killer Cell-specific Surface Molecule that Mediates Cell Activation" *Journal of Experimental Medicine*, Oct. 6, 1997, pp. 1129-1136, vol. 186, No. 7.

Vacca, P. et al. "Analysis of Natural Killer Cells Isolated from Human Decidua: Evidence that 2B4 (CD244) Functions as an Inhibitory Receptor and Blocks NK-cell Function" *Blood*, 2006, pp. 4078-4085, vol. 108, No. 13.

Vitale, M. et al. "The Leukocyte Ig-like Receptor (LIR)-1 for the Cytomegalovirous UL18 Protein Displays a Broad Specificity for Different HLA Class I Alleles: Analysis of LIR-1$^+$ NK Cell Clones" *International Immunology*, 1999, pp. 29-35, vol. 11, No. 1.

Voss, S.D. et al. "Participation of the CD94 Receptor Complex in Costimulation of Human Natural Killer Cells" *Journal of Immunology*, 1998, pp. 1618-1626, vol. 160.

Zimmer, J. et al. "Activity and Phenotype of Natural Killer Cells in Peptide Transporter (TAP)-deficient Patients (Type I Bare Lymphocyte Syndrome)" *Journal of Experimental Medicine*, Jan. 5, 1998, pp. 117-122, vol. 187, No. 1.

Castriconi, R. et al. "Shaping of adaptive immunity by innate interactions", *C.R. Biologies*, 2004, pp. 533-537, vol. 327.

(56) References Cited

OTHER PUBLICATIONS

Guma, M. et al. "Imprint of human cytomegalovirus infection on the NK cell receptor repertoire", *Blood*, Dec. 1, 2004, pp. 3664-3671, vol. 104, No. 12.

Gunturi, A. et al. "The Role of CD94/NKG2 in Innate and Adaptive Immunity", Immunologic Research, 2004, pp. 29-34, vol. 30, No. 1.

Jinushi, M. et al. "Negative Regulation of NK Cell Activities by Inhibitor Receptor CD94/NKG2A Leads to Altered NK Cell-Induced Modulation of Dendritic Cell Functions in Chronic Hepatitis C Virus Infection", *The Journal of Immunology*, 2004, pp. 6072-6081, vol. 173.

Llano, M. et al. "Differential effects of US2, US6 and US11 human cytomegalovirus proteins on HLA class Ia and HLA-E expression: impact on target susceptibility to NK cell subsets", *Eur. J. Immunol.*, 2003, pp. 2744-2754, vol. 33.

Riteau, B. et al. "HLA-G1 co-expression boosts the HLA class I-mediated HK lysis inhibition", *International Immunology*, 2001, pp. 193-201, vol. 13, No. 2.

Ward, J. et al. "HLA-C and HLA-E reduce antibody-dependent natural killer cell-mediated cytotoxicity of HIV-infected primary T cell blasts", *AIDS*, 2004, pp. 1769-1779, vol. 18.

Author Guide, *Blood*, pp. 1-15, Aug. 30, 2010.

Instructions to Authors, *European Journal of Immunology*, pp. 1-6.

Gavilondo, J. V. et al. "Antibody Engineering at the Millennium" *Biotechniques*, Jul. 2000, pp. 128-145, vol. 29, No. 1.

Moretta, A. et al. "Identification of Four Subsets of Human $CD3^-CD16^+$ Natural Killer (NK) Cells by the Expression of Clonally Distributed Functional Surface Molecules: Correlation between Subset Assignment of NK Clones and Ability to Mediate Specific Alloantigen Recognition" *J. Exp. Med.*, Dec. 1990, pp. 1589-1598, vol. 172.

Cleland, J. L. et al. "The Development of Stable Protein Formulations: A Close Look at Protein Aggregation, Deamidation, and Oxidation" *Critical Reviews in Therapeutic Drug Carrier Systems*, 1993, pp. 307-377, vol. 10, No. 4.

Wu, A. M. et al. "Multimerization of a chimeric anti-CD20 single-chain Fv-Fc fusion protein is mediated through variable domain exchange" *Protein Engineering*, 2001, pp. 1025-1033, vol. 14, No. 12.

Aldrich, C. J. et al. "Identification of a Tap-Dependent Leader Peptide Recognized by Alloreactive T Cells Specific for a Class Ib Antigen" *Cell*, Nov. 18, 1994, pp. 649-658, vol. 79.

Aramburu, J. et al. "A Novel Functional Cell Surface Dimer (Kp43) Expressed by Natural Killer Cells and T Cell Receptor-$\gamma/\delta^+$ T Lymphocytes" *The Journal of Immunology*, Apr. 15, 1990, pp. 3238-3247, vol. 144, No. 8.

Borrego, F. et al. "Recognition of Human Histocompatibility Leukocyte Antigen (HLA)-E Complexed with HLA Class I Signal Sequence-derived Peptides by CD94/NKG2 Confers Protection from Natural Killer Cell-mediated Lysis" *The Journal of Experimental Medicine*, Mar. 2, 1998, pp. 813-818, vol. 187, No. 5.

Borrego, F. et al. "The CD94/NKG2 Family of Receptors From Molecules and Cells to Clinical Relevance" *Immunologic Research*, 2006, pp. 263-277, vol. 35, No. 3.

Braud, V. M. et al. "TAP- and tapasin-dependent HLA-E surface expression correlates with the binding of an MHC class I leader peptide" *Current Biology*, 1997, pp. 1-10, vol. 8.

Braud, V. M. et al. "HLA-E binds to natural killer cell receptors CD94/NKG2A, B and C" *Nature*, Feb. 19, 1998, pp. 795-799, vol. 391.

Braud, V. et al. "The human major histocompatibility complex class Ib molecule HLA-E binds signal sequence-derived peptides with primary anchor residues at positions 2 and 9" *Eur. J. Immunol.*, 1997, pp. 1164-1169, vol. 27.

Brooks, A. G. et al. "Specific Recognition of HLA-E, But Not Classical, HLA Class I Molecules by Soluble CD94/NKG2A and NK Cells" *Journal of Immunology*, 1999, pp. 305-313, vol. 162.

Carter, P. et al. "Humanization of an anti-$p185^{HER2}$ antibody for human cancer therapy" *Proc. Natl. Acad. Sci. USA*, May 1992, pp. 4285-4289, vol. 89.

Casset, F. et al. "A peptide mimetic of an anti-CD4 monoclonal antibody by rational design" *Biochemical and Biophysical Research Communications*, 2003, pp. 198-205, vol. 307.

Chen, Y. et al. "Selection and Analysis of an Optimized Anti-VEGF Antibody: Crystal Structure of an Affinity-matured Fab in Complex with Antigen" *J. Mol. Biol.*, 1999, pp. 865-881, vol. 293.

Coupel, S. et al. "Expression and release of a soluble HLA-E is an immunoregulatory feature of endothelial cell activation" *Blood*, Apr. 1, 2007, pp. 2806-2814, vol. 109, No. 7.

De Pascalis, R. et al. "Grafting of "Abbreviated" Complementarity-Determining Regions Containing Specificity-Determining Residues Essential for Ligand Contact to Engineer a Less Immunogenic Humanized Monoclonal Antibody" *J. Immunol*, 2002, pp. 3076-3084, vol. 169.

Derre, L. et al. "Expression and Release of HLA-E by Melanoma Cells and Melanocytes: Potential Impact on the Response of Cytotoxic Effector Cells" *J. Immunol*, 2006, pp. 3100-3107, vol. 177.

Gessner, J. E. et al. "The IgG Fc receptor family" *Ann Hematol*, 1998, pp. 231-248, vol. 76.

Gonzales, N. R. et al. "Minimizing the Immunogenicity of Antibodies for Clinical Application" *Tumor Biol*, 2005, pp. 31-43, vol. 26.

Holm, P. et al. "Functional mapping and single chain construction of the anti-cytokeratin 8 monoclonal antibody TS1" *Molecular Immunology*, 2007, pp. 1075-1084, vol. 44.

Houchins, J. P. et al. "DNA Sequence Analysis of NKG2, a Family of Related cDNA Clones Encoding Type II Integral Membrane Proteins on Human Natural Killer Cells" *J. Exp. Med.*, Apr. 1991, pp. 1017-1020, vol. 173.

Houchins, J. P. et al. "Natural Killer Cell Cytolytic Activity Is Inhibited by NKG2-A and Activated by NKG2-$C^1$" *The Journal of Immunology*, 1997, pp. 3603-3609, vol. 158.

Kashmiri, S. V. S. et al. "SDR grafting—a new approach to antibody humanization" *Methods*, 2005, pp. 25-34, vol. 36.

Kumar, S. et al. "Molecular Cloning and Expression of the Fabs of Human Autoantibodies in *Escherichia coli*" *The Journal of Biological Chemistry*, Nov. 10, 2000, pp. 35129-35136, vol. 275, No. 45.

Lanier, L. L. et al. "Arousal and inhibition of human NK cells" *Immunological Reviews*, 1997, pp. 145-154, vol. 155.

Lanier, L. L. et al. "Immunoreceptor DAP12 bearing a tyrosine-based activation motif is involved in activating NK cells" *Nature*, Feb. 12, 1998, pp. 703-707, vol. 391.

Lazetic, S. et al. "Human Natural Killer Cell Receptors Involved in MHC Class I Recognition Are Disulfide-Linked Heterodimers of CD94 and NKG2 Subunits" *The Journal of Immunology*, 1996, pp. 4741-4745, vol. 157.

Lee, N. et al. "HLA-E Surface Expression Depends on Binding of Tap-Dependent Peptides Derived from Certain HLA Class I Signal Sequences" *J. Immunol.*, 1998, pp. 4951-4960, vol. 160.

Lee, N. et al. "HLA-E is a major ligand for the natural killer inhibitory receptor CD94/NKG2A" *Proc. Natl. Acad. Sci. USA*, Apr. 1998, pp. 5199-5204, vol. 95.

Leibson, P. J. "Cytotoxic Lymphocyte Recognition of HLA-E: Utilizing a Nonclassical Window to Peer into Classical MHC" *Immunity*, Sep. 1998, pp. 289-294, vol. 9.

Llano, M. et al. "HLA-E-bound peptides influence recognition by inhibitory and triggering CD94/NKG2 receptors: preferential response to an HLA-G-derived nonamer" *Eur. J. Immunol.*, 1998, pp. 2854-2863, vol. 28.

MacCallum, R. M. et al. "Antibody-antigen Interactions: Contact Analysis and Binding Site Topography" *J. Mol. Biol.*, 1996, pp. 732-745, vol. 262.

O'Callaghan, C. A. et al. "Structural Features Impose Tight Peptide Binding Specificity in the Nonclassical MHC Molecule HLA-E" *Molecular Cell.*, Mar. 1998, pp. 531-541, vol. 1.

O'Callaghan, C. A. et al. "Structure and function of the human MHC class Ib molecules HLA-E, HLA-F and HLA-G" *Immunological Reviews*, 1998, pp. 129-138, vol. 163.

Pedersen, L. O. et al. "Differential Expression of Inhibitory or Activating CD94/NKG2 Subtypes on MART-1-Reactive T Cells in Vitiligo Versus Melanoma: A Case Report" *J. Invest Dermatol*, 2002, pp. 595-599, vol. 118.

(56) References Cited

OTHER PUBLICATIONS

Perez-Villar, J. J. et al. "Functional Ambivalence of the Kp43 (CD94) NK Cell-Associated Surface Antigen" *The Journal of Immunology*, 1995, pp. 5779-5788, vol. 154.

Petrie, E. J. et al. "CD94-NKG2A recognition of human leukocyte antigen (HLA)-E bound to an HLA class I leader sequence" *Journal of Experimental Medicine*, Mar. 17, 2008, pp. 725-735, vol. 205, No. 3.

Phillips, J. H. et al. "CD94 and a Novel Associated Protein (94AP) Form a NK Cell Receptor Involved in the Recognition of HLA-A, HLA-B, and HLA-C Allotypes" *Immunity*, Aug. 1996, pp. 163-172, vol. 5.

Plougastel, B. et al. "Cloning of NKG2-F, a new member of the NKG2 family of human natural killer cell receptor genes" *Eur. J. Immunol.*, 1997, pp. 2835-2839, vol. 27.

Posch, P. E. et al. "HLA-E Is the Ligand for the Natural Killer Cell CD94/NKG2 Receptors" *J. Biomed Sci.*, 1998, pp. 321-331, vol. 5.

Reddy, M. P. et al. "Elimination of Fc Receptor-Dependent Effector Functions of a Modified IgG4 Monoclonal Antibody to Human CD4" *The Journal of Immunology*, 2000, pp. 1925-1933, vol. 164.

Rudikoff, S. et al. "Single amino acid substitution altering antigen-binding specificity" *Proc. Natl. Acad. Sci. USA*, Mar. 1982, pp. 1979-1983, vol. 79.

Shawar, S. M. et al. "Antigen Presentation by Major Histocompatibility Complex Class I-B Molecules" *Annu. Rev. Immunol.*, 1994, pp. 839-880, vol. 12.

Sivori, S. et al. "Inhibitory CD94 Molecules Identified by the Z199 Monoclonal Antibody Recognize Different HLA-Class I Molecules" *Transplantation Proceedings*, Dec. 1996, pp. 3199-3203, vol. 28, No. 6.

Smith-Gill, S. J. et al. "Contributions of Immunoglobulin Heavy and Light Chains to Antibody Specificity for Lysozyme and Two Haptens" *The Journal of Immunology*, Dec. 15, 1997, pp. 4135-4144, vol. 139, No. 12.

Song, M. K. et al. "Light Chain of Natural Antibody Plays a Dominant Role in Protein Antigen Binding" *Biochemical and Biophysical Research Communications*, 2000, pp. 390-394, vol. 268.

Ulbrecht, M. et al. "Impaired Intracellular Transport and Cell Surface Expression of Nonpolymorphic HLA-E: Evidence for Inefficient Peptide Binding" *J. Exp. Med.*, Oct. 1992, pp. 1083-1090, vol. 176.

Ulbrecht, M. et al. "The HLA-E Gene Encodes Two Differentially Regulated Transcripts and a Cell Surface Protein" *The Journal of Immunology*, Nov. 1, 1992, pp. 2945-2953, vol. 149, No. 9.

Vajdos, F. F. et al. "Comprehensive Functional Maps of the Antigen-binding Site of an Anti-ErbB2 Antibody Obtained with Shotgun Scanning Mutagenesis" *J. Mol. Biol.*, 2002, pp. 415-428, vol. 320.

Vance, R. E. et al. "Recognition of the Class Ib Molecule Qa-1$^b$ by Putative Activating Receptors CD94/NKG2C and CD94/NKG2E on Mouse Natural Killer Cells" *J. Exp. Med.*, Dec. 20, 1999, pp. 1801-1812, vol. 190, No. 12.

Ward, E. S. et al. "Binding activities of a repertoire of single immunoglobulin variable domains secreted from *Escherichia coli*" *Nature*, Oct. 12, 1989, pp. 544-546, vol. 341.

Wu, H. et al. "Humanization of a Murine Monoclonal Antibody by Simultaneous Optimization of Framework and CDR Residues" *J. Mol. Biol.*, 1999, pp. 151-162, vol. 294.

Yokoyama, W. M. et al. "Immune Functions Encoded by the Natural Killer Gene Complex" *Nature*, Apr. 2003, pp. 304-316, vol. 3.

Sablitzky, F. et al. "Molecular basis of an isogeneic anti-idiotypic response" *The EMBO Journal*, 1984, pp. 3005-3012, vol. 3, No. 12.

Marshak-Rothstein, A. et al. "Hybridoma proteins expressing the predominant idiotype of the antiazophenylarsonate response of A/J mine" *PNAS*, Feb. 1980, pp. 1120-1124, vol. 77, No. 2.

Bandeira, N. et al. "Automated de novo protein sequencing of monoclonal antibodies" *Nature Biotechnology*, Dec. 2008, pp. 1336-1338, vol. 26, No. 12.

Casadevall, A. et al. "Immunoglobulin isotype influences affinity and specificity" *PNAS*, Jul. 31, 2012, pp. 12272-12273, vol. 109, No. 31.

Brooks, A.G. et al. "NKG2A Complexed with CD94 Defines a Novel Inhibitory Natural Killer Cell Receptor," *Journal of Experimental Medicine*, Feb. 17, 1997, vol. 185, No. 4, pp. 795-800.

Carretero, M., et al., "Specific engagement of the CD94/NKG2-A killer inhibitory receptor by the HLA-E class Ib molecule induces SHP-1 phosphatase recruitment to tyrosine-phosphorylated NKG2-A: evidence for receptor function in heterologous transfectants," *European Journal of Immunology*, 1998, vol. 28, No. 4, pp. 1280-1291.

Casadevall, A., et al., "Passive Antibody Therapy for Infectious Diseases," *Nature Reviews: Microbiology*, Sep. 2004, vol. 2, No. 9, pp. 695-703.

Coiffier, B., "Dose intensity or monoclonal antibody in first-line treatment," *The Hematology Journal*, 2004, vol. 5, pp. S154-S158.

Downs, S., et al., "Development of Antibodies Specific for NKG2 Family Members," Depts. of Monoclonal Antibodies and Antibody Applications, R&D Systems, Inc., Minneapolis, MN, 2011, p. 1.

Fang, M., et al., "CD94 Is Essential for NK Cell-Mediated Resistance to a Lethal Viral Disease," *Immunity*, Apr. 22, 2011, vol. 34, pp. 579-589.

Gatto, B., "Monoclonal Antibodies in Cancer Therapy," *Current Medical Chemistry—Anti-Cancer Agents*, 2004, vol. 4, No. 5, pp. 411-414.

Hinoda, Y., et al., "Monoclonal antibodies as effective therapeutic agents for solid tumors," *Cancer Science*, Aug. 2004, vol. 95, No. 8, pp. 621-625.

Kaiser, B.K., et al., "Interactions between NKG2x Immunoreceptors and HLA-E Ligands Display Overlapping Affinities and Thermodynamics," *The Journal of Immunology*, 2005, vol. 174, No. 5, pp. 2878-2884.

Karre, K., et al., "Selective rejection of H-2-deficient lymphoma variants suggests alternative immune defence strategy," *Nature*, Feb. 1986, vol. 319, No. 20, pp. 675-678.

Le Bouteiller, P., et al., "Antigen-presenting function(s) of the non-classical HLA-E, -F and -G class I molecules: the beginning of a story," *Research in Immunology*, May 1996, vol. 147, No. 5, pp. 301-313.

Ludewig, B., et al., "Role of dendritic cells in the induction and maintenance of autoimmune diseases," *Immunological Reviews*, 1999, vol. 169, pp. 45-54.

Martin, A.M., et al., "The genomic organization and evolution of the natural killer immunoglobulin-like receptor (KIR) gene cluster," *Immunogenetics*, 2000, vol. 51, pp. 268-280.

Miller, J.D., "Analysis of HLA-E Peptide-Binding Specificity and Contact Residues in Bound Peptide Required for Recognition by CD94/NKG2," *The Journal of Immunology*, 2003, vol. 171, pp. 1369-1375.

Miller, J.S., et al., "Human natural killer cells with polyclonal lectin and immunoglobulinlike receptors develop from single hematopoietic stem cells with preferential expression of NKG2A and KIR2DL2/L3/S2," *Blood*, Aug. 2001, vol. 98, No. 3, pp. 705-713.

Mingari, M.C., et al., "Cytolytic T lymphocytes displaying natural killer (NK)-like activity: expression of NK-related functional receptors for HLA class I molecules (p58 and CD94) and inhibitory effect on the TCR-mediated target cell lysis or lymphokine production," *International Immunology*, 1995, vol. 7, No. 4, pp. 697-703.

Mocikat, R., et al., "Natural Killer Cells Activated by MHC Class I$^{Low}$ Targets Prime Dendritic Cells to Induce Protective CD8 T Cell Responses," *Immunity*, Oct. 2003, vol. 19, No. 4, pp. 561-569.

Moretta, A., et al., "Activating Receptors and Coreceptors Involved in Human Natural Killer Cell-Mediated Cytolysis," *Annual Review of Immunology*, 2001, vol. 19, pp. 197-223.

Moretta, A., "HLA class I specific inhibitory receptors," *Current Opinion in Immunology*, 1997, vol. 9, pp. 694-701.

Moretta, L., "Unravelling natural killer cell function: triggering and inhibitory human NK receptors," *The EMBO Journal*, 2004, vol. 23, No. 2, pp. 255-259.

Ohlen, C., et al., "Prevention of Allogeneic Bone Marrow Grant Rejection by H-2 Transgene in Donor Mice," *Science*, Nov. 3, 1989, vol. 246, pp. 666-668.

(56) References Cited

OTHER PUBLICATIONS

Olszewski, A.J., et al., "Empowering Targeted Therapy: Lessons from Rituximab," *Science's STKE*, Jul. 2004, vol. 241, pp. 1-6.
O'Neill, D.W., et al., "Manipulating dendritic cell biology for the active immunotherapy of cancer," *Blood*, Oct. 15, 2004, vol. 104, No. 8, pp. 2235-2246.
Ravetch, J.V., et al., "Immune Inhibitory Receptors," *Science*, Oct. 6, 2000, vol. 290, pp. 84-89.
Roque, A.C.A., et al., "Antibodies and Genetically Engineered Relates Molecules: Production and Purification," *Biotechnology Progress*, 2004, vol. 20, No. 3, pp. 639-654.
Sharma, A., et al., "Comparative Pharmacodynamics of Keliximab and Clenoliximab in Transgenic Mice Bearing Human CD4," *The Journal of Pharmacology and Experimental Therapeutics*, 2000, vol. 293, No. 1, pp. 33-41.
Soderstrom, K., et al., "CD94/NKG2 Is the Predominant Inhibitory Receptor Involved in Recognition of HLA-G by Decidual and Peripheral Blood NK cells," *The Journal of Immunology*, Aug. 1997, vol. 159, pp. 1072-1075.
Van Beneden, K., "Expression of Ly49E and CD94/NKG2 on Fetal and Adult NK Cells," *The Journal of Immunology*, 2001, vol. 166, pp. 4302-4311.
Yawata, M., "Variation Within the Human Killer Cell Immunoglobulin-Like Receptor (KIR) Gene Family," *Critical Reviews in Immunology*, 2002, vol. 22, Nos. 5-6, pp. 463-482.
Zambello, R., "Expression and function of KIR and natural cytotoxicity receptors in NK-type lymphoproliferative diseases of granular lymphocytes," *Blood*, Sep. 1, 2003, vol. 102, No. 5, pp. 1797-1805.
Biochemistry, "http://biochemistry.ru/biohimija_severina/b5873content.html", 2003, pp. 1-10.
Kohen, F. et al. "The avidin-biotin reaction in immunoassay" *Complementary Immunoassays*, Chapter 5, 1991, pp. 1-21.
Riott, I. et al. *Immunology*, 2000, pp. 1-13.
Riott, I. et al. *Immunology*, 2000, pp. 1-11.
Singer. Genes and Genomes, 1998, vol. 1, pp. 1-3.
NCBI Database, "Gene Bank IDS GI: 20981680", Accession No. P16003, pp. 1-5.
NCBI Database, "Gene Bank IDS GI:116013" Accession No. P01730, pp. 1-13.
Demotte, N. et al. "A reversible functional defect of $CD8^+$ T lymphocytes involving loss of tetramer labeling" *Eur. J. Immunol.*, 2002, pp. 1688-1697, vol. 32.
Vitale, C. et al. "Analysis of the activating receptors and cytolytic function of human natural killer cells undergoing in vivo differentiation after allogeneic bone marrow transplantation" *Eur. J. Immunol.*, 2004, pp. 455-460, vol. 34.
Bottino, C. et al. "NTB-A, a Novel SH2D1A-associated Surface Molecule Contributing to the Inability of Natural Killer Cells to Kill Epstein-Barr Virus-infected B Cells in X-linked Lymphoproliferative Disease" *J. Exp. Med.*, Aug. 6, 2001, pp. 235-246, vol. 194, No. 3.
Mavilio, D. et al. "Natural killer cells in HIV-1 infection: Dichotomous effects of viremia on inhibitory and activating receptors and their functional correlates" *PNAS*, Dec. 9, 2003, pp. 15011-15016, vol. 100, No. 25.
PNAS Information for Authors, Oct. 2013, pp. i-vi, vol. 110.
Vance, R. et al. "Implications of CD94 deficiency and monoallelic NKG2A expression for natural killer cell development and repertoire formation" *PNAS*, Jan. 22, 2002, pp. 868-873, vol. 99, No. 2.
Paul, W. E. et al. "Fundamental Immunology" $3^{rd}$ edition, Chapter 9, 1993, pp. 292-295.
Brown, M. et al. "Tolerance to Single, but Not Multiple, Amino Acid Replacements in Antibody $V_H$ CDR2" *The Journal of Immunology*, 1996, pp. 3285-3291, vol. 156, No. 9.
Pridgeon, C. et al. "Natural killer cells in the synovial fluid of rheumatoid arthritis patients exhibit a $CD56^{bright}, CD94^{bright}, CD158^{negative}$ phenotype" *Rheumatology*, 2003, pp. 870-878, vol. 42.
Cooper, M. A. et al. "NK cell and DC interactions" *Trends in Immunology*, Jan. 2004, pp. 47-52, vol. 25, No. 1.
Teixeira De Matos, C. et al. "Activating and inhibitory receptors on synovial fluid natural killer cells of arthritis patients: role of CD94/NKG2A in control of cytokine secretion" *Immunology*, 2007, pp. 291-301, vol. 122.
Leavenworth, J. W. et al. "Mobilization of natural killer cells inhibits development of collagen-induced arthritis" *PNAS*, Aug. 30, 2011, pp. 14584-14589, vol. 108, No. 35.
Park, K. S. et al. "Inhibitory NKG2A and activating NKG2D and NKG2C natural killer cell receptor genes: susceptibility for rheumatoid arthritis" *Tissue Antigens*, 2008, pp. 342-346, vol. 72.
Lu, L. et al. "Regulation of Activated $CD4^+$ T Cells by NK Cells via the Qa-1-NKG2A Inhibitory Pathway" *Immunity, Cell Press*, May 2007, pp. 593-604, vol. 26.
Zhang, A. L. et al. "Natural killer cells trigger differentiation of monocytes into dendritic cells" *Blood*, Oct. 1, 2007, pp. 2484-2493, vol. 110, No. 7.
Fauser, A. A. et al. "Guidelines for Anti-emetic Therapy: Acute Emesis" *European Journal of Cancer*, 1999, pp. 361-370, vol. 35, No. 3.
Bioss Antibodies [online], "NKG2A Polyclonal Antibody" retrieved on Aug. 16, 2017, retrieved from the internet, URL: https://www.biosusaantibodies.com/store/datasheets/bs-2411R, p. 1.
Hall, *Supplementary Methods*, 2013, pp. 1-5.
Nielsen, N. et al. "Cytotoxicity of $CD56^{bright}$ NK Cells towards Autologous Activated $CD4^+$ T Cells Is Mediated through NKG2D, LFA-1 and TRAIL and Dampened via CD94/NKG2A" *PLoS One*, Feb. 22, 2012, pp. 1-10, vol. 7, No. 2.
Nielsen, N. et al. "Balance between activating $NKG_2D$, $DNAM_{-1}$, $NKp_{44}$ and $NKp_{46}$ and inhibitory $CD_{94}/NKG_2A$ receptors determine natural killer degranulation towards rheumatoid arthritis synovial fibroblasts" *Immunology*, 2014, pp. 581-593, vol. 142.

\* cited by examiner

Reconstitution of lysis with anti-NKG2A mAbs

Reconstitution of lysis with anti-NKG2A mAbs

Reconstitution of lysis with anti-NKG2A mAbs

Binding of anti-NKG2a mAb, clone Z270 to cynomolgus monkey
NK bulk day 16 (300u/ml)

Binding of anti-NKG2a mAb, clone Z270 to cynomolgus monkey NK bulk day 16 (300u/ml)

MONOCLONAL ANTIBODIES AGAINST NKG2A

CROSS-REFERENCE TO RELATED APPLICATIONS

This application is a divisional of U.S. Ser. No. 11/720,553, filed May 31, 2007, which is the U.S. national stage application of International Patent Application No. PCT/M2005/004013, filed Dec. 27, 2005, which claims the benefit of U.S. Provisional Patent Application No. 60/639,465, filed Dec. 28, 2004, and U.S. Provisional Patent Application No. 60/639,832, filed Dec. 28, 2004, the disclosures of which are hereby incorporated by reference in their entireties, including all figures, tables and amino acid or nucleic acid sequences.

FIELD OF THE INVENTION

The present invention relates to monoclonal antibodies and fragments thereof directed against the NK cell surface receptor NKG2A, as well as to methods of producing and evaluating such antibodies. The monoclonal antibodies and fragments thereof are useful in treating immune disorders, particularly autoimmune disorders, as well as other diseases requiring modulated NK cell function. Generally, the present methods involve the use of the antibodies and fragments thereof to prevent the stimulation of NKG2A receptors on NK cells, leading to the lysis of HLA-E or Qa1$^b$ expressing cells, such as dendritic cells or activated T cells, that contribute to the pathology of the disorders to be treated.

BACKGROUND

Maintaining effective immune surveillance without provoking autoimmune reactions requires the precise titration of effector T cell responses. Autoimmune disorders arise when the immune system mounts an immune response against self-antigens (see, e.g., Ludewig et al. (1999) Immunol Rev. 169:45-54). While the mechanisms involved in the triggering and maintenance of autoimmune reactions is unclear, it is likely that the appearance of previously immunologically ignored antigens in secondary lymphoid organs is involved.

Dendritic cells are bone-marrow derived antigen presenting cells (APCs) that play a key role in the immune response (see, e.g., O'Neill et al. (2004) Blood 104:2235-2246). DCs internalize bacteria, viruses, dying cells, and various complex molecules through phagocytosis, endocytosis, and pinocytosis. Incorporated proteins are broken down into peptides, which are then presented on the DC cell surface along with MHC class I and class II molecules. Antigens loaded onto MHC class I are typically derived from endogenous proteins and are recognized by CD8+ T cells, whereas MHC class II loaded antigens are generally derived from external proteins and are recognized by CD4+ T cells. Following antigen capture, immature DC cells mature to form mature DCs which show reduced phagocytosis, migrate to lymphoid tissues, and have enhanced T cell stimulation capacity.

In lymphoid tissues, DCs prime naïve T cells, stimulating their clonal expansion and differentiation, and can also interact with B cells and cells of the innate immune system, including NK cells. Activated NK cells can kill immature, but not mature, DC cells. As antigen transport and primary sensitization of T lymphocytes is mainly mediated by antigen presenting dendritic cells, it is likely that the inappropriate presentation of self antigens by dendritic cells contributes at least in part to autoimmune disorders.

Natural killer (NK) cells are a subpopulation of lymphocytes involved in non-conventional immunity. NK cells provide an efficient immunosurveillance mechanism by which undesired cells such as tumor or virally-infected cells can be eliminated. NK cell activity is regulated by a complex mechanism that involves both activating and inhibitory signals (see, e.g., Moretta et al. (2001) Annu Rev Immunol 19:197-223; Moretta et al. (2003) EMBO J EPub December 18; Ravetch et al. (2000) Science 290:84-89; Zambello et al. (2003) Blood 102:1797-805; Moretta et al. (1997) Curr Opin Immunol 9:694-701; the entire disclosures of which are herein incorporated by reference).

Several distinct NK-specific receptors have been identified that play important roles in the NK cell mediated recognition and killing of HLA Class I deficient target cells. These receptors, termed NKp30, NKp46 and NKp44, are members of the Ig superfamily. Their cross-linking, induced by specific mAbs, leads to a strong NK cell activation resulting in increased intracellular $Ca^{++}$ levels, triggering of cytotoxicity, and lymphokine release. Importantly, mAb-mediated activation of NKp30, NKp46, and/or NKp44 results in an activation of NK cytotoxicity against many types of target cells. These findings provide evidence for a central role of these receptors in natural cytotoxicity.

NK cells are negatively regulated by major histocompatibility complex (MHC) class I-specific inhibitory receptors (Kärre et al. (1986) Nature 319:675-8; Ohlen et al, (1989) Science 246:666-8). These specific receptors bind to polymorphic determinants of major histocompatibility complex (MHC) class I molecules or HLA and inhibit natural killer (NK) cell lysis. In humans, certain members of a family of receptors termed killer Ig-like receptors (KIRs) recognize groups of HLA class I alleles (see, e.g., Yawata et al. (2002) Crit Rev Immunol 22:463-82; Martin et al. (2000) Immunogenetics. 51:268-80; Lanier (1998) Annu Rev Immunol. 16:359-93; the entire disclosures of which are herein incorporated by reference).

Another important inhibitory receptor on NK cells is CD94-NKG2A, which interacts with the non-classical MHC class 1 molecule HLA-E (see, e.g., Braud et al. (1998) Nature 391:795-799; Lee et al. (1998) PNAS 95:5199-5204; Vance et al. (2002) PNAS 99:868-873; Brooks et al. (1999) J Immunol 162:305-313; Miller et al. J Immunol (2003) 171:1369-75; Brooks et al. (1997) J Exp Med 185:795-800; Van Beneden et al. (2001) 4302-4311; U.S. patent application no. 20030095965; the entire disclosures of each of which are herein incorporated by reference). Some of these receptors have the capacity to modulate thresholds of T cell antigen receptor-dependent T cell activation. In the rare absence of inhibitory receptors, the activating isoforms may augment T cell effector functions and contribute to autoimmune pathology. The amino acid sequence of NKG2A varies among mammals, including among primates. For example, the human and rhesus monkey versions of the NKG2A proteins share less than 90% identity, including approximately 86% within the ligand binding domain.

Efforts towards therapeutics for modulating NKG2A, essentially for the prevention of inflammation, have focused on the study of the nonclassical MHC class I molecules, HLA-E for the human receptor and Qa-1b for the mouse receptor. For cell surface expression, these MHC molecules preferentially bind peptides derived from the signal peptides of other MHC class I molecules. The expression of other class I MHC molecules can regulate the expression of HLA-E, thereby allowing NK cells to monitor the state of the MHC class I dependent antigen presentation pathway in potential target cells. The level of cell surface HLA-E is critical for the NK cell cytotoxicity towards tumor and virally infected cells. Therapeutic strategies for modulating HLA-E expression or function have generally been directed towards using HLA-I or HSP60 peptides to induce a protective state for the prevention of inflammation such that NK cells are not activated.

United States patent publication 20030095965 discloses an antibody, 3S9, that binds to NKG2A, NKG2C and NKG2E. 3 S9 purportedly causes cross-linking of those receptors and concomitant inhibition of NK cell-mediated lysis. Co-owned PCT patent publication WO 2005/105849 discloses the use of an antibody that specifically binds to an NK receptor, including NKG2A, to treat a patient suffering from NK-type lymphoproliferative disease of granular lymphocytes (NK-LDGL). Such antibodies inhibit NK cell activity.

Monoclonal antibodies have proven to be enormously useful for the diagnosis and treatment of various diseases. Therapeutic monoclonal antibodies can act through different mechanisms. Some antibodies, such as Rituxan, recognize antigens (CD20 in the case of Rituxan) present on the surface of pathological cells, e.g., tumor cells, and act by directing the immune system to destroy the recognized cells. Other antibodies, such as Bexxar, Oncolym, or Zevalin, are coupled to radioisotopes, chemotherapeutic agents, or toxins, leading to the direct killing of cells bound by the antibodies. Still others, such as Basiliximab and Daclizumab (which block IL-2), the IgE blocking Omalizumab, and efaluzimab, act to block the activity of specific proteins. Antibody based therapies are well known in the art and are reviewed, e.g., in Gatto (2004) Curr Med Chem Anti-Canc Agents 4(5):411-4, Casadevall et al. (2004) Nat Rev Microbiol. 2(9):695-703, Hinoda et al. (2004) Cancer Sci. 95(8): 621-5, Olszewski et al. (2004) Sci STKE. July 06(241): pe30, Coiffier (2004) Hematol J. Suppl 3:S154-8, Roque et al. (2004) Biotechnol Prog. 20(3):639-54, the entire disclosures of each of which is herein incorporated by reference.

Before antibodies can be used for therapeutic applications in humans, or enter clinical trials, they must go through pre-clinical studies in non-human animals to assess various parameters such as their toxicity, in vivo efficacy, bioavailability, half-life and various other pharmacokinetic and pharmacodynamic parameters. Such assays are typically carried out in mammals, and, preferably, where they have biological activity, i.e. where the mAb is reacting to the homolog molecule in the specie, therefore where one can expect the greatest physiological similarity to humans. However, studies in nonhuman primates can be impeded if an antibody directed against a human protein does not bind to the nonhuman animal homolog of the target protein. When crossreactivity is present, in contrast, not only can the in vivo efficacy of the antibody be tested in the animal, but other issues such as side effects, toxicity, or kinetic properties that are related to the binding of the antibody to the target protein can be studied as well. Examples of readily available primates include the New World monkeys and Old World monkeys, such as the cynomolgus monkey (*Macaca mulatta*), the rhesus macaque (*Macacus mulatta*), the African green monkey (Chlorocebus *aethiops*), the marmoset (*Callithrix jacchus*), the saïmiri (*Saimiri sciureus*), all available from "Centre de Primatologie" (CDP:ULP, Fort Foch, 67207 Niederhausbergen, France), and the baboon (*Papio hamadryas*) available from "Station de Primatologie du CNRS", CD56, 13790 Rousset/Arc, France). Chimpanzees and apes in general may also be used for testing a candidate medicament, although such instances are rare and generally only when no other alternative for testing exists or has been exhausted.

As antibodies bind to specific 3-dimensional features of their targets, slight changes in the amino acid sequence of a target protein can abolish binding altogether, making it unpredictable whether a given antibody directed against a protein from one species will also bind to homologous proteins sharing some but not complete sequence identity. Many instances have been described in which antibodies directed against a human protein, for example, do not bind to homologs in even closely related species. For example, some antibodies against the human CD4 protein do not bind to monkey homologs, even though the human and rhesus monkey CD4 proteins share close to 94% percent identity (see, e.g., Genbank IDs GI:116013 and 20981680; Sharma et al. (2000) JPET 293:33-41, 2000, the entire disclosures of which are incorporated herein by reference). Other examples include some antibodies against human CD3, a widely pursued pharmaceutical target for antibody development; antibodies, for example UCHT2, otherwise having properties suitable for development do not crossreact with the monkey CD3 protein.

In view of the prominence and severity of many autoimmune disorders, and the role of mature dendritic cells in coordinating the immune response against self-antigens, there is a great need in the art for new and effective therapies that modulate the activity or level of dendritic cells underlying such disorders. Moreover, there is a need for therapies against disorders characterized by aberrant cells (e.g., certain cancer or virally infected cells) that are able to shield themselves from destruction by the immune system. Finally, there is also a need to find a valid in vivo test system for the therapeutic potential in humans of monoclonal antibodies against NKG2A. The present invention addresses this and other needs.

SUMMARY OF THE INVENTION

The present invention provides monoclonal antibodies and fragments thereof directed against the NKG2A receptor. The monoclonal antibodies and fragments thereof of this invention may either inhibit the ability of NK cells to lyse normally susceptible target cells ("NK cell inhibitory antibodies") or reconstitute the ability of NK cells to lyse otherwise protected target cells ("NK cell activating antibodies"). The function of the monoclonal antibodies and fragments thereof of this invention is dependent upon their ability to bind to an Fc receptor.

Fc receptors, such as Fc gamma receptors, are expressed on the surface of leukocytes. These receptors bind to the Fc portion of immunoglobulin (Ig), e.g. Fc gamma receptors bind to the Fc portion of IgG. This binding helps contribute to immune function by linking the recognition of antigens by antibodies with cell-based effector mechanisms. Different immunoglobulin classes trigger different effector mechanisms through the differential interaction of immunoglobulin Fc regions with specific Fc receptors (FcRs) on immune cells. Activating Fc gamma receptors include Fc gamma RI, Fc gamma RITA, Fc gamma RIIC, and Fc gamma RIII A. Fc gamma RIIB is considered an inhibitory Fc gamma receptor. (For review, see, e.g., Woof et al. (2004) Nat Rev Immunol. 4(2):89-99; Baumann et al. (2003) Arch Immunol Ther Exp (Warsz) 51(6):399-406; Pan et al. (2003) Chin Med J (Engl) 116(4):487-94; Takai et al. (1994) Cell 76:519-529; Ravetch et al. (2001) Annu Rev Immunol 19:275-290, the entire disclosures of each of which are herein incorporated by reference).

Without being bound by theory, the inventors believe that the presence of an Fc receptor binding region in the antibodies and fragments of this invention causes inhibition of NK cell lysis in the presence of a cell bearing an Fc receptor. Those antibodies and fragments that lack an Fc receptor binding region are capable of reconstituting NK cell lysis of target cells bearing HLA-E or Qa1$^b$ on their cell surface. Such target cells are typically protected against NK cell lysis through the interaction of HLA-E or Qa1$^b$ with the NKG2A receptor.

The invention also provides compositions comprising the antibodies and fragments of this invention, as well as therapeutic methods utilizing such compositions for treating different diseases and disorders. The invention further provides methods for using non-human primates to evaluate and characterize the activity, toxicity and proper dosing regimen of an antibody or fragment thereof against human NKG2A.

In one aspect, accordingly, the present invention provides an activating antibody that is a monoclonal antibody or a fragment thereof characterized by: a) specifically binding to NKG2A; b) not specifically binding to an Fc receptor; and c) when bound to NKG2A on a human NK cell, causing said NK cell to lyse a target human cell bearing HLA-E or Qa1$^b$ on the target cell surface, when said target cell comes into contact with said NK cell. Preferably, the monoclonal antibody or fragment does not bind to other human NKG2 receptors, specifically the activating receptors NKG2C or NKG2E. Even more preferred is that the antibody or fragment of this invention completely compete with an anti-NKG2 monoclonal selected from Z199 or Z270.

In one preferred embodiment, the monoclonal antibody or a fragment thereof is capable of binding to a non-human primate NKG2A. Even more preferred is when upon binding to NKG2A on a non-human primate NK cell, the monoclonal antibody or a fragment thereof has the ability to reconstitute lysis of a target non-human primate cell bearing HLA-E on the target cell surface, when said target cell comes into contact with said NK cell.

In another preferred embodiment, the monoclonal antibody or a fragment thereof comprises the amino acids sequence of the variable heavy chain region of Z270 or the variable light chain region of Z270. In an alternate preferred embodiment, the monoclonal antibody or a fragment thereof comprises the amino acids sequence of the variable heavy chain region of Z199 or the variable light chain region of Z199.

In yet another preferred embodiment, the monoclonal antibody or a fragment thereof comprises a mouse or human IgG$_1$ constant region that has been modified to prevent binding to an Fc receptor, or a human IgG$_4$ constant region.

In another preferred embodiment, the antibody or fragment is chimeric or humanized. More preferred is an antibody or fragment thereof that comprises ch270VK or ch270VH.

In another embodiment, the antibody or fragment thereof is derivatized to enhance its bioavailability or stability in vivo. In another embodiment, the antibody is derivatized with PEG.

The activating antibodies and fragments of this invention are useful to reconstitute lysis of certain target cells that are normally resistant to NK cell-mediated lysis. Thus, in another embodiment the invention provides a method of reconstituting NK cell-mediated lysis of a target cell in a population comprising a NK cell and said target cell, wherein said NK cell is characterized by NKG2A on its surface, and said target cell is characterized by the presence of HLA-E or Qa1$^b$ on its surface, said method comprising the step of contacting said NK cell with a monoclonal antibody or a fragment described above. Preferably, the target cell is a human cell. More preferably, the target cell is a dendritic cell ("DC"), a cancer cell or a virally-infected cell. Most preferably, the target is a mature dendritic cell ("mDC").

The activating antibodies and fragments thereof may be formulated into compositions additionally comprising a pharmaceutically acceptable carrier or excipient. Such composition may be formulated so as to be suitable for pharmaceutical administration. The pharmaceutical compositions may optionally comprise a second therapeutic agent useful for the particular disease or condition being treated. All such compositions are also part of the present invention.

The activating antibody compositions of this invention may be utilized to treat or prevent in a patient an autoimmune or inflammatory disorder, or an immune response; or to treat in a patient a cancer characterized by the presence of a cancer cell expressing HLA-E or Qa1$^b$ on its surface, or a viral disease characterized by the presence of a virally infected cell expressing HLA-E or Qa1$^b$ on its surface. These methods may additionally comprise the step of administering to the patient a second therapeutic agent useful for the particular disease or condition being treated. The second therapeutic agent may be administered either as a separate dosage form or as part of said composition.

In one embodiment, the second therapeutic agent in the compositions comprising and the methods utilizing an activating antibody or fragment of the invention is a compound that agonizes an activating an NK cell receptor, such as NKp30, NKp44, and NKp46. In another embodiment, the second therapeutic agent is an antagonist of an inhibitory NK cell receptor, such as an inhibitor KIR receptor. In another embodiment, the second therapeutic agent is an antagonist of TGF-beta 1. In another embodiment, the second therapeutic agent is selected from the group consisting of a cytokine inhibitor, a hematopoietic growth factor, a pain reliever, insulin, an anti-inflammatory agent, and an immunosuppressant. In another embodiment, the second therapeutic agent is an anticancer compound or an antiemetic. In another embodiment, the second therapeutic agent is an antiviral compound.

In another embodiment, the autoimmune or inflammatory disorder to be prevented or treated is selected from the group consisting of autoimmune hemolytic anemia, pernicious anemia, polyarteritis nodosa, systemic lupus erythematosus, Wegener's granulomatosis, Alzheimer's disease, autoimmune hepatitis, Behçet's disease, Crohn's disease, primary bilary cirrhosis, scleroderma, ulcerative colitis, Sjögren's syndrome, Type 1 diabetes mellitus, uveitis, Graves' disease, thyroiditis, Type 1 diabetes mellitus, myocarditis, rheumatic fever, ankylosing spondylitis, rheumatoid arthritis, glomerulonephritis, sarcoidosis, dermatomyositis, myasthenia gravis, polymyositis, Guillain-Barré syndrome, multiple sclerosis, alopecia areata, pemphigus/pemphigoid, psoriasis, and vitiligo.

In another aspect, the present invention provides an inhibitory monoclonal antibody or an inhibitory fragment thereof characterized by: a) specifically binding to NKG2A; b) specifically binding to an Fc receptor; c) not binding to NKG2C or NKG2E; d) complete competition with Z270 or Z199; e) being able to inhibit NK cell lysis of an NK cell-susceptible target cell, wherein said cross-linking monoclonal antibody is not Z199. In one preferred embodiment, the inhibitory antibody is further characterized by binding to a non-human primate NKG2A.

In a more preferred embodiment, the inhibitory antibody or fragment thereof comprises an amino acid sequence of the variable light chain region of Z270 or an amino acid sequence of the variable heavy chain region of Z270. In one of the most preferred embodiments, the antibody is Z270.

In another preferred embodiment, the inhibitory antibody or fragment is chimeric or humanized. More preferred is an inhibitory antibody or inhibitory fragment thereof that comprises ch270VK or ch270VH. In another of the most preferred embodiments, the antibody is chZ270 or Z270.

In another embodiment, the invention provides a composition comprising an effective amount of an inhibitory antibody or inhibitory fragment thereof described above, or Z199; and a pharmaceutically acceptable carrier or excipient. These inhibitory antibody compositions are preferably formulated for pharmaceutical use.

The inhibitory antibody compositions of this invention optionally comprise a second therapeutic agent useful to treat a disease or condition characterized by undesired NK cell-mediated lysis of other cells, hyperactive NK cell activity, or unwanted NK cell proliferation. Such second therapeutic agents may be selected from, for example, a cytokine, an anticancer compound (such as a chemotherapeutic compound, an anti-angiogenic compound, an apoptosis-promoting compound, a hormonal agent, a compound that interferes with DNA replication, mitosis and/or chromosomal segregation, or an agent that disrupts the synthesis and fidelity of polynucleotide precursors), an adjunct compound, a compound capable of stimulating an inhibitory NK cell receptor (such as natural ligands, antibodies or small molecules that can stimulate the activity of CD94/NKG2A receptors, or an inhibitory KIR receptor such as KIR2DL1, KIR2DL2, KIR2DL3, KIR3DL1, and KIR3DL2), or an inhibitor of an activating NK cell receptor (such as NKp30, NKp44, or NKp46).

The inhibitory antibody and fragments of this invention may be utilized in a method of reducing NK cell-mediated lysis of cells. Alternatively, the inhibitory antibody and fragments of this invention may be utilized in a method of reducing the number of NK cells in a cell population. Both of these methods comprise the step of contacting said NK cell with the inhibitor monoclonal antibody or fragment.

The pharmaceutically suitable compositions of this invention comprising an inhibitory antibody may be employed in a method of treating or preventing a patient suffering from a condition or disorder characterized by undesired NK cell-mediated lysis of other cells, hyperactive NK cell activity, or unwanted NK cell proliferation, said method comprising the step of administering to the patient said composition. One such condition is NK-LDGL. NK-LDGL (NK-type lymphoproliferative disease of granular lymphocytes; alternatively called NK-LGL) refers to a class of proliferative disorders that is caused by the clonal expansion of NK cells or NK-like cells, i.e., large granular lymphocytes showing a characteristic combination of surface antigen expression (e.g., CD3−, CD56+, CD16+, etc.; see, e.g., Loughran (1993) Blood 82:1).

In an alternate embodiment, any of the methods utilizing an inhibitory antibody of this invention may comprise the additional step of administering to said patient a second therapeutic agent. The second therapeutic agent is an agent normally used to treat a disease or condition characterized by undesired NK cell-mediated lysis of other cells, hyperactive NK cell activity, or unwanted NK cell proliferation. Examples of such agents are set forth above. The second therapeutic agent may be administered as a separate dosage form or as a component of the inhibitory antibody or fragment composition.

In another aspect, the present invention provides kits comprising any one or more of the herein-described antibodies or fragments thereof. Typically, the kit also comprises instructions for using the antibodies according to the present methods. In a related embodiment, the kit additionally comprises, in a separate vessel, a second therapeutic agent, such as any of those described above for use in conjunction with either activating or inhibitory antibodies or fragments in the treatment or prevention of various diseases or conditions.

According to another aspect, the invention provides a method of evaluating an antibody against human NKG2A comprising the steps of: a) contacting said antibody with a non-human primate cell characterized by NKG2A on its surface, or a non-human primate NKG2A polypeptide; and b) assessing the ability of said antibody to bind to or affect the activity of said cell or polypeptide. In a related embodiment, the method is used to evaluate an activating antibody; said antibody is contacted with a cell population comprising a non-human primate NK cell and a target cell, wherein said NK cell is characterized by NKG2A on its surface, and said target cell is characterized by the presence of HLA-E on its surface; and said assessing step is determining if said target cell is lysed.

In another embodiment, the invention provides a method of producing an antibody suitable for use in disease treatment in humans, said method comprising: a) immunizing a nonhuman mammal with a composition comprising human NKG2A; b) selecting a monoclonal antibody that binds NKG2A, but not NKG2C or NKG2E; c) rendering said antibody suitable for use in humans; d) administering said antibody to a nonhuman primate; and e) evaluating the ability of said antibody to bind to NKG2A in vivo in said primate and the tolerance of said primate to said antibody. If the antibody binds to and is tolerated by said nonhuman primate, it indicates that said antibody is suitable for use in disease treatment in humans. In a preferred embodiment, the method comprises the additional step of modifying said antibody to not bind an Fc receptor prior to step d.

The invention also provides an antibody produced by this method.

In yet another embodiment, the invention provides a method of identifying a suitable administration regimen for a therapeutic antibody directed against human NKG2A, said method comprising: a) administering said antibody to a nonhuman primate using a series of administration regimens in which the dose or frequency of said antibody is varied; and b) determining the activity of NKG2A-expressing cells in said non-human primate and the tolerance of said primate for each of said administration regimens. Once it is determined that a regimen is tolerated by said primate and leads to a detectable modulation in said activity of NKG2A-expressing cells, that administration regimen is considered suitable for use in humans.

According to an alternative embodiment, the invention provides a conjugate comprising: a) an inhibitory or activating antibody, and b) a cytotoxic agent. The resulting conjugate is used to kill NK cells. Thus, conjugation of an activating antibody with a cytotoxic agent will produce a molecule that will kill the NK cell, as opposed to the activation of that cell achieved by the activating antibody alone. The cytotoxin/antibody conjugates of this invention can be formulated into compositions and used in methods in a manner similar to the inhibitory antibodies of this invention.

DETAILED DESCRIPTION OF THE INVENTION

Introduction

Figure 1:
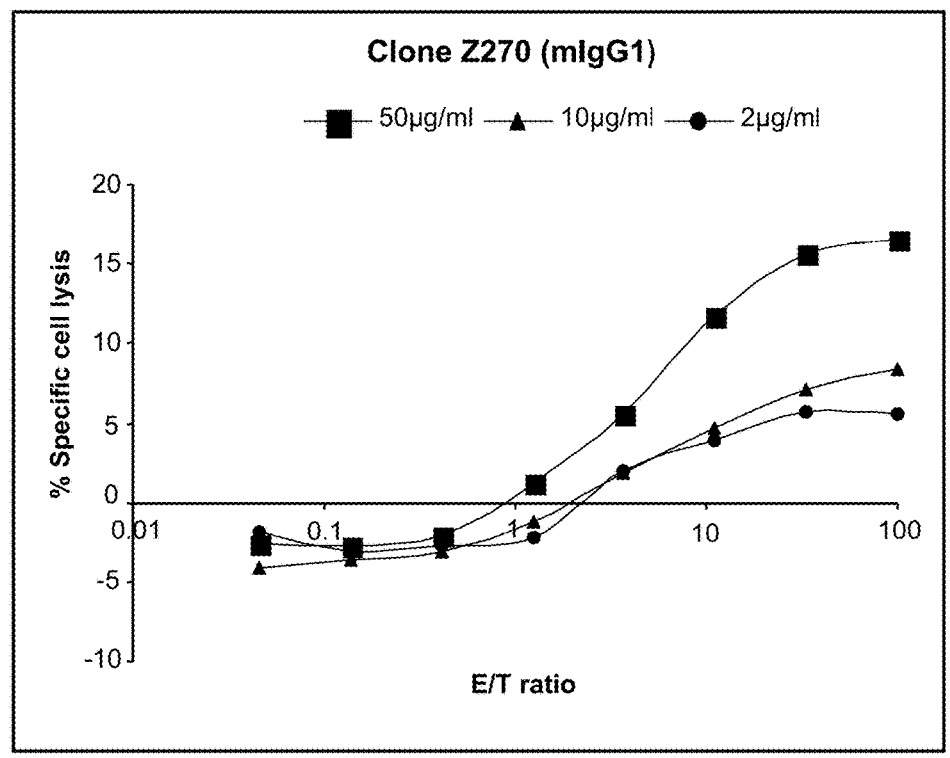
FIG. 1 depicts the effect of three different concentrations of Z270 on NK cell lysis of HLA-E expressing PHA blasts at varying ratios of NK cells to PHA blasts.

The present invention provides novel antibodies against NKG2A that activate NK cell-mediated lysis of target cells characterized by the presence of cells expressing HLA-E or Qa1$^b$ on their cell surface, methods for producing, evaluating and characterizing those antibodies for therapeutic use, and compositions comprising and methods of using those antibodies for the treatment of autoimmune or inflammatory disorders and other conditions characterized by the presence of cells expressing HLA-E or Qa1$^b$ on their cell surface, such as dendritic cells. The present invention is based, in part, on the surprising discovery that NKG2A has a primary responsibility for inhibiting the lysis of mature dendritic cells by many NK cells. Mature dendritic cells express significant levels of HLA-E, which acts through NKG2A receptors present on NK cells to inhibit the targeting of the dendritic cells. Accordingly, without being bound by the following theory, it is believed that blocking the NKG2A-mediated inhibition of NK cells leads to an increase in dendritic cell targeting by NK cells, thereby providing an effective treatment for autoimmune or inflammatory disorders or indeed any condition that could be alleviated or cured by reducing the activity of dendritic cells, particularly mature dendritic cells. The present invention thus also provides methods of, more generally, inhibiting or reducing the number of dendritic cells, preferably mature dendritic cells, in a mammal, as well as to generally reduce an immune response, preferably an autoreactive immune response.

Conversely, the present invention also provides novel antibodies against NKG2A that inhibit NK cell-mediated lysis of target cells, methods of producing, evaluating and characterizing those antibodies for therapeutic use, and compositions comprising and methods of using those antibodies for the treatment of autoimmune disorders or transplant rejection.

Definitions

As used herein, the following terms have the meanings ascribed to them unless specified otherwise.

As used herein, "NK" cells refers to a sub-population of lymphocytes that is involved in non-conventional immunity. NK cells can be identified by virtue of certain characteristics and biological properties, such as the expression of specific surface antigens including CD16, CD56 and/or CD57, the absence of the alpha/beta or gamma/delta TCR complex on the cell surface, the ability to bind to and kill cells that fail to express "self" MHC/HLA antigens by the activation of specific cytolytic enzymes, the ability to kill tumor cells or other diseased cells that express a ligand for NK activating receptors, and the ability to release protein molecules called cytokines that stimulate or inhibit the immune response. Any of these characteristics and activities can be used to identify NK cells, using methods well known in the art.

Dendritic cells are a heterogeneous population of immune cells produced in the bone marrow (see, e.g., O'Neill et al. (2004) Blood 104:2235-2246, Mohamadzadeh et al. (2004) J Immune Based Ther Vaccines. 2004; 2: 1; the entire disclosures of which are herein incorporated by reference). As referred to herein, DCs can include DC precursors, immature DCs, and mature DCs. DC precursors and immature DCs are lineage negative (CD3−CD14−CD19−CD56−) HLA-DR+ mononuclear cells. These cells can be further classified into two populations, myeloid DCs and plasmacytoid DCs. Myeloid DCs are CD11c+ and CD123 low and have a monocytoid appearance, and plasmacytoid DCs are CD11c− and CD123 high, with morphological features similar to plasma cells. Following antigen capture, DCs undergo a process of maturation in which the captured antigens are processed into peptides and loaded onto MHC class I or II for presentation on the cell surface. Mature DCs show lower phagocytic uptake, have cytoplasmic extensions called veils, migrate to lymphoid tissues, and express characteristic markers such as CD83 and DC-LAMP. TLRs are also expressed in DCs, with different DC types expressing different TLR markers (see, e.g., O'Neill et al. (2004).

NKG2A (OMIM 161555, the entire disclosure of which is herein incorporated by reference) is a member of the NKG2 group of transcripts (Houchins, et al. (1991) J. Exp. Med. 173:1017-1020). NKG2A is encoded by 7 exons spanning 25 kb, showing some differential splicing. NKG2A is an inhibitory receptor found on the surface of NK cells. Like inhibitory KIR receptors, it possesses an ITIM in its cytoplasmic domain. As used herein, "NKG2A" refers to any variant, derivative, or isoform of the NKG2A gene or encoded protein. Also encompassed are any nucleic acid or protein sequences sharing one or more biological properties or functions with wild type, full length NKG2A, and sharing at least 70%, 80%, 90%, 95%, 96%, 97%, 98%, 99%, or higher nucleotide or amino acid identity. NKG2A is also referred to as the "NKG2A receptor" throughout this disclosure.

NKG2C (OMIM 602891, the entire disclosure of which is herein incorporated by reference) and NKG2E (OMIM 602892, the entire disclosure of which is herein incorporated by reference) are two other members of the NKG2 group of transcripts (Gilenke, et al. (1998) Immunogenetics 48:163-173). NKG2C and NKG2E are activating receptors found on the surface of NK cells. As used herein, "NKG2C" and "NKG2E" refer to any variant, derivative, or isoform of the NKG2C or NKG2E gene or encoded protein, respectively. Also encompassed are any nucleic acid or protein sequences sharing one or more biological properties or functions with wild type, full length NKG2C or NKG2E, and sharing at least 70%, 80%, 90%, 95%, 96%, 97%, 98%, 99%, or higher nucleotide or amino acid identity with the disclosed gene or encoded protein.

CD94 (OMIM 602894, the entire disclosure of which is herein incorporated by reference in its entirety) is an antigen preferentially expressed on NK cells (Chang et al. (1995)

Europ. J. Immun. 25: 2433-2437). CD94 is expressed as 3 major transcripts of 0.8, 1.8, and 3.5 kb and a minor transcript of 5.5 kb in NK cell lines, and encodes a protein with a 147-amino acid extracellular domain and several motifs characteristic of C-type lectins. The amino acid sequence of CD94 is 27 to 32% identical to those of NKG2 family members NKG2A, NKG2C, NKG2D, and NKG2E. Due to the virtual absence of a cytoplasmic domain, CD94 requires association with other receptors forming disulfide-bonded heterodimers with NKG2A, NKG2C, and NKG2E (Lazetic et al. (1996) J. Immun. 157: 4741-4745). As used herein, "CD94" refers to any variant, derivative, or isoform of the CD94 gene or encoded protein. Also encompassed are any nucleic acid or protein sequences sharing one or more biological properties or functions with wild type, full length CD94, and sharing at least 70%, 80%, 90%, 95%, 96%, 97%, 98%, 99%, or higher nucleotide or amino acid identity.

HLA-E (OMIM 143010, the entire disclosure of which is herein incorporated by reference) is a nonclassical MHC molecule that is expressed on the cell surface and regulated by the binding of peptides derived from the signal sequence of other MHC class I molecules. HLA-E binds natural killer (NK) cells and some T cells, binding specifically to CD94/NKG2A, CD94/NKG2B, and CD94/NKG2C, and not to the inhibitory KIR receptors (see, e.g. OMIM 604936, the entire disclosure of which is herein incorporated by reference) (see, e.g., Braud et al. (1998) Nature 391:795-799, the entire disclosure of which is herein incorporated by reference). Surface expression of HLA-E is sufficient to protect target cells from lysis by CD94/NKG2A+NK cell clones. As used herein, "HLA-E" refers to any variant, derivative, or isoform of the HLA-E gene or encoded protein. Also encompassed are any nucleic acid or protein sequences sharing one or more biological properties or functions with wild type, full length HLA-E, and sharing at least 70%, 80%, 90%, 95%, 96%, 97%, 98%, 99%, or higher nucleotide or amino acid identity.

$Qa1^b$ is a mouse cell surface antigen that is the physiological ligand for NKG2A. As used herein, "$Qa1^b$" refers to any variant, derivative, or isoform of the $Qa1^b$ gene or encoded protein. Also encompassed are any nucleic acid or protein sequences sharing one or more biological properties or functions with wild type, full length $Qa1^b$, and sharing at least 70%, 80%, 90%, 95%, 96%, 97%, 98%, 99%, or higher nucleotide or amino acid identity.

"Autoimmune" disorders include any disorder, condition, or disease in which the immune system mounts a reaction against self cells or tissues, due to a breakdown in the ability to distinguish self from non-self or otherwise. Examples of autoimmune disorders include Hashimoto's thyroiditis, pernicious anemia, Addison's disease, type I diabetes, rheumatoid arthritis, systemic lupus erythematosus, dermatomyositis, Sjogren's syndrome, lupus erythematosus, multiple sclerosis, myasthenia gravis, Reiter's syndrome, Grave's disease, polymyositis, Guillain Barré, Wegener's granulomatosis, polyarteritis nodosa, polymyalgia rheumatica, temporal arteritis, Bechet's disease, Churg-Strauss syndrome, Takayasu's arteritis, and others. An "inflammatory disorder" includes any disorder characterized by an unwanted immune response. Autoimmune and inflammatory disorders can involve any component of the immune system, and can target any cell or tissue type in the body.

The terms "inhibiting," "reducing," "blocking," "down-modulating," and "downregulating," with respect to NKG2A activity refer to any process, method, or compound that can slow down, reduce, reverse, or in any way negatively affect the stimulation or expression of NKG2A receptors on cells, preferably NK cells. These terms can refer to compounds that inhibit the stimulation of NKG2A by a ligand, that act antagonistically in the absence of a ligand to decrease the activity of the receptor, that decrease the expression level of the receptor, that block NKG2A-triggered signaling or gene expression, or that block any other activity of the cell that results from NKG2A activation. In a preferred embodiment, the inhibiting compound or method prevents the binding of the receptor by a ligand, e.g. HLA-E. The number of NKG2A receptor molecules or any of the herein-described activities can be measured in any standard way, e.g. as disclosed elsewhere in the present application.

The term "antibody," as used herein, refers to polyclonal and monoclonal antibodies. Depending on the type of constant domain in the heavy chains, antibodies are assigned to one of five major classes: IgA, IgD, IgE, IgG, and IgM. Several of these are further divided into subclasses or isotypes, such as IgG1, IgG2, IgG3, IgG4, and the like. An exemplary immunoglobulin (antibody) structural unit comprises a tetramer. Each tetramer is composed of two identical pairs of polypeptide chains, each pair having one "light" (about 25 kDa) and one "heavy" chain (about 50-70 kDa). The N-terminus of each chain defines a variable region of about 100 to 110 or more amino acids that is primarily responsible for antigen recognition. The terms "variable light chain ($V_L$)" and "variable heavy chain ($V_H$)" refer to these light and heavy chains respectively. The heavy-chain constant domains that correspond to the different classes of immunoglobulins are termed "alpha," "delta," "epsilon," "gamma" and "mu," respectively. The subunit structures and three-dimensional configurations of different classes of immunoglobulins are well known. IgG and/or IgM are the preferred classes of antibodies employed in this invention, with IgG being particularly preferred, because they are the most common antibodies in the physiological situation and because they are most easily made in a laboratory setting.

Preferably the antibody of this invention is a monoclonal antibody. Particularly preferred are humanized, chimeric, human, or otherwise-human-suitable antibodies. The term "antibody" also includes any fragment or derivative of any of the herein described antibodies except in those contexts of the present disclosure where such inclusion causes a redundancy (e.g., a specific reference to "an antibody or a fragment thereof"). In one preferred embodiment, the antibodies are non-depleting antibodies, meaning that they bind to NK cells and inhibit NKG2A stimulation (which leads to the lysis of cells bearing HLA-E or $Qa1^b$ on their cell surface), but do not lead to the killing of the NKG2A expressing cell. Non-depleting antibodies or antibody fragments are those that are not recognized, or only poorly recognized, by Fc receptors, such as IgG4 antibodies, antibody fragments lacking the Fc portion, or any other antibody whose Fc tail has been modified to reduce or eliminate binding by Fc receptors (see, e.g., WO03101485, the entire disclosure of which is herein incorporated by reference).

In another preferred embodiment, the antibodies or antibody fragments bind to an Fc receptor. Such antibodies and fragments cause cross-linking of NKG2A molecules leading to inhibition of NK cell activity and, in some cases, to NK cell death.

The term "specifically binds to" means that an antibody can bind, preferably in a competitive binding assay, to the binding partner, e.g. NKG2A, as assessed using either recombinant forms of the protein, epitopes therein, or native proteins present on the surface of isolated NK or other cells.

Competitive binding assays and other methods for determining specific binding are further described below and are well known in the art.

A "human-suitable" antibody refers to any antibody, derivatized antibody, or antibody fragment that can be safely used in humans for, e.g. the therapeutic methods described herein. Human-suitable antibodies include all types of humanized, chimeric, or fully human antibodies, or any antibodies in which at least a portion of the antibodies is derived from humans or otherwise modified so as to avoid the immune response that is generally provoked when native non-human antibodies are used.

For the purposes of the present invention, a "humanized" antibody refers to an antibody in which the constant and variable framework region of one or more human immunoglobulins is fused with the binding region, e.g. the CDR, of an animal immunoglobulin. Such humanized antibodies are designed to maintain the binding specificity of the non-human antibody from which the binding regions are derived, but to avoid an immune reaction against the non-human antibody.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

A "human" antibody is an antibody obtained from transgenic mice or other animals that have been "engineered" to produce specific human antibodies in response to antigenic challenge (see, e.g., Green et al. (1994) Nature Genet 7:13; Lonberg et al. (1994) Nature 368:856; Taylor et al. (1994) Int Immun 6:579, the entire teachings of which are herein incorporated by reference). A fully human antibody also can be constructed by genetic or chromosomal transfection methods, as well as phage display technology, all of which are known in the art (see, e.g., McCafferty et al. (1990) Nature 348:552-553). Human antibodies may also be generated by in vitro activated B cells (see, e.g., U.S. Pat. Nos. 5,567,610 and 5,229,275, which are incorporated in their entirety by reference).

Within the context of this invention, "active" or "activated" NK cells designate biologically active NK cells, more particularly NK cells having the capacity of lysing target cells. For instance, an "active" NK cell is able to kill cells that express an NK activating receptor-ligand and fails to express "self" MHC/HLA antigens (KIR-incompatible cells). Such cells are also referred to herein as "NK cell-susceptible target cells." Examples of such target cells, which are suitable for use in redirected killing assays, are P815 and K562 cells. However, any of a number of cell types can be used and are well known in the art (see, e.g., Sivori et al. (1997) J. Exp. Med. 186: 1129-1136; Vitale et al. (1998) J. Exp. Med. 187: 2065-2072; Pessino et al. (1998) J. Exp. Med. 188: 953-960; Neri et al. (2001) Clin. Diag. Lab. Immun. 8:1131-1135). "Active" or "activated" cells can also be identified by any other property or activity known in the art as associated with NK activity, such as cytokine (e.g. IFN-γ and TNF-α) production of increases in free intracellular calcium levels. For the purposes of the present invention, activated NK cells ideally refer to NK cells in which NKG2A receptors are not stimulated, and in which an NCR, preferably NKp30, is stimulated, thereby leading to cytotoxicity of the cell against mature dendritic cells.

The term "NKG2A stimulation," as used herein refers to the process that occurs in a cell bearing NKG2A, e.g., a NK cell, when NKG2A binds to its natural ligand (e.g., HLA-E or Qa1$^b$) or a functional fragment thereof. Because NKG2A is an inhibitory receptor, such binding can cause inhibition of NK cell activity. Thus, "inhibition of NKG2A stimulation" refers to a process whereby the binding of NKG2A to its natural ligand or a functional fragment thereof is either reduced or prevented, where the binding occurs, but does not cause inhibition of NK cell activity.

Thus, the term "activating antibody," as used herein in reference to antibodies against NKG2A, is intended to mean an antibody which, through binding to NKG2A on a NK cell, prevents association of NKG2A with its natural ligand (e.g., HLA-E or Qa1$^b$) on a target cell, or prevents NKG2A dependent signal transduction normally mediated by a HLA-E positive target, and thus reverses the inhibition of lysis of the target cell by the NK cell caused by the association of NKG2A with the ligand. Thus, an activating antibody causes inhibition of NKG2A stimulation.

The term "inhibitory antibody," as used herein in reference to antibodies against NKG2A, is intended to mean an antibody which, through binding to NKG2A on a NK cell, causes inhibition of a NK cell's ability to lyse cells that would otherwise be lysed. The inhibitory antibodies of this invention typically cause cross-linking of NKG2A molecules in a NK cell, which leads to inhibition, and sometimes death, of that NK cell. It should be noted that an inhibitory antibody against NKG2A of this invention may prevent the association of NKG2A with its natural ligand or an active fragment thereof, but will not result in the lysis of a cell bearing that natural ligand because the NK cell's ability to lyse cells had been inhibited by the antibody.

The terms "isolated" "purified" or "biologically pure" refer to material that is substantially or essentially free from components which normally accompany it as found in its native state. Purity and homogeneity are typically determined using analytical chemistry techniques such as polyacrylamide gel electrophoresis or high performance liquid chromatography. A protein that is the predominant species present in a preparation is substantially purified.

The term "biological sample" as used herein includes but is not limited to a biological fluid (for example serum, lymph, blood), cell sample or tissue sample (for example bone marrow).

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "recombinant" when used with reference, e.g., to a cell, or nucleic acid, protein, or vector, indicates that the cell, nucleic acid, protein or vector has been modified by the introduction of a heterologous nucleic acid or protein or the alteration of a native nucleic acid or protein, or that the cell is derived from a cell so modified. Thus, for example, recombinant cells express genes that are not found within the native (nonrecombinant) form of the cell or express native genes that are otherwise abnormally expressed, under expressed or not expressed at all.

The term "competes with" when referring to a particular monoclonal antibody (e.g. Z199 or Z270) means that the antibody or fragment thereof being tested reduces the binding of that reference monoclonal antibody (e.g. Z199 or Z270) to NKG2A (as compared to a control comprising that reference monoclonal antibody and NKG2A, but lacking the test antibody) in a binding assay using either recombinant NKG2A molecules or surface expressed NKG2A molecules. For example, if an antibody reduces binding of Z270 to a human NKG2A molecule in a binding assay, the antibody "competes" with Z270 for binding to human NKG2A.

The term "completely competes with," as used herein means that the test antibody binds to substantially or essentially the same epitope as the reference monoclonal.

As used herein, an "effective amount" refers to any amount that is necessary or sufficient for achieving or promoting a desired outcome. In some instances an effective amount is a therapeutically effective amount. A therapeutically effective amount is any amount that is necessary or sufficient for promoting or achieving a desired biological response in a subject. The effective amount for any particular application can vary depending on such factors as the disease or condition being treated, the particular agent being administered, the size of the subject, or the severity of the disease or condition. One of ordinary skill in the art can empirically determine the effective amount of a particular agent without necessitating undue experimentation.

The term non-human primates include any mammals within the Order Primates, including apes, New World monkeys, Old World monkeys, prosimians, *Pongo pygmaeus pygmaeus* (Borneo orangutan), *Pongo pygmaeus abelii* (Sumatran orangutan), *Gorilla gorilla* (western lowland *gorilla*), *Pan paniscus* (bonobo), *Pan troglodytes* (chimpanzee), *Pan troglodytes verus* (chimpanzee), *Lemur fulvus* (brown lemur), *Saguinus fuscicollis* (white-lipped tamarin), *Saguinus labiatus* (red-bellied tamarin), *Callicebus molloch pallescens* (Paraguayan titi), *Saimiri sciureus* (squirrel monkey), *Ateles geoffroyi* (black-handed spider monkey), *Lagothrix lagotricha* (woolly monkey), *Macaca arctoides* (stumptail macaque), *Macaca fascicularis* (crab-eating macaque), *Macaca fuscata* (Japanese macaque), *Macaca mulatta* (rhesus monkey), *Macaca nemestrina* (pig-tailed macaque), *Macaca nigra* (Celebes ape), *Erythrocebus patas* (patas monkey), baboons, marmosets, capuchins, cynomolgus, howlers, spider monkeys, mandrills, guenon, patas monkeys, colobus, gibbons, lemurs, aye-ayes, loris, bushbabies, and tarsiers. In a preferred embodiment, the nonhuman primate used in the present invention is not an ape, e.g. is a nonhuman primate other than a chimpanzee, *gorilla*, orangutan, or gibbon. For the purposes of the invention, assays said to be carried out using nonhuman primates can include in vivo assays in which antibodies are administered to the primates, ex vivo assays in which, e.g. cells taken from a primate are treated with the antibodies and returned to the primate, and in vitro assays involving cells, proteins, or tissue taken from a primate.

If a mammal such as a nonhuman primate is said to "tolerate" an administration regime of an anti-NKG2A antibody, it means that the administration is not lethal and does not have any severe side effects in the animal, although side effects may be still present as long as they are not severe, and, generally, that they are outweighed by the therapeutic benefit provided by the administration.

Obtaining Compounds that Specifically Bind to NKG2A

The present invention involves both activating and inhibitory antibodies that bind to NKG2A on immune cells, preferably NK cells, as well as their identification, production, evaluation and use. One way of identifying such antibodies is to find those that are capable of binding to NKG2A. Once specifically binding antibodies are identified, they can be tested for their ability to inhibit or activate NKG2A, e.g. on NK cells. It will be appreciated, however, that carrying out such binding assays is in no way necessary for the practice of the present invention.

Any of a wide variety of assays can be used to assess binding of an antibody to NKG2A. Protocols based upon ELISAs, radioimmunoassays, Western blotting, BIACORE, and other competition assays, inter alia, are suitable for use and are well known in the art.

For example, simple binding assays can be used, in which a test antibody is incubated in the presence of a target protein or epitope (e.g., NKG2A or a portion thereof), unbound antibodies are washed off, and the presence of bound antibodies is assessed using, e.g., radiolabels, physical methods such as mass spectrometry, or direct or indirect fluorescent labels detected using, e.g., cytofluorometric analysis (e.g. FACScan). Such methods are well known to those of skill in the art. Any amount of binding above the amount seen with a control, non-specific antibody indicates that the antibody binds specifically to the target.

In such assays, the ability of the test antibody to bind to the target cell or human NKG2A can be compared with the ability of a (negative) control protein, e.g. an antibody raised against a structurally unrelated antigen, or a non-Ig peptide or protein, to bind to the same target. Antibodies or fragments that bind to the target cells or NKG2A using any suitable assay with 25%, 50%, 100%, 200%, 1000%, or higher increased affinity relative to the control protein are said to "specifically bind to" or "specifically interact with" the target, and are preferred for use in the therapeutic methods described below.

In one embodiment, the ability of a test antibody to affect the binding of a (positive) control antibody against NKG2A, e.g. 3S9, 20d5, Z270 or Z199, or derivatives thereof, is assessed. In another, the ability of a test antibody to affect the binding of a natural ligand for NKG2A, e.g. HLA-E, is measured. 3S9 is described in United States patent publication 20030095965, the disclosure of which is herein incorporated by reference. 3S9 binds to NKG2C and NKG2E, as well as to NKG2A. 20d5 is a commercially available antibody (BD Biosciences Pharmingen, Catalog No. 550518, USA). 20d5 binds to mouse NKG2A, NKG2E and NKG2C. Z199 is a commercially available antibody (Beckman Coulter, Inc., Product No. IM2750, USA). Z270 is described fully herein. Z270 binds specifically to human NKG2A, but not to human NKG2C or NKG2E.

In addition, simple competition assays may be employed in which a control antibody (e.g. 3S9, Z270 or Z199) and a test antibody are admixed (or pre-adsorbed) and applied to a sample containing NKG2A. In certain embodiments, one would pre-mix the control antibodies with varying amounts of the test antibody (e.g., 1:10 or 1:100) for a period of time prior to applying to the NKG2A-containing sample. In other embodiments, the control and varying amounts of test antibody can simply be admixed during exposure to the antigen/target sample. As long as one can distinguish bound from free antibodies (e.g., by using separation or washing techniques to eliminate unbound antibodies) and the control antibody from test antibody (e.g., by using species- or isotype-specific secondary antibodies, by specifically labeling the control antibody with a detectable label, or by using physical methods such as mass spectrometry to distinguish between different compounds) one will be able to determine if the test antibody reduces the binding of the control antibody to the antigen, indicating that the test antibody recognizes substantially the same epitope as the control.

In the above-described competition assays, the binding of the (labeled) control antibody in the presence of a completely irrelevant antibody is the control high value. The control low value is obtained by incubating the labeled (positive) control antibody (e.g. 3S9, Z270 or Z199) with unlabeled antibody of exactly the same type (e.g. 3S9, Z270 or Z199), where competition would occur and reduce binding of the labeled antibody.

In a test assay, a significant reduction in labeled antibody reactivity in the presence of a test antibody is indicative of a test antibody that recognizes the same epitope, i.e., one that "cross-reacts" with the labeled control antibody. Any test antibody or compound that reduces the binding of the labeled control to the antigen/target by at least 50% or more preferably 70%, at any ratio of control:test antibody or compound between about 1:10 and about 1:100 is considered to be an antibody or compound that binds to substantially the same epitope or determinant as the control. Preferably, such test antibody or compound will reduce the binding of the control to the antigen/target by at least 90%. Nevertheless, any compound or antibody that reduces the binding of a control antibody or compound to any measurable extent can be used in the present invention.

The identification of one or more antibodies that bind(s) to substantially the same epitope as the monoclonal antibody in question can be readily determined using any one of a variety of immunological screening assays in which antibody competition can be assessed. Such assays are routine in the art (see, e.g., U.S. Pat. No. 5,660,827, which is herein incorporated by reference). It will be understood that actually determining the epitope to which the antibody binds is not in any way required to identify an antibody that binds to the same or substantially the same epitope as the monoclonal antibody in question.

In one embodiment, competition can be assessed by a flow cytometry test. For example, cells bearing an NKG2A/CD94 receptor are incubated first with a control antibody that is known to specifically bind to the receptor (e.g., 3S9, Z270 or Z199), and then with the test antibody that has been labeled with, e.g., a fluorochrome or biotin. The test antibody is said to compete with the control if the binding obtained with preincubation with saturating amounts of control antibody is 80%, preferably, 50%, 40% or less of the binding (mean of fluorescence) obtained by the antibody without preincubation with the control. Alternatively, a test antibody is said to compete with the control if the binding obtained with a labeled control (by a fluorochrome or biotin) on cells preincubated with saturating amount of antibody to test is 80%, preferably 50%, 40%, or less of the binding obtained without preincubation with the antibody.

In one preferred example, a simple competition assay may be employed in which a test antibody is pre-adsorbed and applied at saturating concentration to a surface onto which is immobilized the substrate for the antibody binding, e.g. NKG2A/CD94 receptor, or epitope-containing portion thereof, which is known to be bound by, e.g., 3S9. The surface is preferably a BIACORE chip. The control antibody (e.g. 3S9, Z270 or Z199) is then brought into contact with the surface at a substrate-saturating concentration and the substrate surface binding of the control antibody is measured. This binding of the control antibody is compared with the binding of the control antibody to the substrate-containing surface in the absence of a test antibody. In a test assay, a significant reduction in binding of the substrate-containing surface by the control antibody in the presence of a test antibody is indicative of a test antibody that recognizes the same epitope, i.e., one that "cross-reacts" with the control antibody. Any test antibody that reduces the binding of the control antibody to the antigen-containing substrate by at least 30% or more preferably 40% is considered to be an antibody that binds to substantially the same epitope or determinant as the control antibody. Preferably, such test antibody will reduce the binding of the control antibody to the substrate by at least 50%. It will be appreciated that the order of control and test antibodies can be reversed, that is the control antibody is first bound to the surface and the test antibody is brought into contact with the surface thereafter. Preferably, the antibody having higher affinity for the substrate antigens is bound to the substrate-containing surface first since it will be expected that the decrease in binding seen for the second antibody (assuming the antibodies are cross-reacting) will be of greater magnitude. Further examples of such assays are provided in Saunal et al. (1995) J. Immunol. Meth 183: 33-41, the entire disclosure of which is herein incorporated by reference.

Preferably, monoclonal antibodies according to this invention that recognize an NKG2A will react with an epitope that is present on a substantial percentage of NK cells in patients with an autoimmune or inflammatory disorder, but will not significantly react with other cells, i.e., immune or non-immune cells that do not express NKG2A. Accordingly, once an antibody that specifically recognizes NKG2A on cells such as NK, preferably human NK cells, is identified, it can be tested for its ability to bind to NK cells taken from patients with autoimmune or inflammatory disorders. Similarly, it will be appreciated that the present methods can be practiced using multiple antibodies, e.g. directed against different epitopes or isoforms of NKG2A in a way that is designed to maximally inhibit the stimulation of NKG2A. In one embodiment, NK cells and dendritic cells are taken from a patient prior to the administration of the antibodies or compounds, and the ability of test antibodies to overcome NKG2A-mediated inhibition of lysis of the dendritic cells is assessed.

In those embodiments of the invention where specific binding or lack of specific binding to other antigens (e.g., NKG2A from other species, NKG2C, NKG2E, Fc receptor) must be measured, assays similar to those set forth above may be employed substituting the appropriate antigen for NKG2A and employing control antibodies that are specific for the antigen to which binding is being assayed. Such antigens and control antibodies are well-known in the art and many are commercially available.

Assessing the Ability of Antibodies to Inhibit NKG2A Stimulation

The identification of activating antibodies of this invention that are capable of inhibiting the stimulation of NKG2A/CD94 by HLA-E or Qa1$^b$ will generally involve cell-based assays to assess NKG2A activity in the presence of test antibody. In some embodiments, candidate antibodies will be first identified based on their ability to bind to NKG2A, as described supra. In other embodiments, cell-based screening will be performed to directly identify antibodies capable of inhibiting NKG2A stimulation, regardless of their binding affinity.

In one embodiment, modulators of NKG2A will be identified using methods or assays described in U.S. patent application no. 20030171280, Braud et al. (1998) Nature 391:795-799; Lee et al. (1998) PNAS 95:5199-5204; Vance et al. (2002) PNAS 99:868-873; Brooks et al. (1999) J Immunol 162:305-313; Miller et al. J Immunol (2003) 171:1369-75; Brooks et al. (1997) J Exp Med 185:795-800; Van Beneden et al. (2001) 4302-4311; U.S. patent application no. 20030095965; the entire disclosures of which are herein incorporated by reference.

In one embodiment, the activating antibodies of this invention are assessed for their ability to inhibit the stimulation of the NKG2A receptor by ligands. Any of a large number of assays, including molecular cell-based, and animal-based models can be used. In typical embodiments, cell-based assays will be used in which cells, e.g. NK cells expressing NKG2A, are exposed to an NKG2A ligand (or cells expressing the ligand), preferably HLA-E, and the ability of the antibody to disrupt the stimulation of the receptor is assessed.

Any of a number of cell-based assays can be used to assess NKG2A activity, including gene expression-based activities, cytotoxicity-based assays, and proliferation assays. In certain embodiments, in vitro assays will use cells, e.g. NK cells, taken from patients with an autoimmune or inflammatory disorder, but in general any NKG2A-expressing cell can be used, including NK cell lines such as YTS or NK-92 (available from the ATCC). For example, cell lines can be transfected with an NKG2A-encoding transgene and used in the present assays, so long as the stimulation of the expressed receptor alters the activity or properties of the cells in a detectable way, e.g., activates signal transduction pathways, affects proliferation, or alters the cytotoxicity of the cells. It will be appreciated that, for such assays, any isoform of NKG2A, CD94, or HLA-E (see, e.g. OMIM refs. 161555, 602894, and 143010, the entire disclosures of which are herein incorporated by reference) can be used in such assays (or any other assay or method involving NKG2A described herein).

In one preferred embodiment, a cellular assay is used in which NKG2A-expressing cells, e.g., NK cells, are incubated with an NKG2A ligand such as HLA-E, or a cell expressing an NKG2A ligand, preferably a dendritic cell, and the ability of a test compound to block the inhibition of the NK cell is assessed. In such assays, the lysis of the dendritic cells can itself be measured as a reflection of NK cell activity.

In one embodiment, cell lines will be established using NK cells from patients with an autoimmune or inflammatory disorder. In numerous embodiments, assays will be used using non-human cells or non-human NKG2A/CD94, e.g. non-human primate cells expressing NKG2A/CD94, or mouse cells expressing either mouse or human NKG2A/CD94, with the inclusion of the appropriate ligand (e.g., in the case of mouse, Qa-1).

The binding of NKG2A to the appropriate ligand causes a number of physiological changes in the cell bearing NKG2A. These include changes in gene expression, cell growth, cell proliferation, pH, intracellular second messengers, e.g., $Ca^{2+}$, IP3, cGMP, or cAMP, cytokine production, or activity such as cytotoxic activity. Such changes are referred to herein as "NKG2A activity". Any reversal of these changes in the presence of a NKG2A ligand can be used to assess the utility of a test antibody. Such reversal is referred to herein as "inhibition of NKG2A activity." In one embodiment, NKG2A activity is assessed by detecting the expression or activity of NKG2A-responsive genes or proteins, e.g., SHP-1 or SHP-2 or their targets (see, e.g., Le Drean et al. (1998) Eur J Immunol 28:264-276, Augugliaro et al. (2003) Eur J Immunol 33:1235-141; the entire disclosures of which are herein incorporated by reference).

In any of the herein-described assays, a decrease of 5%, 10%, 20%, preferably 30%, 40%, 50%, most preferably 60%, 70%, 80%, 90%, 95%, or greater reduction in any detectable measure of NKG2A activity in the cells indicates that the test antibody is a suitable candidate for use in the present methods.

In addition to binding, the ability of antibodies or compounds to cause NK cells to inhibit the proliferation or activation of, or, preferably, kill NKG2A ligand-bearing target cells, e.g. dendritic cells, certain cancer cells, or certain virally-infected cells, can be assessed. In one embodiment, human NK cells expressing the NKG2A receptor are introduced along with NKG2A ligand-bearing target cells into plates, e.g., 96-well plates, and exposed to various amounts of test antibody. By adding a vital dye, i.e. one taken up by intact cells, such as AlamarBlue (BioSource International, Camarillo, Calif.), and washing to remove excess dye, the number of viable cells can be measured by virtue of the optical density (the more cells killed by the antibody, the lower the optical density). (See, e.g., Connolly et al. (2001) J Pharm Exp Ther 298:25-33, the disclosure of which is herein incorporated by reference in its entirety).

Most preferably, the activating antibodies of this invention do not demonstrate substantial specific binding to Fc receptors. Such antibodies may comprise constant regions of various heavy chains that are known not to bind Fc receptors. One such example is an IgG4 constant region. Alternatively, antibody fragments that do not comprise constant regions, such as Fab or F(ab')2 fragments, can be used to avoid Fc receptor binding. FC receptor binding can be assessed according to methods known in the art, including for example testing binding of an antibody to Fc receptor protein in a BIACORE assay. Also, any other antibody type can be used in which the Fc portion is modified to minimize or eliminate binding to Fc receptors (see, e.g., WO03101485, the disclosure of which is herein incorporated by reference). Assays, e.g., cell based assays, to assess Fc receptor binding are well known in the art, and are described, e.g., in WO03101485.

Preferably, the activating monoclonal antibody of this invention comprises an Fc region, preferably an Fc region of the IgG4 or G2 subtype, or an Fc region of the IgG1 or G3 subtype that has been modified to reduce binding to Fc receptors. Most preferably the G4 or G2 Fc region is modified to further minimize or completely abolish binding to Fc receptors (see, e.g., Angal et al. (1993) Molecular Immunology 30:105-108, the entire disclosure of which is herein incorporated by reference.)

IgG4 isotypes are not totally devoid of Fc binding activity, showing some binding to Fc gamma ("Fcg") receptors (Newman et al. (2001) Clin. Immunol. (98(2):164-174). An unmodified IgG4 monoclonal antibody can cause cell depletion in vivo (Isaacs et al, (1996) Clin. Exp. Immunol. 106, 427). The sequence reported to be primarily responsible for the binding to Fcg receptors has been defined as LLGGPS (Burton et al, (1992) Adv. Immunol. 51:1). This sequence, located at the N terminal end (EU numbering 234-239) of the heavy chain CH2 region, is conserved in human IgG1, IgG3, and murine IgG2a isotypes, all of which bind Fcg receptors strongly. The wild-type sequence for the IgG4 isotype contains a phenylalanine at position 234, giving the motif FLGGPS. The murine IgG2b isotype, also a poor binder of Fcg receptors, contains the sequence LEGGPS. Newman et al. (2001) incorporated the glutamic acid residue associated with murine IgG2b into the human wildtype IgG4 CH2 domain to give the sequence FEGGPS which reduced even further CDC and ADCC activities and virtually eliminated binding to FcgRI and FcgRII in vitro. In addition to the introduction of glutamic acid, the replacement of serine 228 by a proline resulted in a molecule that was more stable than the wild-type IgG4. The IgG4 molecule tends to show inefficient formation of interchain disulfide bonds in the hinge region. The introduction of a proline was said to provide rigidity to the hinge and promote more efficient interchain bonding, and that the presence of a serine at position 228 might promote preferential linkage of intrachain rather than inter-chain disulfide bonds by neighboring cysteine molecules. Any such modification and others can readily be made to the antibodies of the invention.

In many instances, an inhibitory antibody of this invention can be converted to an activating antibody of this invention by abolishing most or all of the former's ability to bind an Fc receptor.

Assessing the Ability of Antibodies Against NKG2A to Inhibit NK Cell Activity

The identification of inhibitory antibodies of this invention that are capable of binding NKG2A and inhibiting NK cell activity, particularly NK cell lysis of cells is assayed using cell-based assays. Typically, a NKG2A-bearing cell, such as an NK cell, will be contacted with a NK-susceptible cell, such as RMA, a TAP-2 derivative of RMA, P815 and K562 in the presence of varying amounts of test antibody. The percentage of NK-susceptible cells killed in the presence of test antibody is compared with killing in the absence of antibody.

In another assay for an inhibitory antibody of this invention, NK cells are incubated in the presence of varying amounts of test antibody to determine that antibody's direct killing affect on NK cells as compared to NK cell death in the absence of antibody. NK cell killing may also be determined in an assay including the presence of NK-susceptible cells.

In any of the herein-described assays, a decrease of 5%, 10%, 20%, preferably 30%, 40%, 50%, most preferably 60%, 70%, 80%, 90%, or 95% of NK-susceptible cell killing and/or an increase of 5%, 10%, 20%, preferably 30%, 40%, 50%, most preferably 60%, 70%, 80%, 90%, or 95% of NK cell death indicates that the test antibody is an inhibitory antibody of this invention.

Cross-Reactivity of NKG2A Between Primate Species

It has been discovered that there is crossreactivity between human and nonhuman primate NKG2A. Thus, assays to assess the effect of an anti-NKG2A antibody on receptor activity can be carried out using an NKG2A polypeptide from any primate. For example, such assays can be performed using nonhuman primate NK cells in vitro, or the antibodies can be administered to nonhuman primates and their ability to modulate NKG2A activity, e.g. as reflected in alterations in NK cell activity, can be measured.

Producing Antibodies

The antibodies of this invention may be produced by any of a variety of techniques known in the art. Typically, they are produced by immunization of a non-human animal, preferably a mouse, with an immunogen comprising an NKG2A (or, for all embodiments described herein, for CD94, or HLA-E) receptor on the surface of cells such as T cells or NK cells or dendritic cells. The receptor may comprise entire cells or cell membranes, the full length sequence of an NKG2A (or CD94, etc.), or a fragment or derivative of any NKG2A, typically an immunogenic fragment, i.e., a portion of the polypeptide comprising an epitope exposed on the surface of cells expressing the receptor. Any isoform or splicing fragment of NKG2A can be used (see, e.g., OMIM 161555; the disclosure of which is herein incorporated by reference). Such fragments typically contain at least 7 consecutive amino acids of the mature polypeptide sequence, even more preferably at least 10 consecutive amino acids thereof. They are essentially derived from the extracellular domain of the receptor. In preferred embodiments, the NKG2A receptor used to generate antibodies is a human receptor. In certain embodiments, NKG2A present in a heterodimer, e.g. in association with CD94, can be used to generate antibodies.

In a most preferred embodiment, the immunogen comprises a wild-type human NKG2A receptor polypeptide in a lipid membrane, typically at the surface of a cell. In a specific embodiment, the immunogen comprises intact NK cells, particularly intact human NK cells, optionally treated or lysed. In a preferred embodiment, the immunogen is an NK cell taken from a patient with an autoimmune or inflammatory disorder.

In one embodiment, the antibodies are derived from one or more already-existing monoclonal antibodies that recognize NKG2A, e.g. Z199 (Della Chiesa et al, (2003) Eur. J. Immunol. 33:1657-1666), Z270, 3S9 (see, e.g., U.S. patent application no. 20030095965), or 20D5 (Vance et al, (1990) J. Exp. Med. 190(12):1801-1812), the entire disclosures of which are herein incorporated by reference). For certain applications, such antibodies can be directly or indirectly labeled (i.e., used with a labeled secondary antibody) for use as diagnostic antibodies to determine the presence of NKG2A on the presence of cells, preferably NK cells from patients with autoimmune or inflammatory disorders. In addition, the antibodies can be made suitable for human administration as described herein for use in the present therapeutic methods.

The present antibodies can be full length antibodies or antibody fragments or derivatives. Examples of antibody fragments include Fab, Fab', Fab'-SH, F(ab')$_2$, and Fv fragments; diabodies; single-chain Fv (scFv) molecules; single chain polypeptides containing only one light chain variable domain, or a fragment thereof that contains the three CDRs of the light chain variable domain, without an associated heavy chain moiety; single chain polypeptides containing only one heavy chain variable region, or a fragment thereof containing the three CDRs of the heavy chain variable region, without an associated light chain moiety; and multispecific antibodies formed from antibody fragments. Such fragments and derivatives and methods of preparing them are well known in the art. For example, pepsin can be used to digest an antibody below the disulfide linkages in the hinge region to produce F(ab')$_2$, a dimer of Fab which itself is a light chain joined to $V_H$-$C_{H1}$ by a disulfide bond. The F(ab')$_2$ may be reduced under mild conditions to break the disulfide linkage in the hinge region, thereby converting the F(ab')$_2$ dimer into an Fab' monomer. The Fab' monomer is essentially Fab with part of the hinge region (see Fundamental Immunology (Paul ed., 3d ed. 1993)). While various antibody fragments are defined in terms of the digestion of an intact antibody, one of skill will appreciate that such fragments may be synthesized de novo either chemically or by using recombinant DNA methodology.

In a preferred embodiment, the activating antibodies are non-depleting antibodies, meaning that they bind to NK cells and inhibit NKG2A stimulation, but do not lead to the killing of the NKG2A expressing cell. The ability to kill NKG2A expressing cells can be assessed using standard methods, including in vitro assays to ensure that the antibodies are not cytotoxic, directly killing bound cells, as well as in vivo assays in which the antibodies are administered and the level and activity of NKG2A expressing cells are assessed. In a particularly preferred embodiment, as described supra, antibodies will be used that are not recognized (or only poorly recognized) by Fc receptors. Accordingly, preferred antibodies include IgG4, fragments such as Fab or F(ab')2, or any other IgG, IgE, IgM, etc. of which the Fc portion has been modified to reduce or eliminate binding by Fc receptors (see, e.g., WO03101485, the entire disclosure of which is herein incorporated by reference).

The preparation of monoclonal or polyclonal antibodies is well known in the art, and any of a large number of available techniques can be used (see, e.g., Kohler & Milstein, Nature 256:495-497 (1975); Kozbor et al., Immunology Today 4: 72 (1983); Cole et al., pp. 77-96 in Monoclonal Antibodies and Cancer Therapy (1985)). Techniques for the production of single chain antibodies (U.S. Pat. No. 4,946,778) can be adapted to produce antibodies to desired polypeptides, e.g., NKG2A. Also, transgenic mice, or other organisms such as other mammals, may be used to express humanized, chimeric, or similarly-modified antibodies. Alternatively, phage display technology can be used to identify antibodies and heteromeric Fab fragments that specifically bind to selected antigens (see, e.g., McCafferty et al., Nature 348:552-554 (1990); Marks et al., Biotechnology 10:779-783 (1992)). In one embodiment, the method comprises selecting, from a library or repertoire, a monoclonal antibody or a fragment or derivative thereof that cross reacts with an NKG2A receptor polypeptide. For example, the repertoire may be any (recombinant) repertoire of antibodies or fragments thereof, optionally displayed by any suitable structure (e.g., phage, bacteria, synthetic complex, etc.).

The step of immunizing a non-human mammal with an antigen may be carried out in any manner well known in the art for (see, for example, E. Harlow and D. Lane, Antibodies: A Laboratory Manual, Cold Spring Harbor Laboratory Press, Cold Spring Harbor, N.Y. (1988)). Generally, the immunogen is suspended or dissolved in a buffer, optionally with an adjuvant, such as complete Freund's adjuvant. Methods for determining the amount of immunogen, types of buffers and amounts of adjuvant are well known to those of skill in the art and are not limiting in any way on the present invention.

Similarly, the location and frequency of immunization sufficient to stimulate the production of antibodies is also well known in the art. In a typical immunization protocol, the non-human animals are injected intraperitoneally with antigen on day 1 and again about a week later. This is followed by recall injections of the antigen around day 20, optionally with adjuvant such as incomplete Freund's adjuvant. The recall injections are performed intravenously and may be repeated for several consecutive days. This is followed by a booster injection at day 40, either intravenously or intraperitoneally, typically without adjuvant. This protocol results in the production of antigen-specific antibody-producing B cells after about 40 days. Other protocols may also be utilized as long as they result in the production of B cells expressing an antibody directed to the antigen used in immunization.

In another embodiment, lymphocytes from an unimmunized non-human mammal are isolated, grown in vitro, and then exposed to the immunogen in cell culture. The lymphocytes are then harvested and the fusion step described below is carried out.

For monoclonal antibodies, which are preferred for the purposes of the present invention, the next step is the isolation of cells, e.g., lymphocytes, splenocytes, or B cells, from the immunized non-human mammal and the subsequent fusion of those splenocytes, B cells, or lymphocytes with an immortalized cell in order to form an antibody-producing hybridoma. Accordingly, the term "preparing antibodies from an immunized animal," as used herein, includes obtaining B-cells/splenocytes/lymphocytes from an immunized animal and using those cells to produce a hybridoma that expresses antibodies, as well as obtaining antibodies directly from the serum of an immunized animal. The isolation of splenocytes, e.g., from a non-human mammal is well-known in the art and, e.g., involves removing the spleen from an anesthetized non-human mammal, cutting it into small pieces and squeezing the splenocytes from the splenic capsule and through a nylon mesh of a cell strainer into an appropriate buffer so as to produce a single cell suspension. The cells are washed, centrifuged and resuspended in a buffer that lyses any red blood cells. The solution is again centrifuged and remaining lymphocytes in the pellet are finally resuspended in fresh buffer.

Once isolated and present in single cell suspension, the antibody-producing cells are fused to an immortal cell line. This is typically a mouse myeloma cell line, although many other immortal cell lines useful for creating hybridomas are known in the art. Preferred murine myeloma lines include, but are not limited to, those derived from MOPC-21 and MPC-11 mouse tumors available from the Salk Institute Cell Distribution Center, San Diego, Calif. U.S.A., X63 Ag8653 and SP-2 cells available from the American Type Culture Collection, Rockville, Md. U.S.A. The fusion is effected using polyethylene glycol or the like. The resulting hybridomas are then grown in selective media that contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

The hybridomas can be grown on a feeder layer of macrophages. The macrophages are preferably from littermates of the non-human mammal used to isolate splenocytes and are typically primed with incomplete Freund's adjuvant or the like several days before plating the hybridomas. Fusion methods are described (e.g., in Goding, "Monoclonal Antibodies: Principles and Practice," pp. 59-103 (Academic Press, 1986), the disclosure of which is herein incorporated by reference).

The cells are allowed to grow in the selection media for sufficient time for colony formation and antibody production. This is usually between 7 and 14 days. The hybridoma colonies are then assayed for the production of antibodies that specifically recognize the desired substrate, e.g. NKG2A. The assay is typically a colorimetric ELISA-type assay, although any assay may be employed that can be adapted to the wells in which the hybridomas are grown. Other assays include immunoprecipitation and radioimmunoassay. The wells positive for the desired antibody production are examined to determine if one or more distinct colonies are present. If more than one colony is present, the cells may be recloned and grown to ensure that only a single cell has given rise to the colony producing the desired antibody. Positive wells with a single apparent colony are typically recloned and re-assayed to ensure that only one monoclonal antibody is being detected and produced.

Hybridomas that are confirmed to be producing a monoclonal antibody of this invention are then grown up in larger amounts in an appropriate medium, such as DMEM or RPMI-1640. Alternatively, the hybridoma cells can be grown in vivo as ascites tumors in an animal.

After sufficient growth to produce the desired monoclonal antibody, the growth media containing monoclonal antibody (or the ascites fluid) is separated away from the cells and the monoclonal antibody present therein is purified. Purification is typically achieved by gel electrophoresis, dialysis, chromatography using protein A or protein G-Sepharose, or an anti-mouse Ig linked to a solid support such as agarose or Sepharose beads (all described, for example, in the Antibody Purification Handbook, Amersham Biosciences, publication No. 18-1037-46, Edition AC, the disclosure of which is hereby incorporated by reference). The bound antibody is typically eluted from protein A/protein G columns by using low pH buffers (glycine or acetate buffers of pH 3.0 or less) with immediate neutralization of antibody-containing fractions. These fractions are pooled, dialyzed, and concentrated as needed.

In preferred embodiments, the DNA encoding an antibody that binds a determinant present on the NKG2A immunogen is isolated from the hybridoma and placed in an appropriate expression vector for transfection into an appropriate host. The host is then used for the recombinant production of the antibody, variants thereof, active fragments thereof, or humanized or chimeric antibodies comprising the antigen recognition portion of the antibody. Preferably, the DNA used in this embodiment encodes an antibody that recognizes a determinant present on NKG2A receptors on NK cells, such as NK cells taken from a patient with an autoimmune or inflammatory disorder.

DNA encoding the monoclonal antibodies of the invention can be readily isolated and sequenced using conventional procedures (e.g., by using oligonucleotide probes that are capable of binding specifically to genes encoding the heavy and light chains of murine antibodies). Once isolated, the DNA can be placed into expression vectors, which are then transfected into host cells such as E. coli cells, simian COS cells, Chinese hamster ovary (CHO) cells, or myeloma cells that do not otherwise produce immunoglobulin protein, to obtain the synthesis of monoclonal antibodies in the recombinant host cells. Recombinant expression in bacteria of DNA encoding the antibody is well known in the art (see, for example, Skerra et al. (1993) Curr. Op. Immunol. 5:256; and Pluckthun (1992) Immunol. Revs. 130:151). Antibodies may also be produced by selection of combinatorial libraries of immunoglobulins, as disclosed for instance in Ward et al. (1989) Nature 341:544.

In a specific embodiment, the antibody binds essentially the same epitope or determinant as one of monoclonal antibodies Z199 or Z270. In one preferred embodiment, the monoclonal antibody comprises the Fab or F(ab)$_2$ portion of Z270. According to another preferred embodiment, the monoclonal antibody comprises the three CDRs of the variable heavy chain region of Z270 (CDR1=amino acids 31 to 35 of SEQ ID NO:2; CDR2=amino acids 50 to 66 of SEQ ID NO:2; CDR3=amino acids 99-108 of SEQ ID NO:2). More preferred is a monoclonal antibody that comprises the variable heavy chain region of Z270 (Z270VH; SEQ ID NO:2). Even more preferred is a monoclonal antibody that comprises the variable heavy chain region of Z270 and is transcribed and translated from a nucleotide sequence comprising chZ270VH (SEQ ID NO:3). According to another preferred embodiment, the monoclonal antibody comprises the three CDRs of the variable light chain region of Z270 (CDR1=amino acids 24 to 34 of SEQ ID NO:6; CDR2=amino acids 50 to 56 of SEQ ID NO:6; CDR3=amino acids 89-95 of SEQ ID NO:6). More preferred is a monoclonal antibody that comprises the variable light chain region of Z270 (SEQ ID NO:6). Even more preferred is a monoclonal antibody that comprises the variable light chain region of Z270 and is transcribed and translated from a nucleotide sequence comprising chZ270VK (SEQ ID NO:7). In yet another preferred embodiment the antibody is Z270. Z270 was deposited on Dec. 22, 2005 at the Collection Nationale de Culture de Microorganismes, Institute Pasteur, 25, Rue du Docteur Roux, F-75725 Paris, France, under accession number 1-3549.

Both activating and inhibitory monoclonal antibodies against NKG2A will generally be modified so as to make them suitable for therapeutic use in humans. For example, they may be humanized, chimerized, or selected from a library of human antibodies using methods well known in the art. Such human-suitable antibodies can be used directly in the present therapeutic methods, or can be further derivatized into cytotoxic antibodies, as described infra, for use in the methods.

In one preferred embodiment, the DNA of a hybridoma producing an antibody of this invention, e.g. an antibody that binds to substantially the same epitope as Z199 or Z270, can be modified prior to insertion into an expression vector, for example, by substituting the coding sequence for human heavy- and light-chain constant domains in place of the homologous non-human sequences (e.g., Morrison et al. (1984) PNAS 81:6851), or by covalently joining to the immunoglobulin coding sequence all or part of the coding sequence for a non-immunoglobulin polypeptide. In that manner, "chimeric" or "hybrid" antibodies are prepared that have the binding specificity of the original antibody. Typically, such non-immunoglobulin polypeptides are substituted for the constant domains of an antibody of the invention.

In a preferred embodiment, the antibody comprises the variable heavy chain region of Z270 fused (SEQ ID NO:2) to a human heavy chain constant region. In one preferred embodiment, the human heavy chain constant region is a IgG4 constant region. In another preferred embodiment, the human heavy chain constant region is a IgG1 constant region, preferably a human IgG1m(-1, -2, -3) constant region. Preferably, such a human heavy chain constant region-containing antibody is transcribed and translated from a nucleotide sequence comprising chZ270VH (SEQ ID NO:3).

In another preferred embodiment, the antibody comprises the variable light chain region of Z270 fused (SEQ ID NO:6) to a human light chain constant region. More preferred is an antibody that comprises the variable light chain region of Z270 fused to the human kappa (k3) light chain constant region. Preferably, such a human light chain constant region-containing antibody is transcribed and translated from a nucleotide sequence comprising chZ270VK (SEQ ID NO:7).

Even more preferred is an antibody comprising both 270VK fused to a human light chain constant region and 270VK fused to a human heavy chain constant region. Preferably, the light chain constant region is a kappa (k3) constant region and the heavy chain constant region is selected from IgG4 or IgG1m(-1, -2, -3). Also, preferably, each of the heavy and light chains of the antibody are transcribed from a nucleotide sequence comprising chZ270VH (SEQ ID NO:3) and a nucleotide sequence comprising chZ270VK (SEQ ID NO:7), respectively.

In one particularly preferred embodiment, the antibody of this invention is humanized. "Humanized" forms of antibodies according to this invention are specific chimeric immunoglobulins, immunoglobulin chains or fragments thereof (such as Fv, Fab, Fab', F(ab')$_2$, or other antigen-binding subsequences of antibodies) which contain minimal sequence derived from the murine or other non-human immunoglobulin. For the most part, humanized antibodies are human immunoglobulins (recipient antibody) in which residues from a complementary-determining region (CDR) of the recipient are replaced by residues from a CDR of the original antibody (donor antibody) while maintaining the desired specificity, affinity, and capacity of the original antibody. In some instances, Fv framework residues of the human immunoglobulin may be replaced by corresponding non-human residues. Furthermore, humanized antibodies can comprise residues that are not found in either the recipient antibody or in the imported CDR or framework sequences. These modifications are made to further refine and optimize antibody performance. In general, the humanized antibody will comprise substantially all of at least one, and typically two, variable domains, in which all or substantially all of the CDR regions correspond to those of the original antibody and all or substantially all of the FR regions are those of a human immunoglobulin consensus sequence. For further details see Jones et al. (1986) Nature 321: 522; Reichmann et al. (1988) Nature 332: 323; Verhoeyen et al. (1988) Science 239:1534 (1988); Presta (1992) Curr. Op. Struct. Biol. 2:593; each of which is herein incorporated by reference in its entirety.

The choice of human variable domains, both light and heavy, to be used in making the humanized antibodies is very important to reduce antigenicity. According to the so-called "best-fit" method, the sequence of the variable domain of an antibody of this invention is screened against the entire library of known human variable-domain sequences. The human sequence which is closest to that of the mouse is then accepted as the human framework (FR) for the humanized antibody (Sims et al. (1993) J. Immun., 151:2296; Chothia and Lesk (1987) J. Mol. Biol. 196:901). Another method uses a particular framework from the consensus sequence of all human antibodies of a particular subgroup of light or heavy chains. The same framework can be used for several different humanized antibodies (Carter et al. (1992) PNAS 89:4285; Presta et al. (1993) J. Immunol. 51:1993)).

It is further important that antibodies be humanized while retaining their high affinity for NKG2A, preferably human and non-human primate NKG2A, and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequences so that the desired antibody characteristic, such as increased affinity for the target antigen(s), is achieved. In general, the CDR residues are directly and most substantially involved in influencing antigen binding.

In preferred examples, the invention provides human or humanized activating anti-NKG2A antibodies having a half-life of at least 5, 6, 8, 9, 10, 15 or 20 days, which do not substantially bind human FcgammaRIIIa (CD16). More preferably, the activating anti-NKG2A antibody is a humanized antibody and completely competes with a Z199 or Z270 antibody for binding to human NKG2A. For the purpose of illustration with preferred antibodies suitable for use according to the methods herein, a Z199 or Z270 antibody can be used to prepare a humanized antibody. Preferred humanized antibodies according to the invention comprise a human framework, at least one CDR from a non-human antibody, and in which any constant region present is substantially identical to a human immunoglobulin constant region, e.g., at least about 60-90%, preferably at least 95% identical. Hence, all parts of a humanized antibody, except possibly the CDR's, are substantially identical to corresponding parts of one or more native human antibody sequences. In some instances, the humanized antibody, in addition to CDRs from a non-human antibody, would include additional non-human residues in the human framework region.

The design of humanized antibodies can be carried out as follows. When an amino acid falls under the following categories, the framework amino acid of a human antibody to be used (acceptor antibody) is replaced by a framework amino acid from a CDR-providing non-human antibody (donor antibody): (a) the amino acid in the human framework region of the acceptor antibody is unusual for human antibody at that position, whereas the corresponding amino acid in the donor antibody is typical for human antibody in that position; (b) the position of the amino acid is immediately adjacent to one of the CDR's; or (c) the amino acid is capable of interacting with the CDR's in a tertiary structure antibody model (see, C. Queen et al. Proc. Natl. Acad. Sci. USA 86, 10029 (1989), and Co et al., Proc. Natl. Acad. Sci. USA 88, 2869 (1991) the disclosures of which are incorporated herein by reference).

For further detailed description of the production of humanized antibody, See Queen et al., op. cit. and Co et al, op. cit. and U.S. Pat. Nos. 5,585,089; 5,693,762, 5,693,761, and 5,530,101, the disclosures of which are incorporated herein by reference. Usually, the CDR regions in humanized antibodies are substantially identical, and more usually, identical to the corresponding CDR regions in the mouse antibody from which they were derived. Although not usually desirable, it is sometimes possible to make one or more conservative amino acid substitutions of CDR residues without appreciably affecting the binding affinity of the resulting humanized antibody. Occasionally, substitutions of CDR regions can enhance binding affinity. Other than for the specific amino acid substitutions discussed above, the framework regions of humanized antibodies are usually substantially identical, and more usually, identical to the framework regions of the human antibodies from which they were derived. Of course, many of the amino acids in the framework region make little or no direct contribution to the specificity or affinity of an antibody. Thus, many individual conservative substitutions of framework residues can be tolerated without appreciable change of the specificity or affinity of the resulting humanized antibody. The antigen binding region of the humanized antibody (the non-human portion) can be derived from an antibody of nonhuman origin, referred to as a donor antibody, having specificity for NKG2A. For example, a suitable antigen binding region can be derived from Z199 or Z270 monoclonal antibodies. Other sources include NKG2A-specific (blocking) antibodies obtained from nonhuman sources, such as rodent (e.g., mouse and rat), rabbit, pig, goat or non-human primate (e.g., monkey) or camelid animals (e.g., camels and llamas). Additionally, other polyclonal or monoclonal antibodies, such as antibodies which bind to the same or similar epitope as Z199 or Z270 antibodies, can be made (e.g., Kohler et al., Nature, 256:495-497 (1975); Harlow et al., 1988, Antibodies: A Laboratory Manual (Cold Spring Harbor, N.Y.); and Current Protocols in Molecular Biology, Vol. 2 (Supplement 27, Summer '94), Ausubel et al., Eds. (John Wiley & Sons: New York, N.Y.), Chapter 11 (1991)).

In one embodiment, the humanized antibody having binding specificity for human and non-human primate NKG2A comprises at least one CDR of nonhuman origin. For example, a humanized antibody having a binding specificity for human and non-human primate NKG2A comprises a heavy chain and a light chain. The light chain can comprise a CDR derived from an antibody of nonhuman origin which binds NKG2A and a FR derived from a light chain of human origin. For example, the light chain can comprise CDR1, CDR2 and/or CDR3 which have the amino acid sequence similar or substantially the same as that of the respective CDR of any one of the Z199 or Z270 antibodies such that the antibody specifically binds to the human and non-human primate NKG2A. The heavy chain can comprise a CDR derived from an antibody of nonhuman origin which binds NKG2A and a FR derived from a heavy chain of human origin. For example, the heavy chain can comprise CDR1, CDR2 and CDR3 which have the amino acid sequence set forth below or an amino acid similar or substantially the same as that of the respective CDR of the Z199 or Z270 antibodies such that the antibody specifically binds to the human and non-human primate NKG2A.

An embodiment of the invention is a humanized antibody which specifically binds to human and non-human primate NKG2A and comprises a humanized light chain comprising three light chain CDRs from a Z199 or Z270 antibody and a light chain variable region framework sequence from a human antibody light chain. The invention further comprises a humanized heavy chain that comprises three heavy chain CDRs from a Z199 or Z270 antibody and a heavy chain variable region framework sequence from a human antibody heavy chain.

The portion of the humanized antibody or antibody chain which is of human origin (the human portion) can be derived from any suitable human antibody or antibody chain. For example, a human constant region or portion thereof, if present, can be derived from the kappa or lambda light chains, and/or the gamma (e.g., gamma1, gamma2, gamma3, gamma4), μ, alpha (e.g., alpha1, alpha2), delta or epsilon heavy chains of human antibodies, including allelic variants. A particular constant region, such as IgG2b or IgG4, variants or portions thereof can be selected to tailor effector function. The latter constant regions, or portions thereof are particularly preferred in that they do not substantially bind FcgammaIIIa receptor on NK cells (CD16) and therefore do not substantially induce ADCC mediated lysis of NK effectors to which the anti-NKG2A antibodies of the invention are bound. For example, a mutated constant region, also referred to as a "variant," can be incorporated into a fusion protein to minimize binding to Fc receptors and/or ability to fix complement (see e.g., Winter et al., U.S. Pat. No. 5,648,260; Morrison et al., WO 89/07142; Morgan et al., WO 94/29351). In addition, a mutated IgG2 Fc domain can be created that reduces the mitogenic response, as compared to natural Fc regions (see e.g., Tso et al., U.S. Pat. No. 5,834,597, the teachings of which are incorporated by reference herein in their entirety). If present, human FRs are preferably derived from a human antibody variable region having sequence similarity to the analogous or equivalent region of the antigen binding region donor. Other sources of FRs for portions of human origin of a humanized antibody include human variable consensus sequences (see, Kettleborough, C. A. et al., Protein Engineering 4:773-783 (1991); Queen et al., U.S. Pat. Nos. 5,585,089, 5,693,762 and 5,693,761, the teachings of all of which are incorporated by reference herein in their entirety). For example, the sequence of the antibody or variable region used to obtain the nonhuman portion can be compared to human sequences as described in Kabat, E. A., et al., Sequences of Proteins of Immunological Interest, Fifth Edition, U.S. Department of Health and Human Services, U.S. Government Printing Office (1991). In a preferred embodiment, the FRs of a humanized antibody chain are derived from a human variable region having at least about 60% overall sequence identity, and preferably at least about 80% overall sequence identity, with the variable region of the nonhuman donor (e.g., Z199 or Z270 antibody).

The phrase "substantially identical," in context of two nucleic acids or polypeptides (e.g., DNAs encoding a humanized antibody or the amino acid sequence of the humanized antibody) refers to two or more sequences or subsequences that have at least about 80%, most preferably 90-95% or higher nucleotide or amino acid residue identity, when compared and aligned for maximum correspondence, as measured using the following sequence comparison method and/or by visual inspection. Such "substantially identical" sequences are typically considered to be homologous. Preferably, the "substantial identity" exists over a region of the sequences that is at least about 50 residues in length, more preferably over a region of at least about 100 residues, and most preferably the sequences are substantially identical over at least about 150 residues, or over the full length of the two sequences to be compared. As described below, any two antibody sequences can only be aligned in one way, by using the numbering scheme in Kabat. Therefore, for antibodies, percent identity has a unique and well-defined meaning.

Amino acids from the variable regions of the mature heavy and light chains of antibodies are designated Hx and Lx respectively, where x is a number designating the position of an amino acid according to the scheme of Kabat, Sequences of Proteins of Immunological Interest (National Institutes of Health, Bethesda, Md., 1987 and 1991). Kabat lists many amino acid sequences for antibodies for each subgroup, and lists the most commonly occurring amino acid for each residue position in that subgroup. Kabat uses a method for assigning a residue number to each amino acid in a listed sequence, and this method for assigning residue numbers has become standard in the field. Kabat's scheme is extendible to other antibodies not included in his compendium by aligning the antibody in question with one of the consensus sequences in Kabat. The use of the Kabat numbering system readily identifies amino acids at equivalent positions in different antibodies. For example, an amino acid at the L50 position of a human antibody occupies the equivalent position to an amino acid position L50 of a mouse antibody. From N-terminal to C-terminal, both light and heavy chain variable regions comprise alternating framework and (CDRs): FR1, CDR1, FR2, CDR2, FR3, CDR3 and FR4. The assignment of amino acids to each region is in accordance with the definitions of Kabat (1987) and (1991), supra and/or Chothia & Lesk, J. Mol. Biol. 196:901-917 (1987); Chothia et al., Nature 342:878-883 (1989).

Binding and/or adhesion assays or other suitable methods can also be used in procedures for the identification and/or isolation of humanized antibodies (e.g., from a library) with the requisite specificity (competition assays for example).

The antibody portions of nonhuman and human origin for use in the invention include light chains, heavy chains and portions of light and heavy chains. These antibody portions can be obtained or derived from antibodies (e.g., by de novo synthesis of a portion), or nucleic acids encoding an antibody or chain thereof having the desired property (e.g., binds NKG2A, sequence similarity, for example with the Z199 or Z270 antibody) can be produced and expressed. Humanized antibodies comprising the desired portions (e.g., antigen binding region, CDR, FR, C region) of human and nonhuman origin can be produced using synthetic and/or recombinant nucleic acids to prepare genes (e.g., cDNA) encoding the desired humanized chain. To prepare a portion of a chain, one or more stop codons can be introduced at the desired position. For example, nucleic acid sequences coding for newly designed humanized variable regions can be constructed using PCR mutagenesis methods to alter existing DNA sequences (see e.g., Kamman, M., et al., Nucl. Acids Res. 17:5404 (1989)). PCR primers coding for the new CDRs can be hybridized to a DNA template of a previously humanized variable region which is based on the same, or a very similar, human variable region (Sato, K., et al., Cancer Research 53:851-856 (1993)). If a similar DNA sequence is not available for use as a template, a nucleic acid comprising a sequence encoding a variable region sequence can be constructed from synthetic oligonucleotides (see e.g., Kolbinger, F., Protein Engineering 8:971-980 (1993)). A sequence encoding a signal peptide can also be incorporated into the nucleic acid (e.g., on synthesis, upon insertion into a vector). If the natural signal peptide sequence is unavailable, a signal peptide sequence from another antibody can be used (see, e.g., Kettleborough, C. A., Protein Engineering 4:773-783 (1991)). Using these methods, methods described herein or other suitable methods, variants can be readily produced. In one embodiment, cloned variable regions can be mutagenized, and sequences encoding variants with the desired specificity can be selected (e.g., from a phage library; see e.g., Krebber et al., U.S. Pat. No. 5,514,548; Hoogengoom et al., WO 93/06213, published Apr. 1, 1993)).

The invention also relates to isolated and/or recombinant (including, e.g., essentially pure) nucleic acids comprising sequences which encode a humanized antibody or humanized antibody light or heavy chain of the present invention.

Human antibodies may also be produced according to various other techniques, such as by using, for immunization, other transgenic animals that have been engineered to express a human antibody repertoire. In this technique, elements of the human heavy and light chain loci are introduced into mice or other animals with targeted disruptions of the endogenous heavy chain and light chain loci (see, e.g., Jakobovitz et al. (1993) Nature 362:255; Green et al. (1994) Nature Genet. 7:13; Lonberg et al. (1994) Nature 368:856; Taylor et al. (1994) Int. Immun. 6:579, the entire disclosures of which are herein incorporated by reference). Alternatively, human antibodies can be constructed by genetic or chromosomal transfection methods, or through the selection of antibody repertoires using phage display methods. In this technique, antibody variable domain genes are cloned in-frame into either a major or minor coat protein gene of a filamentous bacteriophage, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. In this way, the phage mimics some of the properties of the B cell (see, e.g., Johnson et al. (1993) Curr Op Struct Biol 3:5564-571; McCafferty et al. (1990) Nature 348:552-553, the entire disclosures of which are herein incorporated by reference). Human antibodies may also be generated by in vitro activated B cells (see, e.g., U.S. Pat. Nos. 5,567,610 and 5,229,275, the disclosures of which are incorporated in their entirety by reference).

In one embodiment, "humanized" monoclonal antibodies are made using an animal such as a XenoMouse® (Abgenix, Fremont, Calif.) for immunization. A XenoMouse is a murine host that has had its immunoglobulin genes replaced by functional human immunoglobulin genes. Thus, antibodies produced by this mouse or in hybridomas made from the B cells of this mouse are already humanized. The XenoMouse is described in U.S. Pat. No. 6,162,963, which is herein incorporated in its entirety by reference. An analogous method can be achieved using a HuMAb-Mouse™ (Medarex).

The antibodies of the present invention may also be derivatized to "chimeric" antibodies (immunoglobulins) in which a portion of the heavy and/or light chain is identical with or homologous to corresponding sequences in the original antibody, while the remainder of the chain(s) is identical with or homologous to corresponding sequences in antibodies derived from another species or belonging to another antibody class or subclass, as well as fragments of such antibodies, so long as they exhibit the desired biological activity (see, e.g., Morrison et al. (1984) PNAS 81:6851; U.S. Pat. No. 4,816,567).

In another embodiment the invention provides any of the antibodies or fragments thereof described above (whether activating or inhibitory) conjugated to a cytotoxic agent. The term "cytotoxic agent" as used herein is a molecule that is capable of killing a cell bearing a NKG2A receptor on its cell surface. The term "conjugated" as used herein means that the two agents are either bound to each other through a covalent and/or non-covalent bond, or tethered or otherwise connected to one another directly or through a linking moiety.

Any of a large number of toxic moieties or strategies can be used to produce such cytotoxic antibody conjugates. In certain preferred embodiments, the antibodies will be directly derivatized with radioisotopes or other toxic compounds. In such cases, the labeled monospecific anti-NKG2A antibody can be injected into the patient, where it can then bind to and kill cells expressing that target antigen, particularly NK cells, with unbound antibody simply clearing the body. Indirect strategies can also be used, such as the "Affinity Enhancement System" (AES) (see, e.g., U.S. Pat. No. 5,256,395; Barbet et al. (1999) Cancer Biother Radiopharm 14:153-166; the entire disclosures of which are herein incorporated by reference). This particular approach involves the use of a radiolabeled hapten and an antibody that recognizes both the NK cell receptor and the radioactive hapten. In this case, the antibody is first injected into the patient and allowed to bind to target cells, and then, once unbound antibody is allowed to clear from the blood stream, the radiolabeled hapten is administered. The hapten binds to the antibody-antigen complex on the overproliferating LGL (e.g. NK or T) cells, thereby killing them, with the unbound hapten clearing the body. Any type of moiety with a cytotoxic or cytoinhibitory effect can be conjugated to the present antibodies to form a cytotoxic conjugate of the present invention and to inhibit or kill specific NK receptor expressing cells, including radioisotopes, toxic proteins, toxic small molecules, such as drugs, toxins, immunomodulators, hormones, hormone antagonists, enzymes, oligonucleotides, enzyme inhibitors, therapeutic radionuclides, angiogenesis inhibitors, chemotherapeutic drugs, vinca alkaloids, anthracyclines, epidophyllotoxins, taxanes, antimetabolites, alkylating agents, antibiotics, COX-2 inhibitors, SN-38, antimitotics, antiangiogenic and apoptotoic agents, particularly doxorubicin, methotrexate, taxol, CPT-11, camptothecans, nitrogen mustards, gemcitabine, alkyl sulfonates, nitrosoureas, triazenes, folic acid analogs, pyrimidine analogs, purine analogs, platinum coordination complexes, *Pseudomonas* exotoxin, ricin, abrin, 5-fluorouridine, ribonuclease (RNase), DNase I, Staphylococcal enterotoxin-A, pokeweed antiviral protein, gelonin, diphtherin toxin, *Pseudomonas* exotoxin, and *Pseudomonas* endotoxin and others (see, e.g., Remington's Pharmaceutical Sciences, 19th Ed. (Mack Publishing Co. 1995); Goodman and Gilman's The Pharmacological Basis of Therapeutics (McGraw Hill, 2001); Pastan et al. (1986) Cell 47:641; Goldenberg (1994) Cancer Journal for Clinicians 44:43; U.S. Pat. No. 6,077,499; the entire disclosures of which are herein incorporated by reference). It will be appreciated that a toxin can be of animal, plant, fungal, or microbial origin, or can be created de novo by chemical synthesis.

The toxins or other compounds can be linked to the antibody directly or indirectly, using any of a large number of available methods. For example, an agent can be attached at the hinge region of the reduced antibody component via disulfide bond formation, using cross-linkers such as N-succinyl 3-(2-pyridyldithio)proprionate (SPDP), or via a carbohydrate moiety in the Fc region of the antibody (see, e.g., Yu et al. (1994) Int. J. Cancer 56: 244; Wong, Chemistry of Protein Conjugation and Cross-linking (CRC Press 1991); Upeslacis et al., "Modification of Antibodies by Chemical Methods," in Monoclonal antibodies: principles and applications, Birch et al. (eds.), pages 187-230 (Wiley-Liss, Inc. 1995); Price, "Production and Characterization of Synthetic Peptide-Derived Antibodies," in Monoclonal antibodies: Production, engineering and clinical application, Ritter et al. (eds.), pages 60-84 (Cambridge University Press 1995), Cattel et al. (1989) Chemistry today 7:51-58, Delprino et al. (1993) J. Pharm. Sci 82:699-704; Arpicco et al. (1997) Bioconjugate Chemistry 8:3; Reisfeld et al. (1989) Antibody, Immunicon. Radiopharrn. 2:217; the entire disclosures of each of which are herein incorporated by reference).

In one preferred embodiment, the antibody will be derivatized with a radioactive isotope, such as 1-131. Any of a number of suitable radioactive isotopes can be used, including, but not limited to, Indium-111, Lutetium-171, Bismuth-212, Bismuth-213, Astatine-211, Copper-62, Copper-64, Copper-67, Yttrium-90, Iodine-125, Iodine-131, Phosphorus-32, Phosphorus-33, Scandium-47, Silver-111, Gallium-67, Praseodymium-142, Samarium-153, Terbium-161, Dysprosium-166, Holmium-166, Rhenium-186, Rhenium-188, Rhenium-189, Lead-212, Radium-223, Actinium-225, Iron-59, Selenium-75, Arsenic-77, Strontium-89, Molybdenum-99, Rhodium-105, Palladium-109, Praseodymium-143, Promethium-149, Erbium-169, Iridium-194, Gold-198, Gold-199, and Lead-211. In general, the radionuclide preferably has a decay energy in the range of 20 to 6,000 keV, preferably in the ranges 60 to 200 keV for an Auger emitter, 100-2,500 keV for a beta emitter, and 4,000-6,000 keV for an alpha emitter. Also preferred are radionuclides that substantially decay with generation of alpha-particles.

In selecting a cytotoxic moiety for conjugation to the anti-NKG2A antibody in the present cytotoxic compositions, it is desirable to ensure that the moiety will not exert significant in vivo side effects against life-sustaining normal tissues, such as one or more tissues selected from heart, kidney, brain, liver, bone marrow, colon, breast, prostate, thyroid, gall bladder, lung, adrenals, muscle, nerve fibers, pancreas, skin, or other life-sustaining organ or tissue in the human body. The term "significant side effects", as used herein, refers to an antibody, ligand or antibody conjugate, that, when administered in vivo, will produce only negligible or clinically manageable side effects, such as those normally encountered during chemotherapy.

In a somewhat related embodiment, the invention also provides an antibody of this invention conjugated to a detectable marker. The term "detectable marker" as used herein refers to any molecule that can be quantitatively or qualitatively observed or measured. Examples of detectable markers useful in the conjugated antibodies of this invention are radioisotopes, fluorescent dyes, or a member of a complementary binding pair, such as a member of any one of: an antigen/antibody (other than an antibody to NKG2A); lectin/carbohydrate; avidin/biotin; receptor/ligand; or molecularly imprinted polymer/print molecule systems.

The detectable marker conjugated antibodies of this invention may be used to detect the binding of the antibody to NKG2A, either in vitro or in vivo. Such conjugates may also be utilized to detect the binding of another molecule to NKG2A in a competition-type experiment. In an in vivo setting, the detectable marker-antibody conjugate of this invention may be used to monitor the efficacy of treatment of a patient with a NKG2A antibody composition of this invention, by ex vivo detection of the detectable marker (e.g., via whole body scans or the like) or by detection in a biological material (e.g., blood, biopsied tissue, other bodily fluids, skin scrapings, etc.) obtained from the patient. The detection of the marker in various biological material will be correlated with the presence of the therapeutic antibody in said material.

In a related embodiment the invention provides a kit comprising, in separate vessels: a detectable marker-anti-NKG2A antibody conjugate; and an NKG2A-containing material. An NKG2A-containing material may be isolated NKG2A, a fragment of NKG2A comprising an epitope to which an anti-NKG2A antibody of this invention binds, or a cell that expresses NKG2A on its cell surface.

Evaluation of Anti-Human NKG2A Antibodies in Nonhuman Primates

In a preferred series of embodiments, the activity of an anti-NKG2A antibody of this invention will be assessed in vivo in a nonhuman primate. Such embodiments can be carried out for any of a wide variety of reasons. In view of the crossreactivity between human NKG2A and NKG2A from nonhuman primates, and in view of the physiological similarities among primates, administering antibodies that recognize human NKG2A to nonhuman primates allows the antibodies to be assessed in vivo for many aspects including, but not limited to, ability to modulate the activity of cells expressing NKG2A (e.g. NK cells), side effects produced, toxicity, pharmacodynamics, pharmacokinetics, bioavailability, half-life, optimal dose or frequency of administration, optimal formulations including combinations with other therapeutic agents, or any other property that may be measured to determine the efficacy, safety, or optimal administration of the antibodies. Methods of assessing candidate therapeutic compounds in vivo are well known in the art, and are described, e.g., in The Merck Manual of Diagnosis and Therapy, $17^{th}$ edition, Remington's Pharmaceutical Sciences, $20^{th}$ edition, the entire disclosures of which are herein incorporated by reference. Any nonhuman primate can be used for the herein-described methods, including apes, monkeys, and prosimians. Preferred primates include the Rhesus monkey (*Macacus mulatta*), African green monkey (*Chlorocebus aethiops*), Marmoset (*Callithrix jacchus*), Saïmiri (*Saimiri sciureus*), cynomolgus, and Baboon (*Papio hama-*

*dryas*). In another preferred embodiment, the primate is not an ape, e.g. is a primate other than a chimpanzee. Nonhuman primates are commonly used in safety and efficacy assays for candidate human therapeutic agents, and their care, administration, biology, and other relevant features are well known to those in the art. In one embodiment, prior to the administration of any antibody to any nonhuman primate (or the use of tissue, cells, or proteins from a nonhuman primate in any assay), the crossreactivity of the candidate anti-human NKG2A antibodies with NKG2A from the nonhuman primate will be confirmed.

In certain embodiments, the nonhuman primates will serve as a model for a disease or condition that could be treated by an NKG2A-modulating compound. For example, models of autoimmune disorders, allergies, cancers, or infectious diseases can be used, e.g. to assess the ability of the antibodies to treat or alleviate the symptoms of the diseases or conditions. While in no way limiting for the practice of the present invention, certain nonhuman primates are particularly useful for studying particular types of diseases or conditions. For example, marmosets have served as model animals for the study of immunity and of cardiovascular diseases, *saimiri* for the study of infectious diseases, macaques (including rhesus monkeys) for the study of pharmacology and toxicology of specific compounds, and baboons as a model for surgical studies, transplants, and biomaterials.

In one embodiment, anti-NKG2A antibodies are administered to a nonhuman primate to assess the efficacy of the antibodies in binding to and/or modulating NKG2A activity. In such embodiments, the antibodies can be administered in any dose, frequency, or formulation, and indeed such factors can be varied to assess their relative influence over the efficacy. Efficacy of the antibodies can be assessed in any of a large variety of ways. For example, one can assess the in vivo binding of the antibodies to NKG2A or to NKG2A-expressing cells, the in vivo effect of the antibodies on the expression of NKG2A on cells, e.g. NK cells, or the in vivo influence of the antibodies on the activity of NKG2A, e.g. as measured using any of the herein-described assays for NK cell activity. In such embodiments, an antibody is typically administered to a nonhuman primate and its effects detected, e.g., on biological samples obtained from the nonhuman primate. Alternatively, certain methods can be carried out in vitro, where the effects of the antibodies on, e.g., NKG2A-expressing cells obtained from a nonhuman primate are examined.

To assess the binding of the anti-human NKG2A antibodies, the antibodies can be directly or indirectly labeled. For example, the antibody can be labeled with a radioisotope prior to administration, and its localization within the animal assessed by examining various biological samples (e.g., blood, various tissues or organs, immune-related tissues such as bone marrow, spleen, lymphatic system components, or others) obtained at different times after administration. In one preferred embodiment, PBLs are obtained, and the binding of the antibodies to NK cells is determined using, e.g., fluorescently labeled secondary antibodies, with bound antibodies detected, e.g., by FACS analysis.

Similarly, antibodies can be administered to a nonhuman primate and their effect on NKG2A activity assessed. For example, NK cells can be obtained prior and subsequent to administration of an anti-NKG2A antibody, and the activity, expression of NKG2A, and/or number of the two (or more) sets of cells assessed using any standard method. Activating antibodies of this invention that block NKG2A stimulation (and thereby block inhibition of NK cells through the receptor) would be expected to increase NK cell activity. Inhibitory antibodies of this invention that cross-link NKG2A receptors would be expected to decrease NK cell activity and decrease the number of viable NK cells. Both types of antibodies that cause altered NK cell activity in the nonhuman primate would be considered suitable for use in treating disorders in humans where an increase or a decrease in NK cell activity is desirable.

In another set of embodiments, anti-NKG2A antibodies are administered to a nonhuman primate in order to assess the safety of the antibodies, as well as their various pharmacokinetic and pharmacodynamic properties. Safety can be assessed in any of a large variety of ways. For example, the overall toxicity of the antibodies can be assessed, by determining the median lethal dose (LD50), typically expressed as milligram per kilogram (mg/kg), in which the value 50 refers to the percentage death among the animals under study. In addition to determining the LD50, safety can also be assessed by monitoring the animals for any detectable responses to the administration, including behavioral, physical, or physiological changes as evidenced by heart rate, blood pressure, etc. Responses can also involve blood and other laboratory based tests to examine markers indicative of organ function, such as creatine or BUN for renal function, prothrombin, bilirubin, albumin, or various enzymes to determine hepatic function, or others (see, e.g., The Merck Manual of Diagnosis and Therapy, $17^{th}$ edition, herein incorporated by reference).

Methods for in vivo pharmacokinetic and pharmacodynamic assessment of the antibodies are standard and well known in the art (see, e.g., He et al. (1998) J. Immunol. 160:1029-1035; Alyanakian et al. (2003) Vox Sanguinis 84:188-192, Sharma et al. (2000) WET 293:33-41, the entire disclosures of which are herein incorporated by reference). Such assays would typically involve administering anti-NKG2A antibodies to a nonhuman primate and, at various times after administration, examining the level (in plasma and other tissues), distribution, binding, stability, and other properties of the antibodies. Such assays are critical components of pre-clinical studies and, by determining the in vivo half life, distribution, bioavailability, etc. of the antibodies, help determine the therapeutic window and thus proper administration regimens (e.g. frequency and dose of administration) that will allow optimal targeting of NK expressing cells by the administered antibodies.

In conjunction with studies of the efficacy, safety, pharmacodynamics and pharmacokinetics of anti-NKG2A antibodies, a variety of formulations and administration regimens can also be systematically tested to obtain optimal efficacy and safety for anti-human NKG2A antibodies. For example, the therapeutic window (the range of plasma concentrations of the antibodies that have a high probability of therapeutic success) can be determined, as well as those regimens and formulations that are optimally safe and effective in targeting NKG2A and modulating NK cell activity in vivo. For example, a given antibody can be administered every 1, 2, 3, 4, 5, or 6 days, or every 1, 2, 3, or 4 weeks, etc., and the safety, efficacy, kinetic, etc. parameters examined. Similarly, the dose of the antibody administered at any one time can be varied and the same parameters examined, or any combination of dose and frequency of administration can be tested. Further, different formulations, e.g., compositions including different excipients, different combinations of anti-NKG2A antibodies, or different combinations of NKG2A antibodies with other therapeutic agents (depending on the condition that would be treated, e.g. a chemotherapeutic agent to treat cancer) can be tested in nonhuman primates. Also, different routes of administration, e.g. intravenous, pulmonary, topical, etc., can be compared. Such methods of varying administration parameters are well known to those of skill in the art.

Pharmaceutical Compositions

The invention also provides compositions, e.g., pharmaceutical compositions, that comprise any of the present antibodies, including fragments and derivatives thereof, in any suitable vehicle in an effective amount and a pharmaceutically acceptable carrier.

Pharmaceutically acceptable carriers that may be used in these compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers and wool fat.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. For localized disorders such as RA, the compositions will often be administered topically, e.g., in inflamed joints.

Sterile injectable forms of the compositions of this invention may be aqueous or an oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols. Such compositions are prepared according to techniques well-known in the art of pharmaceutical formulation.

The compositions of this invention may be administered topically, especially when the target of treatment includes areas or organs readily accessible by topical application, including diseases of the eye, the skin, the joints, or the lower intestinal tract. Suitable topical formulations are readily prepared for each of these areas or organs. Topical application for the lower intestinal tract can be effected in a rectal suppository formulation (see above) or in a suitable enema formulation. Topically-transdermal patches may also be used.

For topical applications, the compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the compositions may be formulated in an ointment such as petrolatum.

The compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

In one embodiment, the antibodies or therapeutic compounds of this invention may be incorporated into liposomes ("immunoliposomes" in the case of antibodies), alone or together with another substance for targeted delivery to a patient or an animal. Such other substances can include nucleic acids for the delivery of genes for gene therapy or for the delivery of antisense RNA, RNAi or siRNA for activating NK cells or inhibiting mature dendritic cells, or toxins or drugs for the activation of NK cells (or inhibition of dendritic cells) through other means, or any other agent described herein that may be useful for the purposes of the present invention.

In another embodiment, the antibodies or other compounds of the invention can be modified to improve its bioavailability, half life in vivo, etc. For example, antibodies and other compounds can be pegylated, using any of the number of forms of polyethylene glycol and methods of attachment known in the art (see, e.g., Lee et al. (2003) Bioconjug Chem. 14(3):546-53; Harris et al. (2003) Nat Rev Drug Discov. 2(3):214-21; Deckert et al. (2000) Int J Cancer. 87(3):382-90).

Determining Dosage and Frequency of Administration

As described above, an important part of the present invention is testing anti-NKG2A antibodies in nonhuman primates to determine safe and effective doses and frequencies of administration. Suitable starting administration regimens can be determined by examining experience with other already developed therapeutic monoclonal antibodies. Several monoclonal antibodies have been shown to be efficient in clinical situations, such as Rituxan (Rituximab), Herceptin (Trastuzumab) Xolair (Omalizumab), Bexxar (Tositumomab), Campath (Alemtuzumab), Zevalin, Oncolym and similar administration regimens (i.e., formulations and/or doses and/or administration protocols) may be used with the antibodies of this invention. Schedules and dosages for administration can be determined in accordance with known methods for these products, for example using the manufacturers' instructions. For example, a monoclonal antibody can be supplied at a concentration of 10 mg/mL in either 100 mg (10 mL) or 500 mg (50 mL) single-use vials. The product is formulated for IV administration in 9.0 mg/mL sodium chloride, 7.35 mg/mL sodium citrate dihydrate, 0.7 mg/mL polysorbate 80, and Sterile Water for Injection. The pH is adjusted to 6.5. An exemplary suitable dosage range for an antibody of the invention may be between about 10 mg/m2 and 500 mg/m2. However, it will be appreciated that these schedules are exemplary and that optimal schedule and regimen can be adapted taking into account the affinity and anti-NKG2A activity of the antibody and the tolerability of the antibodies that must be determined in clinical trials. Quantities and schedule of injection of antibodies to NKG2As that saturate cells for 24 hours, 48 hours, 72 hours or a week or a month will be determined considering the affinity of the antibody and its pharmacokinetic parameters.

However, it will be appreciated that these schedules are exemplary and that optimal schedule and regimen can be adapted taking into account the affinity and anti-NKG2A activity of the antibody and the tolerability of the antibodies that must be determined in clinical or preclinical trials. Quantities and schedule of injection of antibodies to NKG2As that saturate cells for 24 hours, 48 hours 72 hours or a week or a month will be determined considering the affinity of the antibody and the its pharmacokinetic parameters.

The dose administered to a patient or nonhuman primate in the present methods should be sufficient to effect a beneficial response in the subject over time. The dose will be determined by the efficacy of the particular modulators employed and the condition of the subject, as well as the body weight or surface area of the area to be treated. The size of the dose also will be determined by the existence, nature, and extent of any adverse side-effects that may accompany administration in a particular subject. In determining the effective amount of the compound to be administered in a particular patient, a physician may evaluate circulating plasma levels of the compound, compound toxicities, and the production of anti-compound antibodies. In general, the dose equivalent of a compound is from about 1 ng/kg to 10 mg/kg for a typical subject. Administration can be accomplished via single or divided doses.

The antibodies of the invention that bind both human and non-human primate NKG2A receptors can be advantageously used in determining dosage and frequency of administration. The selection of an optimal therapeutic window for therapy with an anti-NKG2A antibody can be carried out based on administration of the antibody to a non-human primate. While NK cell activation in the short term (24 hour co-culture) has been suggested to avoid bone marrow cell (BMC) toxicity, it has been shown that longer (48 hour co-culture of bone marrow cells with activated NK cells) adversely affects hematopoietic reconstitution (Koh et al. (2002) Biol. Blood Marrow Transplant. 8:17-25). However, it would be valuable to employ administration regimens that permit exposure of NK cells in an individual to an NK cell activation anti-NKG2A antibody for a longer period, e.g. longer than 24 hours or even 48 hours. While not wishing to be bound by theory such a regimen where an anti-NKG2A antibody is present for greater than 24 hours or 48 hours would enable the anti-NKG2A antibody to come into contact with and activate a sufficient number of NK cells in the individual for a therapeutic effect against target (e.g. cancer, infected, inflammatory) cells. The inventors therefore provide a method of treating an individual with an anti-NKG2A antibody comprising exposing said individual to an anti-NKG2A antibody for a period for a period greater than 24 hours, more preferably 48 hours. Most preferably the invention comprises administering to said individual an anti-NKG2A antibody having a plasma half-life greater than 24 hours, or 48 hours, or more preferably of at least 5, 6, 7, 10, 14 or 20 days. Most preferably the invention comprises administering to said individual an anti-NKG2A antibody comprising an Fc portion, preferably an Fc portion of the G2 or G4 type. As further discussed herein, any suitable antibody that blocks NKG2A function can be used, for example an antibody having the binding specificity of Z199 or Z270. In preferred embodiments the antibody is administered in a second or further dose and the antibody will be a chimeric, CDR grafted, human or humanized antibody.

The present invention provides a method of identifying a suitable administration regimen for a therapeutic antibody directed against human NKG2A, the method comprising administering the antibody to a nonhuman primate using an administration regimen, preferably a series of regimens in which the dose or frequency of the antibody is varied, and determining the activity of NKG2A-expressing cells in the non-human primate and the effect of therapy on bone marrow cells (BMC) and/or hematopoietic cells, particularly myeloid cell reconstitution, of the primate for the particular administration regimen(s). Preferably the method further comprises assessing myeloid reconstitution following anti-NKG2A antibody administration, generally involving determining the number of days required for myeloid reconstitution to normalize, e.g. to levels approaching that observed prior to anti-NKG2A therapy or to a predetermined minimum level. It is then possible to select or identify an administration regimen that allows myeloid reconstitution to normalize.

The method can further comprise determining the activity of NKG2A-expressing cells in the non-human primate and/or identifying or selecting an administration regimen that leads to a detectable modulation in the activity of NKG2A-expressing cells.

Said administration regimen(s) can be expressed for example in terms of period of exposure of an individual to an anti-NKG2A antibody that activates an NK cell, and frequency of antibody administration. Based on such parameters, administration frequency and dosage can be adapted depending on the particular antibody used, e.g. taking account of the antibody's plasma half-life, affinity, bioavailability (or time to peak serum concentration), etc.

A determination that a regimen permits partial or complete recovery or normalization of myeloid reconstitution by the primate and leads to a detectable modulation in the activity of NKG2A-expressing cells indicates that the administration regimen is suitable for use in humans.

The catabolic rates of the endogenous human immunoglobulins have been well characterized. The half-life of IgG varies according to isotype, up to 3 weeks for IgG1, IgG2, and IgG4 and approximately 1 week for IgG3. Unless pharmacokinetics are altered by antigen binding or immunogenicity, intact human IgG monoclonal antibodies will exhibit pharmacokinetics comparable to endogenous IgG. As discussed previously, the extraordinarily long half-life of the human IgG1, IgG2, and IgG4 isotypes is due to catabolic protection by FcRn. FcRn is expressed on hepatocytes, endothelial cells, and phagocytic cells of the reticuloendothelial system (RES). When IgG undergoes endocytosis, the low pH of the endosome promotes binding of the IgG Fc domain to FcRn, which recycles IgG to the cell surface and salvages IgG from lysosomal degradation. The short half life of IgG3 compared to the other IgG isotypes is due to a single amino acid difference (an arginine instead of a histidine at position 435) in the FcRn binding domain.

The elimination of intact murine IgG1 and IgG2 antibodies is much faster than the corresponding human isotypes. Half-lives for murine antibodies are in the range of 12 to 48 hours in humans. The short half-life of murine antibodies in humans is due to low-affinity binding of the murine Fc domain to human FcRn. Human FcRn binds to human, rabbit, and guinea pig IgG, but not significantly to rat, bovine, sheep, or mouse IgG; mouse FcRn binds to IgG from all of these species. Antibody fragments, including $F(a')_2$, Fab, and scFV, lack the Fc domain and do not bind to FcRn. Therefore, the half-lives of these fragments are substantially shorter than intact IgG, with half-life determined predominantly by their molecular weights. Lower molecular weight Fab and scFv fragments are subject to renal clearance, which accelerates elimination. Reported half-lives have ranged from 11 to 27 h for F(ab')2 fragments and 0.5 to 21 h for Fab fragments. The half-life of monovalent and multivalent scFv constructs may range from minutes to several hours.

Antigen binding can significantly affect the pharmacokinetics of antibodies. If the antibody binds to an internalized cell membrane antigen or an immune complex formed with a secreted antigen is efficiently eliminated from circulation, the antigen may act as a "sink" for antibody clearance. An antigen sink will produce dose-dependent pharmacokinetics. If the dose level is insufficient to saturate the antigen pool, antigen-mediated clearance will predominate and the antibody half-life will be shorter than the half-life of endogenous IgG; at dose levels that saturate the antigen, RES-mediated clearance will predominate and half-life will be similar to endogenous IgG.

A preferred embodiment of the present invention describes a dosing regimen wherein anti-NKG2A antibody is administered in a first administration. The first dose of anti-NKG2A antibody activates NK cells and may indirectly by activating NK cells inhibit myeloid cell reconstitution in the individual. The second dose of anti-NKG2A antibody is administered to coincide with the pharmacodynamic profile of myeloid cell reconstitution recovery, e.g. to be administered at a time when an individual's rate of myeloid cell reconstitution is expected to have at least partially recovered. Thus, by using an anti-NKG2A antibody which cross-reacts with the receptor in humans and non-human primates, the inventors provide a method in which NK cells are brought into contact with an anti-NKG2A antibody for a period greater than 24 hours during which myeloid reconstitution has been reported to not be affected.

In preferred embodiments, the second dose of anti-NKG2A antibody will be administered at least 6, 7, 8, 9 or 10 days following the initial dose, and preferably at least 14, 15, 16, or 20 days following the initial dose. Most preferably the second dose of anti-NKG2A antibody will be administered at least 2, 3, 4, 5, 6, 7, 8, 9 or 10 days or at least 14, 15, 16, or 20 days following the time (day) at which anti-NKG2A antibody plasma concentration in a subject is estimated to reach half of the initial (at administration) concentration, preferably at least 6-10 days or at least 15-20 days following the duration of at least one plasma half-life of the anti-NKG2A antibody. Alternatively, the method can be expressed in terms of peak serum concentration of the anti-NKG2A antibody, where the second dose of anti-NKG2A antibody will be administered at least 2, 3, 4, 5, 6, 7, 8, 9 or 10 days or at least 14, 15, 16, or 20 days following the time (day) at which anti-NKG2A antibody plasma concentration in a subject is estimated to reach half of the peak serum concentration in the individual.

In a further embodiment, the second dose of anti-NKG2A antibody will be administered at least 2, 3, 4, 5, 6, 7, 8, 9 or 10 days or at least 14, 15, 16, or 20 days following the time (day) at which anti-NKG2A antibody plasma concentration in a subject is estimated to reach a non-detectable concentration, preferably at least 2, 3, 4, 5, 6, 7, 8, 9 or 10 days or at least 14, 15, 16, or 20 days following the duration of at least 2, 3, 4 or more plasma half-lives of the anti-NKG2A antibody.

In a preferred embodiment, an administration regimen is described for an antibody comprising an Fc region of the G2b or preferably G4 subtype (IgG2b or IgG4 respectively). Preferably said antibody has a plasma half-life of about 5, 6, 7, 8, 9, 10, 12, 15, 18, 20, or 21 days, or preferably of about 10 to 15 days, 15-21 days. Preferably the antibody comprises an Fc region substantially free of binding to Fc receptors on NK cells (CD16). Said antibody is preferably administered in a first dose, and a second and/or subsequent dose, wherein the second and/or subsequent dose is administered at least 6, 7, 8, 9, 10, 14, 15, 16, or 20 days after the antibody is estimated to reach half its initial concentration. Said second and/or subsequent dose can also be expressed in absolute number of days following administration, e.g. preferably at least 6, 7, 8, 9 or 10 days following the initial dose, and preferably at least 14, 15, 16, 20, 21, 24, 28, 30 or 35 days following the first administration. Said antibody may be an antibody comprising a naturally occurring Fc portion, preferably a naturally occurring human Fc portion, or more preferably may contain modifications such as one or more amino acid substitutions that increase the plasma half-life of the antibody and/or that modify binding to Fc receptors, for example increase binding to Fcn receptors to increase plasma half-life or decrease binding to FcgammaIIIa to decrease unwanted toxicity (ADCC) towards the NK cell. Such modifications can be carried out according to methods well known in the art, several of which modifications are further described herein.

In yet another preferred embodiment, an administration regimen is described for an antibody fragment, preferably a F(ab')2 fragment modified, for example with polyethylene glycol as described herein, to have a plasma half-life of about 5, 6, 7, 8, 9, 10, 12, 15, 18, 20, or 21 days. Said antibody is preferably administered in a first dose, and a second and/or subsequent dose, wherein the second and/or subsequent dose is administered at least 6, 7, 8, 9, 10, 14, 15, 16, or 20 days after the antibody is estimated to reach half its initial concentration. Said second and/or subsequent dose can also be expressed in absolute number of days following administration, e.g. preferably at least 6, 7, 8, 9 or 10 days following the initial dose, and preferably at least 14, 15, 16, 20, 21, 24, 28, 30 or 35 days following the first administration.

Pharmaceutical Combinations

According to another important embodiment of the present invention, the anti-NKG2A antibodies and/or other compounds may be formulated together with one or more additional therapeutic agents, including agents normally utilized for the particular therapeutic purpose for which the antibody or compound is being administered. The additional therapeutic agent will generally be administered at a dose typically used for that agent in a monotherapy for the particular disease or condition being treated. Such therapeutic agents include, but are not limited to, therapeutic agents used in the treatment of cancers ("anticancer compounds"; including chemotherapeutic compounds, hormones, angiogenesis inhibitors, apoptotic agents, etc.); therapeutic agents used to treat infectious disease (including antiviral compounds); therapeutic agents used in other immunotherapies, such as the treatment of autoimmune disease, inflammatory disorders, and transplant rejection; cytokines; immunomodulatory agents; adjunct compounds; or other antibodies and fragments of other antibodies against both activating and inhibitory NK cell receptors. Unless otherwise specifically stated, the combination compositions set forth below can comprise either an activating antibody, an inhibitory antibody or a cytotoxin-antibody conjugate of this invention.

Therapeutic agents for the treatment of cancer include chemotherapeutic agents (including agents that interfere with DNA replication, mitosis and chromosomal segregation, and agents that disrupt the synthesis and fidelity of polynucleotide precursors), hormonal therapy agents, anti-angiogenic agents, and agents that induce apoptosis.

Chemotherapeutic agents contemplated as exemplary include, but are not limited to, alkylating agents, antimetabolites, cytotoxic antibiotics, vinca alkaloids, for example adriamycin, dactinomycin, mitomycin, carminomycin, daunomycin, doxorubicin, tamoxifen, taxol, taxotere, vincristine, vinblastine, vinorelbine, etoposide (VP-16), 5-fluorouracil (5FU), cytosine arabinoside, cyclophosphamide, thiotepa, methotrexate, camptothecin, actinomycin-D, mitomycin C, cisplatin (CDDP), aminopterin, combretastatin(s) and derivatives and prodrugs thereof.

Hormonal agents include, but are not limited to, for example LHRH agonists such as leuprorelin, goserelin, triptorelin, and buserelin; anti-estrogens such as tamoxifen and toremifene; anti-androgens such as flutamide, nilutamide, cyproterone and bicalutamide; aromatase inhibitors such as anastrozole, exemestane, letrozole and fadrozole; and progestagens such as medroxy, chlormadinone and megestrol.

A number of exemplary chemotherapeutic agents for combined therapy are listed in Table C of U.S. Pat. No. 6,524,583, the disclosure of which agents and indications are specifically incorporated herein by reference. Each of the agents listed are exemplary and not limiting. The skilled artisan is directed to "Remington's Pharmaceutical Sciences" 15th Edition, chapter 33, in particular pages 624-652. Variation in dosage will likely occur depending on the condition being treated. The physician administering treatment will be able to determine the appropriate dose for the individual subject.

Examples of anti-angiogenic agents include neutralizing antibodies, antisense RNA, siRNA, RNAi, RNA aptamers and ribozymes each directed against VEGF or VEGF receptors (U.S. Pat. No. 6,524,583, the disclosure of which is incorporated herein by reference). Variants of VEGF with antagonistic properties may also be employed, as described in WO 98/16551, specifically incorporated herein by reference. Further exemplary anti-angiogenic agents that are useful in connection with combined therapy are listed in Table D of U.S. Pat. No. 6,524,583, the disclosure of which agents and indications are specifically incorporated herein by reference.

Exemplary apoptotic agents include, but are not limited to, bcr-abl, bcl-2 (distinct from bcl-1, cyclin D1; GenBank accession numbers M14745, X06487; U.S. Pat. Nos. 5,650,491 and 5,539,094; each incorporated herein by reference) and family members including Bcl-x1, Mcl-1, Bak, A1, and A20. Overexpression of bcl-2 was first discovered in T cell lymphomas. The oncogene bcl-2 functions by binding and inactivating Bax, a protein in the apoptotic pathway. Inhibition of bcl-2 function prevents inactivation of Bax, and allows the apoptotic pathway to proceed. Inhibition of this class of oncogenes, e.g., using antisense nucleotide sequences, RNAi, siRNA or small molecule chemical compounds, is contemplated for use in the present invention to give enhancement of apoptosis (U.S. Pat. Nos. 5,650,491; 5,539,094; and 5,583,034; each incorporated herein by reference).

Useful anti-viral agents that can be used in combination with the molecules of the invention include, but are not limited to, protease inhibitors, nucleoside reverse transcriptase inhibitors, non-nucleoside reverse transcriptase inhibitors and nucleoside analogs. Examples of antiviral agents include but are not limited to zidovudine, acyclovir, gangcyclovir, vidarabine, idoxuridine, trifluridine, and ribavirin, as well as foscarnet, amantadine, rimantadine, saquinavir, indinavir, amprenavir, lopinavir, ritonavir, the alpha-interferons, adefovir, clevadine, entecavir, and pleconaril.

For autoimmune or inflammatory disorders, any other compound known to be effective for one or more types of autoimmune or inflammatory disorders, or any symptom or feature of autoimmune or inflammatory disorders, including inter alia, immunosuppressants, e.g., azathioprine (e.g., Imuran), chlorambucil (e.g., Leukeran), cyclophosphamide (e.g., Cytoxan), cyclosporine (e.g., Sandimmune, Neoral), methotrexate (e.g., Rheumatrex), corticosteroids, prednisone (e.g., Deltasone, Meticorten), Etanercept (e.g., Enbrel), infliximab (e.g., Remicade), inhibitors of TNF, FK-506, rapamycin, mycophenolate mofetil, leflunomide, anti-lymphocyte globulin, deoxyspergualin or OKT.

Preferred examples of immunomodulatory compounds include cytokines. Other examples include compounds that have an effect, preferably an effect of activation or potentiation of NK cell activity, or of inducing or supporting the proliferation of NK cells. Examples of immunomodulating compounds include but are not limited to ligands of NOD and PKR receptors, agonists of TLRs (Toll-like receptors), such as agonists of TLR3 (dsRNA, poly I:C and poly A:U), TLR4 (ANA380, isatoribine, LPS and mimetics such as MPL), TLR7 (oligonucleotides, ssRNA), TLR9 (oligonucleotides such as CpGs), a number of examples of which are described in Akira and Takeda ((2004) Nature Reviews 4: 499), and antibodies that block inhibitory receptors on NK cells (for example that inhibit KIR2DL1 and KIR2DL2/3 activity) or act as agonists at NK cell activatory receptors (for example antibodies that crosslink NCR receptors NKp30, NKp44 or NKp46). Various cytokines may be employed in combined approaches according to the invention. Examples of cytokines useful in the combinations contemplated by this invention include IL-1alpha IL-1beta, IL-2, IL-3, IL-4, IL-5, IL-6, IL-7, IL-8, IL-9, IL-10, IL-11, IL-12, IL-13, IL-15, IL-21, TGF-beta, GM-CSF, M-CSF, G-CSF, TNF-alpha, TNF-beta, LAF, TCGF, BCGF, TRF, BAF, BDG, MP, LIF, OSM, TMF, PDGF, IFN-alpha, IFN-beta, IFN-gamma. Cytokines used in the combination treatment or compositions of this invention are administered according to standard regimens, consistent with clinical indications such as the condition of the patient and relative toxicity of the cytokine.

Adjunct compounds may include by way of example anti-emetics such as serotonin antagonists and therapies such as phenothiazines, substituted benzamides, antihistamines, butyrophenones, corticosteroids, benzodiazepines and cannabinoids; bisphosphonates such as zoledronic acid and pamidronic acid; and hematopoietic growth factors such as erythropoietin and G-CSF, for example filgrastim, lenograstim and darbepoietin.

Other therapeutic agents that can be formulated with the activating anti-NKG2A antibodies of this invention include other compounds that can activate NK cells. For example, compounds that stimulate NCRs, e.g. NKp30, NKp44, and NKp46, can be used (see, e.g., PCT WO 01/36630, Vitale et al. (1998) J. Exp. Med. 187:2065-2072, Sivori et al. (1997) J. Exp. Med. 186:1129-1136; Pessino et al. (1998) J. Exp Med. 188:953-960; the entire disclosures of which are herein incorporated by reference), as can inhibitors of the KIR inhibitory receptors (see, e.g., Yawata et al. (2002) Crit Rev Immunol 22:463-82; Martin et al. (2000) Immunogenetics. 51:268-80; Lanier (1998) Annu Rev Immunol. 16:359-93; the entire disclosures of which are herein incorporated by reference). Preferably, an activator, e.g. natural ligand or activating antibody, of NKp30 is used. In one embodiment, an inhibitor of TGF-beta 1 is used, as TGF-beta 1 can downregulate NKp30 (see, e.g., Castriconi et al. (2004) C.R. Biologies 327:533-537, the entire disclosure of which is herein incorporated in its entirety).

Therapeutic compounds that can be formulated with the inhibitory anti-NKG2A antibodies of this invention are compounds that can inhibit NK cells. Such compounds include inhibitors of NCRs, e.g. NKp30, NKp44, and NKp46, inhibitors of activating NKG2 receptors (e.g., NKG2C), activators of inhibitory KIR receptors, or activators of an inhibitory Ly49 receptor.

The activating antibodies of this invention may also be formulated together with an antigen to which tolerance is desired. It is believed that the enhanced killing of dendritic cells caused by the activating antibodies of this invention will cause tolerization of antigens presented to the immune system at that time. Such compositions are useful in treating autoimmune disease, as well as allergies. Examples of antigens that may be formulated with the activating antibodies of this invention include myelin basic protein, ragweed and other pollen and plant allergens, allergens responsible for pet allergies, allergens responsible for food allergies (such as peanut and other nut allergens, dairy product allergens, sesame and other seed allergens) or insect allergens.

The interrelationship of dosages for animals and humans (based on milligrams per meter squared of body surface) is described in Freireich et al., (1966) Cancer Chemother Rep 50: 219. Body surface area may be approximately determined from height and weight of the patient. See, e.g., Scientific Tables, Geigy Pharmaceuticals, Ardley, N.Y., 1970, 537. An effective amount of a compound of this invention can range from about 0.001 mg/kg to about 1000 mg/kg, more preferably 0.01 mg/kg to about 100 mg/kg, more preferably 0.1 mg/kg to about 10 mg/kg; or any range in which the low end of the range is any amount between 0.001 mg/kg and 900 mg/kg and the upper end of the range is any amount between 0.1 mg/kg and 1000 mg/kg (e.g., 0.005 mg/kg and 200 mg/kg, 0.5 mg/kg and 20 mg/kg). Effective doses will also vary, as recognized by those skilled in the art, depending on the diseases treated, route of administration, excipient usage, and the possibility of co-usage with other therapeutic treatments such as use of other agents.

For pharmaceutical compositions that comprise additional therapeutic agents, an effective amount of the additional therapeutic agent is between about 20% and 100% of the dosage normally utilized in a monotherapy regime using just that additional agent. Preferably, an effective amount is between about 70% and 100% of the normal monotherapeutic dose. The normal monotherapuetic dosages of these additional therapeutic agents are well known in the art. See, e.g., Wells et al., eds., Pharmacotherapy Handbook, 2nd supp. Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which are entirely incorporated herein by reference.

It is expected that some of the additional therapeutic agents listed above will act synergistically with the compounds of this invention. When this occurs, its will allow the effective dosage of the additional therapeutic agent and/or the compound of this invention to be reduced from that required in a monotherapy. This has the advantage of minimizing toxic side effects of either the additional therapeutic agent of a compound of this invention, synergistic improvements in efficacy, improved ease of administration or use and/or reduced overall expense of compound preparation or formulation.

It will be recognized by those of skill in the art that certain therapeutic agents set forth above fall into two or more of the categories disclosed above. For the purpose of this invention, such therapeutic agents are to be considered members of each of those categories of therapeutics and the characterization of any therapeutic agent as being in a certain specified category does not preclude it from also being considered to be within another specified category.

In yet another embodiment, the invention provides a composition of matter comprising an antibody of this invention and a second therapeutic agent or an allergen, selected from any of the agents or allergens set forth above, wherein the antibody and the second agent are in separate dosage forms, but associated with one another. The term "associated with one another" as used herein means that the separate dosage forms are packaged together or otherwise attached to one another such that it is readily apparent that the separate dosage forms are intended to be sold and administered as part of the same regimen. The agent and the antibody are preferably packaged together in a blister pack or other multi-chamber package, or as connected, separately sealed containers (such as foil pouches or the like) that can be separated by the user (e.g., by tearing on score lines between the two containers).

In still another embodiment, the invention provides a kit comprising in separate vessels, a) an antibody of this invention; and b) a second therapeutic agent or an allergen. Again, any of the therapeutic agents or allergens set forth above may be present in such a kit.

Therapeutic Use of Anti-NKG2A Antibodies and Compositions

The activating antibodies of the present invention render NK cells capable of lysing target cells bearing HLA-E or $Qa1^b$ on their cell surfaces when the NK cell comes into contact with the target cell. Thus, according to one embodiment, the invention provides a method of reconstituting NK cell-mediated lysis of a target cell in a population comprising a NK cell and said target cell, wherein said NK cell is characterized by NKG2A on its surface, and said target cell is characterized by the presence of HLA-E or $Qa1^b$ on its surface, said method comprising the step of contacting said NK cell with an above-described activating monoclonal antibody or a fragment thereof.

This activity is particularly useful in the treatment of conditions and disorders characterized by deleterious cells expressing HLA-E or $Qa1^b$ on their cell surface. One such cell type is a dendritic cell, preferably a mature dendritic cell. Thus, the invention provides a method of treating an autoimmune or inflammatory disorder or any other disorder caused at least in part by an excess of dendritic cells, or hyperactive dendritic cell activity. The method of treating such disorders comprises the step of administering to a patient a non-cytotoxic composition of the present invention that comprises an activating antibody.

Exemplary autoimmune disorders treatable using the present methods include, inter alia, hemolytic anemia, pernicious anemia, polyarteritis nodosa, systemic lupus erythematosus, Wegener's granulomatosis, autoimmune hepatitis, Behçet's disease, Crohn's disease, primary bilary cirrhosis, scleroderma, ulcerative colitis, Sjögren's syndrome, Type 1 diabetes mellitus, uveitis, Graves' disease, Alzheimer's disease, thyroiditis, myocarditis, rheumatic fever, ankylosing spondylitis, rheumatoid arthritis, glomerulonephritis, sarcoidosis, dermatomyositis, myasthenia gravis, polymyositis, Guillain-Barré syndrome, multiple sclerosis, alopecia areata, pemphigus/pemphigoid, Bullous pemphigoid, Hashimoto's thyroiditis, psoriasis, and vitiligo.

Examples of inflammatory disorders that can be treated by these methods include, but are not limited to, adrenalitis, alveolitis, angiocholecystitis, appendicitis, balanitis, blepharitis, bronchitis, bursitis, carditis, cellulitis, cervicitis, cholecystitis, chorditis, cochlitis, colitis, conjunctivitis, cystitis, dermatitis, diverticulitis, encephalitis, endocarditis, esophagitis, eustachitis, fibrositis, folliculitis, gastritis, gastroenteritis, gingivitis, glossitis, hepatosplenitis, keratitis, labyrinthitis, laryngitis, lymphangitis, mastitis, media otitis, meningitis, metritis, mucitis, myocarditis, myositis, myringitis, nephritis, neuritis, orchitis, osteochondritis, otitis, pericarditis, peritendonitis, peritonitis, pharyngitis, phlebitis, poliomyelitis, prostatitis, pulpitis, retinitis, rhinitis, salpingitis, scleritis, selerochoroiditis, scrotitis, sinusitis, spondylitis, steatitis, stomatitis, synovitis, syringitis, tendonitis, tonsillitis, urethritis, and vaginitis.

It has also been shown that alloreactive NK cell killing of dendritic cells improved engraftment of hematopoietic cells in a bone marrow transplant (L. Ruggeri et al., Science, 2002, 295:2097-2100). Thus, in another embodiment, the invention provides a method of improving the engraftment of hematopoietic cells in a patient comprising the step of administering to said patient a composition of this invention comprising an activating antibody. Improvement in grafting is manifested by any one of reduced incidence or severity of graft versus host disease, prolonged survival of the graft, or a reduction in or elimination of the symptoms of the disease being treated by the graft (e.g., a hematopoietic cancer). This method is preferably used in the treatment of leukemia.

Cancer cells have also been shown to evade killing through the presence of HLA-E on their surface. HLA-E has been detected on surgically removed glioblastoma specimens, in glioma cell lines and glioblastoma cell cultures (J. Wischhusen et al., J Neuropathol Exp Neurol. 2005; 64(6): 523-8); and in leukemia-derived cell lines, melanomas, melanoma-derived cell lines and cervical tumors (R Marin et al., Immunogenetics. 2003; 54(11):767-75). Thus, in another embodiment, the invention provides a method of treating a patient suffering from cancer, wherein said cancer is characterized by a cell expressing HLA-E, said method comprising the step of administering to said patient a composition of the present invention comprising an activating antibody.

Examples of cancers that may be treated according to this method include, but are not limited to, carcinoma, including that of the bladder, breast, colon, kidney, liver, lung, ovary, prostate, pancreas, stomach, cervix, thyroid and skin, including squamous cell carcinoma; hematopoietic tumors of lymphoid lineage, including leukemia, acute lymphocytic leukemia, acute lymphoblastic leukemia, B-cell lymphoma, T-cell lymphoma, Hodgkins lymphoma, non-Hodgkins lymphoma, hairy cell lymphoma and Burketts lymphoma; hematopoietic tumors of myeloid lineage, including acute and chronic myelogenous leukemias and promyelocytic leukemia; tumors of mesenchymal origin, including fibrosarcoma and rhabdomyoscarcoma; other tumors, including melanoma, seminoma, teratocarcinoma, neuroblastoma and glioma; tumors of the central and peripheral nervous system, including astrocytoma, neuroblastoma, glioma, and schwannomas; tumors of mesenchymal origin, including fibrosarcoma, rhabdomyoscaroma, and osteosarcoma; and other tumors, including melanoma, xeroderma pigmentosum, keratoacanthoma, seminoma, thyroid follicular cancer and teratocarcinoma.

Preferred cancers that can be treated according to the invention include gliomas, glioblastomas, leukemias, melanomas, and cervical tumors.

Virally infected cells also use HLA-E expression as a mechanism of avoiding NK cell killing. HLA-E expression has been associated with hepatitis C virus infected cells (J. Mattermann et al, American Journal of Pathology. 2005; 166:443-453); and cytomegalovirus infected cells (C. Cerboni et al., Eur J Immunol. 2001; 31(10):2926-35). Thus, in another embodiment, the invention provides a method of treating a patient suffering from a viral infection, wherein said viral infection is characterized by a virally-infected cell expressing HLA-E, said method comprising the step of administering to said patient a composition of the present invention comprising an activating antibody.

Examples of viral infections that may be treated by this method include, but are not limited to, infections caused by viruses of the family Retroviridae (e.g., human immunodeficiency viruses, such as HIV-1 (also referred to as HTLV-III, LAV or HTLV-III/LAV, or HIV-III; and other isolates, such as HIV-LP)); Picornaviridae (e.g., polio viruses, hepatitis A virus, enteroviruses, human Coxsackie viruses, rhinoviruses, echoviruses); Calciviridae (e.g., strains that cause gastroenteritis); Togaviridae (e.g., equine encephalitis viruses, rubella viruses); Flaviviridae (e.g., dengue viruses, encephalitis viruses, yellow fever viruses); Coronaviridae (e.g., coronaviruses); Rhabdoviridae (e.g., vesicular stomatitis viruses, rabies viruses); Filoviridae (e.g., ebola viruses); Paramyxoviridae (e.g., parainfluenza viruses, mumps virus, measles virus, respiratory syncytial virus); Orthomyxoviridae (e.g., influenza viruses) or avian influenza viruses (e.g. H5N1 or related viruses); Bungaviridae (e.g., Hantaan viruses, bunga viruses, phleboviruses and Nairo viruses); Arenaviridae (hemorrhagic fever viruses); Reoviridae (e.g., reoviruses, orbiviruses and rotaviruses); Birnaviridae; Hepadnaviridae (Hepatitis B virus); Parvoviridae (parvoviruses); Papovaviridae (papillomaviruses, polyoma viruses); Adenoviridae (most adenoviruses); Herpesviridae (herpes simplex virus (HSV) 1 and 2, varicella zoster virus, cytomegalovirus (CMV)); Poxviridae (variola viruses, vaccinia viruses, pox viruses); Iridoviridae (e.g., African swine fever virus); and unclassified viruses (e.g., the etiological agents of spongiform encephalopathies, the agent of delta hepatitis (thought to be a defective satellite of hepatitis B virus), the agents of non-A, non-B hepatitis (class 1=internally transmitted; class 2=parenterally transmitted (i.e., Hepatitis C); Norwalk and related viruses, and astroviruses).

Most preferably, the viral infection to be treated is selected from a hepatitis C virus infection or a cytomegalovirus infection.

The activating antibodies of this invention can also be used to induce tolerance to an antigen. Thus, according to another embodiment, the invention provides a method of inducing tolerance to an antigen in a patient comprising the steps of administering to said patient a composition of this invention comprising an activating antibody; and administering to said patient an antigen to which tolerance is desired. The method is preferably used to treat an allergy, wherein the antigen is an allergen. The choice of antigen can be made from those set forth above for combination compositions comprising an activating antibody of this invention and an antigen.

Compositions comprising the inhibitory antibodies of this invention or cytotoxin-antibody conjugates are useful for killing NK cells, reducing the activity of NK cells, reducing proliferation of NK cells, preventing the lysis of cells susceptible to NK cell lysis, or reducing the number of NK cells in a population. According to one embodiment, the invention provides a method of reducing the activity of NK cells, reducing proliferation of NK cells, preventing the lysis of cells susceptible to NK cell lysis, or reducing the number of NK cells in a population comprising the step of contacting a NK cell with a composition of this invention comprising an inhibitory antibody or a cytotoxin-antibody conjugate. These methods are particularly useful in diseases characterized by NK hyperactivity and/or hyperproliferation.

For example, co-owned PCT publication WO2005/105849 generally describes the use of antibodies against various NK cell receptors for the treatment of NK-Type LDGL. PCT publication WO 2005/115517 discloses that NK cell hyperactivity is associated with the presence, progression, stage and/or aggressiveness of pancreatic islet autoimmunity and thus plays a role in Type-I diabetes. Thus, according to one embodiment, the invention provides a method of treating a patient suffering from a condition characterized by NK cell hyperactivity or NK cell hyperproliferation comprising the step of administering to said patient a composition according to this invention comprising an inhibitory antibody or a cytotoxin-antibody conjugate. In a preferred embodiment, the condition is selected from NK-Type LDGL or Type I diabetes.

Any of the therapeutic methods described above may comprise the additional step of administering to the patient a second therapeutic agent suitable for the condition being treated. Examples of the types of second therapeutic agents that may be administered to the patient include a cytokine, a cytokine inhibitor, a hematopoietic growth factor, insulin, an anti-inflammatory agent, an immunosuppressant, an anti-cancer compound (such as a chemotherapuetic compound, an anti-angiogenic compound, an apoptosis-promoting compound, a hormonal agent, a compound that interferes with DNA replication, mitosis and/or chromosomal segregation, or an agent that disrupts the synthesis and fidelity of polynucleotide precursors), an adjunct compound (such as a pain reliever or an antiemetic), a compound that agonizes an activating NK cell receptor (such as NKp30, NKp44, and NKp46), an antagonist of an inhibitory NK cell receptor (such as an inhibitory KIR receptor), an antagonist of TGF-beta 1, a compound capable of stimulating an inhibitory NK cell receptor (such as natural ligands, antibodies or small molecules that can stimulate the activity of CD94/NKG2A receptors, or an inhibitory KIR receptor such as KIR2DL1, KIR2DL2, KIR2DL3, KIR3DL1, and KIR3DL2), or an inhibitor of an activating NK cell receptor (such as NKp30, NKp44, or NKp46).

Specific examples of the above-described classes of compounds are set forth in the section on pharmaceutical combinations and any of such specific compounds, as well as other members of any of these classes of therapeutic agents may be administered to a patient in the methods of this invention. The choice of therapeutic agent to use is easily made by those of skill in the medical arts and is dependent upon the nature of the condition being treated or prevented, the severity of the condition, the general overall health of the patient being treated, and the judgment of the treating physician.

The second therapeutic agent may be administered simultaneously with, prior to, or following the anti-NKG2A composition of this invention. When administered simultaneously, the second therapeutic agent may be administered as either a separately formulated composition (i.e., as a multiple dosage form), or as part of the antibody-containing composition.

In some embodiments, prior to the administration of a NKG2A antibody composition of this invention, the expression of NKG2A, and possibly other proteins, on NK cells will be assessed, and/or the activity or number of dendritic cells (preferably mature dendritic cells) and/or the presence of a NKG2A ligand (e.g., HLA-E or $Qa1^b$) on other cells, will be measured. This can be accomplished by obtaining a sample of NK or dendritic cells from the patient, and, for NK cells, testing e.g., using immunoassays, to determine the relative prominence of markers such as KIR receptors, other NKG2A receptors, or NCRs (e.g., NKp30, NKp44, NKp46), on the cells. Other methods can also be used to detect expression of these proteins, such as RNA-based methods, e.g., RT-PCR or Northern blotting. The detection of NK cells expressing NKG2A in the patient indicates that the present methods are well suited for use in treating the patient.

The treatment may involve multiple rounds of antibody. For example, following an initial round of administration, the level and/or activity of NKG2A-expressing NK cells, and/or dendritic cells or other cells expressing NKG2A or HLA-E, or $Qa1^b$ on their surface, can be re-measured, and, if appropriate, an additional round of administration can be performed. In this way, multiple rounds of receptor/cell/ligand detection and antibody composition administration can be performed, e.g., until the disorder is brought under control.

It will also be appreciated that more than one antibody can be produced and/or used using the present methods. For example, combinations of antibodies directed against different epitopes of NKG2A, against different combinations of NKG2A, CD94, or HLA-E, or against different isoforms of any of the three proteins that may exist in any individual may be used, as appropriate to obtain the ideal level of inhibition of NKG2A stimulation or inhibition of NK cell activity, either generally or in any individual patient (e.g., following an analysis of the NKG2A-expressing cells in the patient to determine an appropriate treatment regimen).

So long as a particular therapeutic approach is not known to be detrimental to the patient's condition in itself, and does not significantly counteract the NKG2A antibody-treatment, its combination with the present invention is contemplated.

The present invention may also be used in combination with classical approaches, such as surgery, and the like. When one or more second therapeutic agents or approaches are used in combination with the present therapy, there is no requirement for the combined results to be additive of the effects observed when each treatment is conducted separately. Although at least additive effects are generally desirable, as long as the antibody compositions of this invention remain effective to inhibit or activate NK cells, the methods of this invention may additionally comprise the use of a second therapeutic agent or other approach. Also, there is no particular requirement for the combined treatment to exhibit synergistic effects, although this is certainly possible and advantageous. The NKG2A antibody-based treatment may precede, or follow, the other treatment by, e.g., intervals ranging from minutes to weeks and months. It also is envisioned that more than one administration of an anti-NKG2A composition of the invention will be utilized. The second therapeutic agent or other approach may be administered interchangeably with the NKG2A antibody composition of this invention, on alternate days or weeks; or a cycle of anti-NKG2A treatment may be given, followed by a cycle of the other agent therapy or approach. In any event, for methods that comprise the additional step of administering a second therapeutic agent to a patient, all that is required is to deliver both the second therapeutic agent and the antibody of this invention in a combined amount effective to exert a therapeutically beneficial effect, irrespective of the times for administration.

It will be appreciated that the present methods of administering antibodies and compositions to patients can also be used to treat animals, or to test the efficacy of any of the herein-described methods or compositions in animal models for human diseases. Thus, the term "patient" as used herein means any warm-blooded animal, preferably a mammal, more preferably a primate and most preferably a human.

Further aspects and advantages of this invention are disclosed in the following experimental section, which should be regarded as illustrative and not limiting the scope of this application.

EXAMPLES

Example 1—Killing of Autologous IDC is Mediated by a Subset of CD94/NKG2A+KIR− NK Cells Polyclonal NK cells cultured in the presence of exogenous IL-2 were previously shown to display strong cytolytic activity against iDC. Accordingly, in the present study, polyclonal NK cell populations isolated from donors AM, AC and DB efficiently killed both autologous and allogeneic iDC. However, the cytolytic activity against autologous iDC could be incremented in the presence of appropriate anti-HLA class I mAb.

These data could be the consequence of the disruption of inhibitory interactions occurring between self HLA class I on DC and inhibitory receptors on NK cells. On the basis of these results, we formulated the hypothesis that only a fraction of the total NK cell pool displays spontaneous cytotoxicity against iDC whereas the other NK cells do not because of effective inhibitory interactions between their receptors and HLA class I molecules. To analyze this possibility, a panel of NK cell clones isolated from donors AM, AC and DB were assessed for cytolytic activity against autologous (and allogeneic) iDC. Consistent with our hypothesis, only a fraction of NK cell clones lysed autologous iDC. The other clones displayed either little or no cytotoxicity. Moreover, the percentage of cytolytic clones was slightly increased when target cells were represented by allogeneic iDC (see below).

To verify whether the inability of certain NK cell clones to lyse iDC reflected the interaction of their inhibitory NKR with HLA class I molecules, these clones were analyzed for the ability to lyse autologous iDC either in the absence or in the presence of anti-HLA class I mAb (i.e. under conditions that disrupt the inhibitory interactions). On the basis of the results of these experiments, NK cell clones were grouped into three different functional categories and further analyzed for the expression of HLA class I-specific inhibitory receptors including killer Ig-like receptor (KIR)2DL, KIR3DL1 and CD94/NKG2A (i.e. the main MHC class I-specific inhibitory receptors in humans).

The first group (group A) of NK clones was characterized by high spontaneous cytolytic activity against iDC. The magnitude of their cytolytic activity could not, or could only minimally, be increased in the presence of anti-HLA class I mAb. These clones were rather homogeneous in terms of expression of inhibitory receptors as they expressed CD94/NKG2A but lacked KIR2DL and KIR3DL1, which react with self-HLA class I alleles. The second group of NK cell clones (group B) was also characterized by the capability of spontaneously killing iDC. However, at variance with group A clones, their cytotoxicity increased in the presence of anti-HLA class I mAb. This suggested the occurrence of inhibitory interactions that limited, but did not abrogate, the NK-cell mediated cytolysis. This group was also composed of CD94/NKG2A+ clones and lacked KIR reactive with self-HLA class I alleles. Remarkably, the cytolytic activity of group B NK clones could also be incremented in the presence of anti-CD94 mAb thus indicating that the (partial) inhibition of cytotoxicity was indeed mediated by CD94/NKG2A.

NK clones belonging to the third group (group C) did not display cytotoxicity against autologous iDC. However, in the presence of anti-HLA class I mAb, iDC were efficiently lysed, suggesting the occurrence of potent inhibitory interactions. These NK clones were more heterogeneous regarding the expression of inhibitory receptors. Remarkably, virtually all NK clones expressing KIR2DL or KIR3DL1 specific for self-HLA class I alleles were included in this group. Moreover, some of these clones were characterized by the expression of a single KIR whereas others expressed multiple KIRs with different specificities. The reconstitution of cytolytic activity against iDC could be obtained not only with anti-HLA class I mAb but also with anti-KIR mAb (see below).

Finally a minor fraction of group C NK cell clones was KIR−CD94/NKG2A+. Their cytotoxicity could be reconstituted by mAb-mediated blocking of CD94 or by anti-HLA class I mAb. These data indicate that: (a) Not all NK cells are capable of killing autologous iDC (although all NK cells could lyse iDC in the presence of anti-HLA class I mAb); (b) clones displaying spontaneous cytolytic activity against iDC are restricted to an NK subset characterized by the CD94/NKG2A+KIR− surface phenotype (groups A and B); (c)

clones expressing KIR2DL or KIR3DL1, which are specific for self-HLA class I alleles, do not kill autologous iDC (group C).

Some NK clones expressed both self-reactive KIR and CD94/NKG2A. In all instances, they were confined to group C and their cytolytic activity could be reconstituted both by anti-HLA class I and anti-KIR mAb, whereas anti-CD94 mAb had little or no effect. Finally it is worth mentioning that KIR+NKG2A− clones were found to display cytolytic activity against iDC only in experiments in which iDC were derived from allogeneic (KIR mismatched) individuals. In this case, KIR+NKG2A− cells display alloreactivity because the expressed KIRs fail to recognize HLA class I alleles on allogeneic DC. The representative NK clone AM4 (KIR3DL1+) was unable to kill autologous iDC (BW4+ BW6−) whereas it lysed allogeneic, KIR mismatched (BW4−BW6+) iDC. Killing of autologous iDC could be reconstituted in the presence of anti-HLA class I mAb whereas killing of allogeneic iDC was not significantly modified.

Another example indicating the ability of KIR to distinguish between autologous and allogeneic, KIR-mismatched, iDC is provided by clone DB3, which co-expresses KIR2DL1 and KIR2DL2. This clone can be defined as "non-alloreactive" because, on the basis of its KIR phenotype, it should recognize all different HLA-C alleles (both group 1 and group 2). Indeed this clone did not kill autologous or allogeneic iDC whereas lysis of both targets could be efficiently reconstituted by anti-HLA class I mAb. Moreover, reconstitution of lysis was obtained by anti-KIR2DL2 mAb against autologous (CW1/CW3) iDC and by anti-KIR2DL1 mAb against allogeneic (CW2/CW4) iDC. Finally, as expected, in the case of NKG2A+KIR− clones no substantial difference existed in the ability to kill autologous or allogeneic iDC.

Example 2—the Susceptibility of IDC to NK-Mediated Cytotoxicity Reflects the Down-Modulation of HLA-E Class I Molecules Previous studies demonstrated that iDC and mDC display remarkable differences in terms of HLA class I surface expression. Thus, by the use of mAb specific for a monomorphic determinant of HLA-A, B, C and E molecules, it has been shown that DC undergoing maturation greatly up-regulate their HLA class I expression at the cell surface. Moreover, the up-regulation of HLA class I represented a crucial mechanism by which mDC become resistant to NK-cell-mediated lysis.

To directly assess the expression of various HLA class I molecules on cells representative of different stages of DC maturation we comparatively analyzed the expression of HLA-A, B, C and E on monocytes, iDC and mDC derived from the same individual. All HLA class I molecules were highly up-regulated in mDC as compared with iDC. Remarkably, they were clearly down-regulated in iDC as compared with monocytes (i.e. the precursors of iDC). Thus, it appears that the generation of iDC from monocytes results not only in the acquisition (or up-regulation) of novel surface molecules (for example CD1a) and functional properties but also in the loss (or down-regulation) of the expression of various molecules including CD14, and HLA-A, B, C and E molecules. This would suggest that the degree of HLA class I down-regulation is tuned to levels that allow iDC to become sensitive to lysis mediated by a particular subset of NK cells (CD94/NKG2A+KIR−).

Along this line, because KIR+NK cells are unable to kill iDC, it is conceivable that the amount of HLA-B or HLAC molecules expressed by iDC is sufficient to generate KIR cross-linking and delivery of inhibitory signals. On the other hand, the down-regulation of HLA-E would be sufficient to enable a fraction of KIR−NKG2A+NK cells to kill iDC. Indeed it can be seen that HLA-E (as detected by the HLA-E-specific 3D12 mAb) was almost undetectable in iDC whereas it was only partially re-expressed in mDC. However, in all instances, the HLA-E expression in mDC was lower as compared with monocytes or PBL derived from the same individual. Surprisingly, although HLA-A, B and C molecules were expressed by mDC at levels higher than by PHA blasts, the surface expression of HLA-E was consistently lower in mDC than in PHA blasts. In this context, previous studies provided clear evidence that autologous PHA blasts are highly resistant to NK lysis independently of the KIR/NKG2A phenotype of the effector NK cells.

Example 3—A Small Fraction of NK Clones can Mediate Killing of MDC

Consistent with previous reports that polyclonal NK cells do not efficiently kill mDC, we show that most NK cell clones that lysed iDC did not to kill mDC. Interestingly, however, mDC were lysed by a minor fraction of NK clones belonging to group A (i.e. those displaying spontaneous anti-iDC cytolytic activity that could not be increased by anti-HLA class I mAb). Lysis of autologous mDC was lower as compared with that of iDC and could be increased in the presence of anti-HLA class I mAb. This suggests that the higher expression of HLA-E in mDC as compared with iDC results in a more effective signaling via CD94/NKG2A (this is also suggested by the ability of anti-CD94 mAb to increase their lysis). Concerning group B NK clones (i.e. capable of killing iDC and whose lysis was incremented by anti-HLA class I mAb), they displayed no cytolytic activity again mDC; however, cytolytic activity could be revealed in the presence of anti-HLA class I or anti-CD94 mAb. Finally clones belonging to group C (in most instances KIR+), which are unable to kill iDC, also failed to kill mDC. Cytotoxicity against mDC could only be detected upon mAb-mediated disruption of the interaction between HLA class I and KIR.

Example 4—Heterogeneity of KIR−NKG2A+NK Cells in the Ability to Kill DC

As illustrated above, NK cell clones belonging to group A and B are characterized by a homogeneous KIR−NKG2A+ surface phenotype whereas group C includes either KIR+ NKG2A− or KIR−NKG2A+ clones, (or, less frequently, KIR+NKG2A+ clones). Assuming that the negative signaling via KIR is more effective than that via NKG2A (either because of an intrinsic difference in their signaling capability or because of the different availability of the specific HLA class I ligands on DC) it should be clarified why KIR−NKG2A+ cells are detectable in all three groups of NK clones. Since the cytolytic activity of a given NK cell clone is the result of a balance between inhibitory (KIR, NKG2A) and triggering (NCR, NKG2D) receptors, we analyzed the levels of expression of these molecules in the different groups of NK clones. In particular, we focused our attention on the expression of NKG2A and of NKp30 (i.e. the triggering NCR that plays a predominant role in the induction of NK-cell-mediated lysis of iDC and mDC).

First, the NKG2A+KIR− clones belonging to group A, B and C were evaluated for the level of NKG2A surface expression. NK clones belonging to group C expressed very high levels of NKG2A as compared with groups A and B. Moreover, group A clones were characterized by a lower expression of NKG2A as compared with group B clones. These data suggest the existence of an inverse correlation between the levels of NKG2A expression and the ability to kill iDC (and mDC). The low amounts of HLA-E molecules expressed in iDC may be differentially sensed by NK cells expressing high or low levels of NKG2A whereas mDC (expressing higher levels of HLA-E) are susceptible to lysis only by NK clones characterized by very low NKG2A surface density. Regarding the expression of NKp30, this was comparable in most NKG2A+ clones analyzed. Consistent with these data, their ability to kill iDC in the presence of anti-HLA class I mAb (i.e. in the absence of inhibitory interactions) did not show significant differences.

Discussion.

Heterogeneity exists even among NKG2A+KIR− cells in the magnitude of cytolytic responses. This appears to inversely correlate with the surface density of NKG2A. Accordingly, NK clones expressing low levels of NKG2A (group A) lysed both iDC and mDC whereas those expressing higher levels of NKG2A killed only iDC or, in a few cases, (NKG2Abright) failed to kill both iDC and mDC.

Notably, we also show that the surface expression of HLA-E is sharply reduced in iDC as compared with monocytes whereas it is partially recovered in mDC. On the contrary, the reduced cell surface levels of HLA-B and HLA-C in iDC are still sufficient to effectively engage KIR3DL1 or KIR2DL.

An unexpected finding was the identification of a small subset of NK cell clones belonging to group A (5-10%) that were capable of killing autologous mDC. These NK clones do not express self-reactive KIR and are characterized by low levels of NKG2A. This allows these NK cells to readily sense the down-regulation of HLA-E on target cells as compared with NK cells expressing higher levels of NKG2A. Accordingly no increases of the cytolytic activity of NKG2A low NK cells against iDC occurred in the presence of anti-HLA class I mAb. On the other hand, in the case of mDC (expressing higher levels of HLA-E), addition of anti-HLA class I mAb resulted in an increase of cytolytic activity, indicating that, provided a sufficient level of receptor-ligand interaction, NKG2A molecules expressed by group A clones can inhibit lysis. It is conceivable that in mDC some degree of heterogeneity might exist in the expression of HLA-E and, possibly, of ligand(s) of NKp30. Given the ability of a fraction of NK cells to discriminate between cells that express different amounts of HLA-E, it is possible that among mDC only some may express a surface density of HLA-E sufficient to confer resistance to this particular subset of NK cells.

Example 5—Z270 Anti-NKG2A MAB Increases Lytic Activity of NK Cell Lines Towards Immature Dendritic Cells Z270 is a mouse IgG1 monoclonal antibody against NKG2A. Because Z270 is a mouse antibody, it does not bind to human Fc receptors and thus acts as an activating antibody of this invention in human cell systems or in any system that lacks cells bearing mouse Fc receptors. In contrast, in a system comprising cells bearing a mouse Fc receptor, Z270 is an inhibitory antibody of this invention, due to the fact that its IgG1 constant region binds to such Fc receptors.

Human NK cell clones expressing NKG2A and immature dendritic cells (plasmacytoid dendritic cells or myeloid dendritic cells) were generated using standard methods. The lytic activity of the resulting human NK cell clones BH3, BH18 and BH34 was tested on autologous immature dendritic cells. Lytic activity of each of these clones against the iDC was tested in parallel in the absence or presence of monoclonal antibodies to CD94 (IgM) and to NKG2A (Z270, IgG1). For comparison, lytic activity in the presence of an anti-HLA class I antibody and a control IgG1 (anti-2B4 antibody) was also tested.

As shown in Table 1 below, NK clones showed little lysis of iDC in the absence of antibody or in the presence of control antibody anti-2B4 mAb. However, killing of the autologous iDC could be reconstituted in the presence of either anti-CD94, anti-NKG2A mAb Z270 or anti-HLA class I mAb. This result demonstrates that interference with NKG2A function reconstitutes NK cell lysis of iDC. It also demonstrates that the NKG2A binding region of monoclonal Z270 is capable of blocking NKG2A's inhibitory function.

TABLE 1

| lysis of autologous iDC | | | |
|---|---|---|---|
| NK Clone | BH3 | BH18 | BH34 |
| control lysis | 257 | 382 | 318 |
| anti CD94 | 1341 | 2455 | 2376 |
| anti-NKG2A (Z270) | 984 | 1977 | 2108 |
| anti-HLA class I | 1397 | 2603 | 2498 |
| anti-2B4 (control IgG1) | 236 | 353 | 292 |

Example 6—Reconstitution of Autologous Target Cell Lysis Using Anti-NKG2A Antibodies The cytolytic activity of human NK bulk cells against autologous PHA blast target cells expressing HLA-E in the absence of antibody or the presence of mAbZ199, or mAbZ270, was tested. Cytolytic activity was assessed by a standard 4 hour $^{51}$Cr release assay. All target cells were used at 3000 cells per well in microtitration plate. The number of NK cells was varied to produce effector/target ratios of between 0.01-100, as indicated in FIG. 1.

In the absence of antibody, NK cells displayed little if any cytolytic activity against target cells expressing HLA-E. However, in the presence of the anti-NKG2A antibody Z270 (having a mIgG1 constant region) or Z199 (having a mIgG2b constant region) NK clones became unable to recognize their HLA-E ligands and displayed strong cytolytic activity against the PHA blast targets. Z270 has a murine IgG1 constant region and Z199 has a murine IgG2b constant region. Neither of those antibodies can significantly bind to human Fc receptors.

Figure 2:
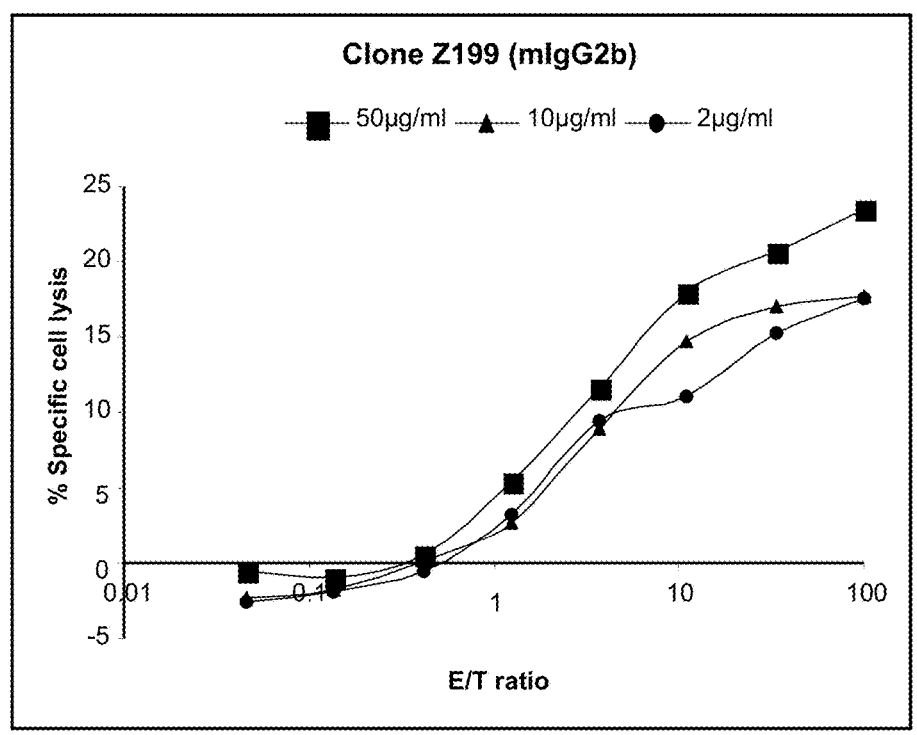
FIG. 2 depicts the effect of three different concentrations of Z199 on NK cell lysis of HLA-E expressing PHA blasts at varying ratios of NK cells to PHA blasts.
Figure 3:
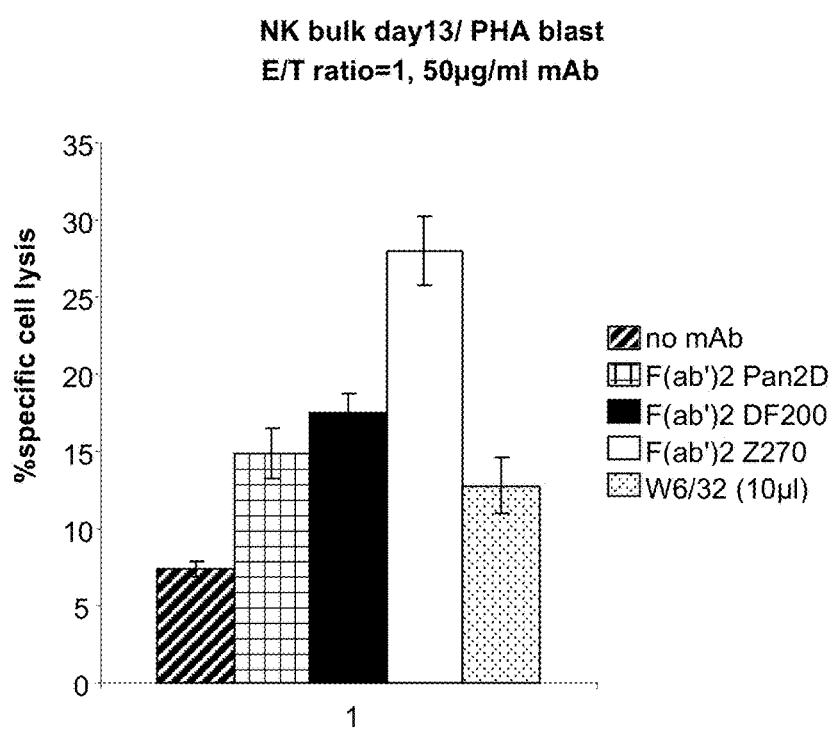
FIG. 3 depicts the effect of an F(ab')2 fragment of Z270 on NK cell lysis of HLA-E expressing PHA blasts.
Figure 4:
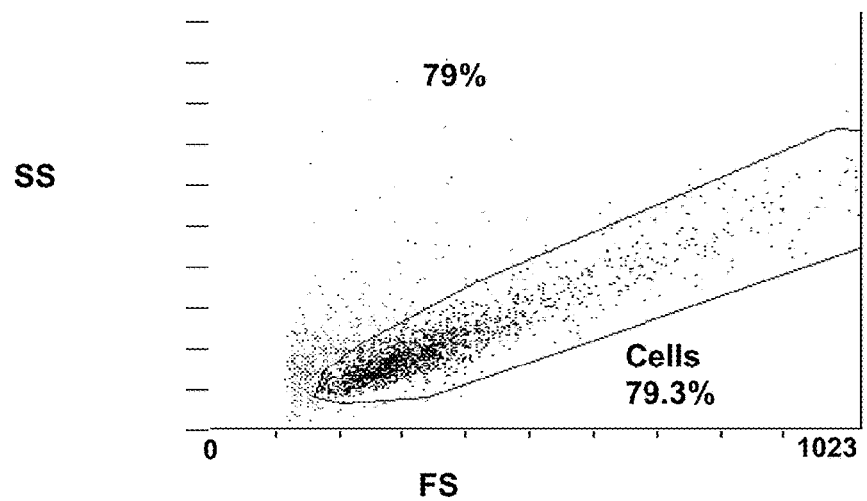
FIG. 4 shows binding to cynomolgus monkey NK cells of antibody Z270 as well as IgG1 and anti-CD16, demonstrating that Z270 binds to cynomolgus monkey NK cells. Binding was also shown for *macaca mulatta* and baboons.
Figure 4:
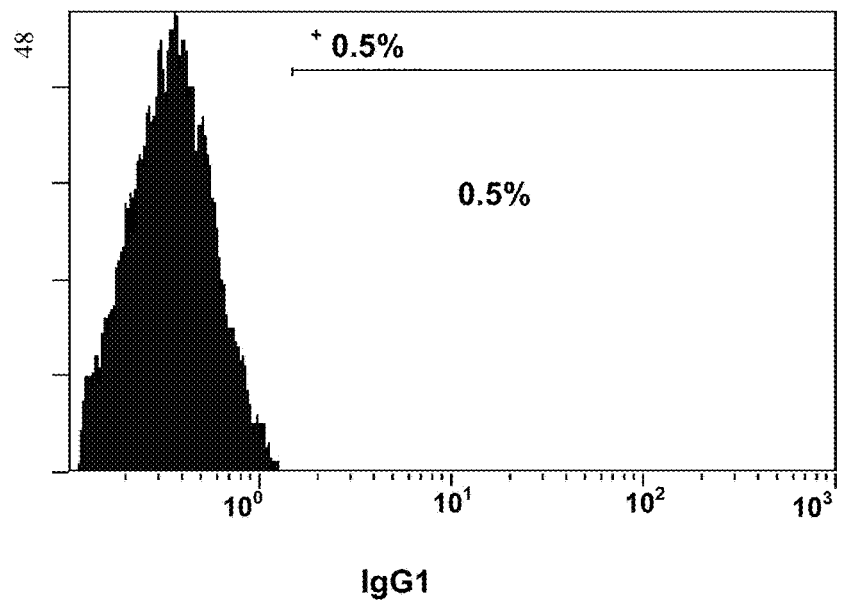
Figure 4:
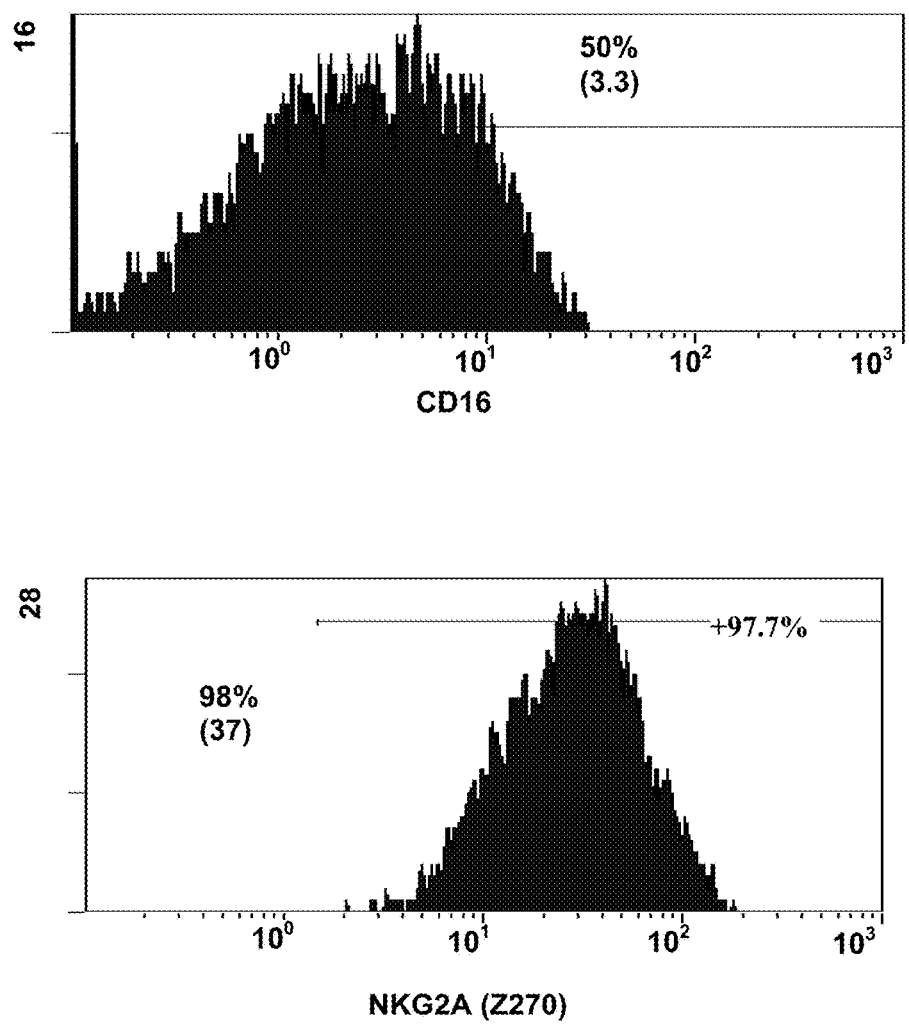

Similarly, inhibition of NK bulk cell killing of HLA-E positive autologous PHA blast cells could be efficiently reversed by the use of a Z270 F(ab')2 fragment (FIG. 2), an anti-KIR mAb DF200 or pan2D which block signaling through KIR2DL1 and KIR2DL2,3, or by antibody W6/32. Also, under the conditions tested (E/T ratio=1, 50 µg/ml mAb) PHA blast cells were not killed by NK bulk cells, but this inhibition could be reversed by the use of either Z270 mAb or Z270 Fab fragment.

Example 7—Materials and Methods mAb.

The following mAb, produced in our laboratory, were used in this study: JT3A (IgG2a, anti-CD3), AZ20 and F252 (IgG1 and IgM, respectively, anti-NKp30), c127 (IgG1, anti-CD16), c218 (IgG1, anti-CD56), EB6b (IgG1, anti-KIR2DL1 and KIR2DS1), GL183 (IgG1, anti-KIR2DL2 KIR2DL3 and KIR2DS2), FES172 (IgG2a, anti-KIR2DS4), Z27 (IgG1, anti-KIR3DL1), XA185 (IgG1, anti-CD94), Z199, Z270 (IgG2b, anti-NKG2A), A6-136 (IgM, anti-HLA class I), 131 (IgG1, anti-HLA-A alleles including A3, A11 and A24) and E59/53 (IgG2a, anti-HLA-A) [Ciccone et al, (1990) PNAS USA 87:9794-9797; Pende et al, (1998) J Immunol. 28:2384-2394]. The mAb F4/326 (IgG, anti-HLA-C) [Marsh et al, (1990) Tissue Antigens 36: 180-186], 116-5-28 (IgG2a, anti-HLA-Bw4 alleles) and 126-39 (IgG3, anti-HLA-Bw6 alleles) were kindly provided by Dr K. Gelsthorpe (Sheffield, GB) (XII International HLA Workshop) and 3D12 (IgG1, anti-HLA-E) [Lee et al. (1998) J. Immunol. 160:4951-4960] was kindly provided by Dr. Daniel Geraghty (Fred Hutchinson Cancer Research Center, Seattle, Wash.).

Anti-CD1a (IgG1-PE), anti-CD14 (IgG2a), anti-CD83 (IgG2b) and anti-CD86 (IgG2b-PE) were purchased from Immunotech (Marseille, France). D1.12 (IgG2a, anti-HLA-DR) mAb was provided by Dr R. S. Accolla (Pavia, Italy). HP2.6 (IgG2a, anti-CD4) mAb was provided by Dr P. Sanchez-Madrid (Madrid, Spain).

Generation of polyclonal or clonal NK cell populations. To obtain PBL, PBMC were isolated on Ficoll-Hypaque gradients and depleted of plastic-adherent cells. Enriched NK cells were isolated by incubating PBL with anti-CD3 (JT3A), anti-CD4 (HP2.6) and anti-HLA-DR (D1.12) mAb (30 min at 4° C.) followed by goat anti-mouse coated Dynabeads (Dynal, Oslo, Norway) (30 min at 4° C.) and immunomagnetic depletion. CD3-CD4-HLA-DR-cells were cultured on irradiated feeder cells in the presence of 100 U/ml rIL-2 (Proleukin, Chiron Corp., Emeryville, Calif.) and 1.5 ng/ml PHA (Gibco Ltd, Paisley, GB) to obtain polyclonal NK cell populations or, after limiting dilution, NK cell clones as previously described.

Generation of DC. PBMC were derived from healthy donors and plastic adherent cells were cultured in the presence of IL-4 and GMCSF (Peprotech, London, GB) at a final concentration of 20 ng/ml and 50 ng/ml, respectively. After 6 days of culture, cells were characterized by the CD14−CD1a+CD83− phenotype corresponding to iDC. To generate CD14−CD1a+CD83+CD86+ mDC, iDC were stimulated for 2 days with LPS (Sigma-Aldrich, St. Louis, Mich.) at a final concentration of 1 ug/ml.

Flow cytofluorimetric analysis and cytolytic activity. For one- or two-color cytofluorimetric analysis (FACSCalibur, Becton Dickinson and Co., Mountain View, Calif.), cells were stained with the appropriate mAb followed by PE- or FITC-conjugated isotype-specific goat anti-mouse second reagent (Southern Biotechnology Associated, Birmingham). Polyclonal and clonal NK cell populations were tested for cytolytic activity in a 4-h [510]-release assay against either autologous or heterologous DC. The concentrations of the various mAb added were 10 ug/ml for masking experiments. The E:T ratios are indicated in the text.

Example 8—Chimerization of Z270 Heavy and Light Chain Variable Regions

Frozen cell pellets of mouse hybridoma line, Z270, were thawed and processed using the RNeasy Midi Kit (Qiagen cat. No. 75142) to isolate 71 μg of total RNA. About 5 micrograms of Z270 RNA was subjected to reverse transcription to produce Z270 cDNA using the Amersham Biosciences 1st strand synthesis kit (Amersham Biosciences, Cat. No. 27-9261-01). Immunoglobulin heavy chain variable region (VH) cDNA was amplified by PCR using a number of different IgH primers in combination with a constant region primer in order to determine which primer pair was the most suitable for PCR. Similarly, immunoglobulin kappa chain variable region (VK) was amplified using multiple IgK primers in combination with a kappa constant region primer.

Suitable primers for each of the heavy and light chain variable regions were identified and ligated separately into pCR2.1®-TOPO Vectors® for transformation into *E. coli* TP010 bacteria, amplification and sequencing (using the BigDye® Terminator v3.0 Cycle Sequencing Ready Reaction Kit (ABI). The DNA sequence of the heavy chain variable region (Z270 VH) and the corresponding amino acid sequence are set forth in SEQ ID NO:1 and SEQ ID NO:2, respectively. The DNA sequence of the light chain variable region (Z270 VK) and the corresponding amino acid sequence are set forth in SEQ ID NO:3 and SEQ ID NO:4, respectively.

Chimerization of Z270 VK involved introducing via the appropriate primers and PCR, a Hind III restriction site, a Kozak translation initiation site and the K2A/RFT2 kappa leader sequence at the 5' end and a splice donor site and Bam HI restriction site at the 3' end of the Z270 VK DNA sequence. The resulting PCR product was cloned into a vector encoding the constant region of the human kappa light chain so as to encode a full-length chimeric light chain containing the variable region of the Z270 light chain. The DNA sequence of the resulting chZ270VK and the corresponding amino acid sequence are set forth in SEQ ID NO:5 and SEQ ID NO:6, respectively.

Chimerization of Z270 VH involved introducing via the appropriate primers and PCR, a Hind III restriction site, a Kozak translation initiation site and the A003 leader sequence at the 5' end and the 5' end of the gamma1 C region including a natural Apa I restriction site at the 3' end of the Z270 VH DNA sequence. The resulting PCR product was cloned into a vector encoding the constant region of the human IgG1 heavy chain so as to encode a full-length chimeric IgG1 heavy chain containing the variable region of the Z270 heavy chain. The DNA sequence of the resulting chZ270VH and the corresponding amino acid sequence are set forth in SEQ ID NO:7 and SEQ ID NO:8, respectively.

The resulting heavy and light chain containing plasmids were simultaneously electroporated into COS 7 cells which expressed the resulting human IgG1-kappa chimersation construct of Z270.

Example 9—Generation of New MABS mAbs were generated by immunizing 5 week old Balb C mice NK clone SA260 (CD94bright). After different cell fusions, the mAbs Z199 and Z270 were first selected as described in Moretta et al., (1994) J. Exp. Med. 180:545. Analysis of resting or activated NK cell populations for the distribution of the CD94 molecules was performed using one or two-color fluorescence cytofluorometric analysis as described in Moretta et al. (1994).

Positive monoclonal antibodies were further screened for their ability to reconstitute lysis by NK clones. The cytolytic activity of NK clones was assessed by a standard 4 hour $^{51}$Cr release assay in which effector NK cells were tested against the P815 mouse cell line or the C1R human cell line transfected or not with various HLA class I genes. Other target cells used in these studies were represented by the human HLA-class I-LCL 721.221 cell line either untransfected or transfected with various HLA classes as described in Sivori et al. (1996) Eur. J. Immunol. 26: 2487-2492.

Example 10—Purification of PBLs and Generation of Polyclonal or Clonal NK Cell Lines PBLs are obtained from healthy donors by Ficoll Hypaque gradients and depletion of plastic adherent cells. To obtain enriched NK cells, PBLs are incubated with anti CD3, anti CD4 and anti HLA-DR mAbs (30 minutes at 4° C.), followed by goat anti mouse magnetic beads (Dynal) (30 minutes at 4° C.) and immunomagnetic selection by methods known in the art (Pende et al., 1999). $CD3^-$, $CD4^-$, $DR^-$ cells are cultivated on irradiated feeder cells and 100 U/ml Interleukin 2 (Proleukin, Chiron Corporation) and 1.5 ng/ml Phytohemagglutinin A (Gibco BRL) to obtain polyclonal NK cell populations. NK cells are cloned by limiting dilution and clones of NK cells are characterized by flow cytometry for expression of cell surface receptors.

Example 11—Staining of Whole Blood from Monkeys to Identify Individual Expression of Receptors Binding Anti-NKG2A mAb Materials Monkey blood: blood for rhesus and cynomolgus monkeys was purchased at Centre de Primatologie, ULP, Strasbourg. Monkey blood for Baboons was purchased at Centre de Primatologie, CNRS, Station Rousset. Monkey blood was collected in "vacutainer" tube containing EDTA or sodium citrate. Blood was processed within the 24 hours following collection and kept at room temperature.

Antibodies: FITC-CD3, -CD4, -CD14, -CD20, and CyCr-CD45 are from BD Pharmingen, PC7-CD16 was obtained from Beckman Coulter; all these clones are cross-reacting with monkey PBMCs. PE-GaM (Goat F(ab')2 fragment anti-Mouse IgG (H+L)-PE), and OptiLyse® C were purchased from Beckman Coulter. Anti-NKG2a mAb (clone Z270, mouse IgG1) used at 1 µg/ml.

Other reagents: PBS (1×) obtained from Gibco Invitrogen; mouse serum from NMRI mouse from Janvier; Formaldehyde 37% from Sigma.

Methods:

Cell staining was carried out according to the following protocol:
 100 µl of blood+10 µl of 10× purified mAb
 Incubate with agitation 30 min at RT
 Wash with 3 ml PBS (1400 RPM 10 min RT)
 Add 100 µl PE-GaM or PE-GaH, 1:200 final, vortex
 Incubate with agitation 30 min at RT
 Wash with 3 ml PBS (1400 RPM 10 min RT)
 Add 50 µl of 20% mouse serum, vortex and incubate 10 min
 Add 30 µl to 60 µl of FITC-CD3, (-CD4, -CD14, -CD20), PC7-CD16, CyCr-CD45 mixture or 10 µl of each corresponding isotypic control
 Incubate with agitation 30 min at RT
 Add 500 µl OptiLyse® C, vortex and incubate 10 min
 Add 500 µl PBS, vortex and incubate 10 min
 Wash with 3 ml PBS (1400 RPM 10 min RT)
 Resuspend cell pellet in 300 µl PBS+0.2% Formaldehyde.

Flow cytometry was carried out according to the following protocol:
 Samples are run on a XL/MCL cytometer (Beckman Coulter). Acquisition and analysis are performed with EXPO™ 32 v1.2 software (Beckman Coulter).
 Analysis is focused on lymphocytes identified by their FSC and SSC features.
 Analysis of the T cell or NK cell compartments:
 T cells=$CD3^+$ lymphocytes are defined as the positive cells of the anti-CD3 staining histogram gated on Ly.
 NK cells=$CD3^-CD56^+$ lymphocytes corresponds to the $CD3^-CD56^+$ gate in the CD3/CD56 dot plot (upper left part of the quadrant).

Results

Binding of NKG2A monoclonal antibody Z270 to rhesus monkeys, cynomolgus monkeys and baboons was assessed. Cynomolgus monkey bulk NK cells (day 16, 300 uml were incubated 30 min at 4° C. with mAb (1 µg/ml), washed and labelled 20 min at 4° C. with PE-GaM. FIG. 1 shows binding to cynomolgus monkey NK cells, as well as IgG1 and anti-CD16 binding demonstrating that Z270 binds to cynomolgus monkey NK cells. *Macaca mulatta* (rhesus monkey) NK cells (from whole blood) were incubated with mAb, washed and labelled with PE-GaM. Results, shown in Table 2, demonstrate binding of clone Z270 to the rhesus monkey NK cells. Finally, baboon NK cells (from whole blood) were incubated with mAb, washed and labelled with PE-GaM. Results, shown in Table 3, demonstrate binding of clone Z270 to the baboon NK cells.

Example 12—Staining of Whole Blood from Monkeys to Identify Individual Expression of Receptors Binding Anti-NKG2a mAb Materials Monkey blood from rhesus and cynomolgus monkeys was collected in a tube containing EDTA or sodium citrate. Antibodies: FITC-CD3, -CD4, -CD14, -CD20, and CyCr-CD45 are from BD Pharmingen, PC7-CD16 was obtained from Beckman Coulter; all these clones are cross-reacting with monkey PBMCs. PE-GaM (Goat F(ab')2 fragment anti-Mouse IgG (H+L)-PE), and OptiLyse® C were purchased from Beckman Coulter. Other reagents: PBS (1×) obtained from Gibco Invitrogen; Formaldehyde 37% from Sigma.

Methods:

Cell staining was carried out according to the following protocol:
 100 µl whole blood (EDTA)+11 µl mAb solution, Z270 or Z199 (10 µg/ml) or isotype control, incubated for 30 min at RT
 Wash with PBS, add 100 µl PE- or FITC GaM (1/200 final) and leave for 30 min at RT
 Wash with PBS, add 50 µl mouse serum 20%, add 60 µl containing FITC-anti-CD3, -CD4, -CD14, -CD20, CyCr-CD45, PC7-CD16 and leave for 30 min at RT
 Add 500 µl of optilyseC, leave for 10 min at RT
 Add 500 µl of PBS and leave for 10 min at RT
 Wash with PBS and with 0.2% Formaldehyde.
 Analysis focus on $CD45^{bright}$ small cells (CD45/SSC) then on $CD16^+ CD3^-CD4^-CD14^- CD20^-$ cells.

Results

Binding of NKG2A monoclonal antibodies Z270 and Z199 to rhesus monkey NK cells and cynomolgus monkey NK cells was assessed and compared. Cynomolgus monkey bulk NK cells (day 16, 300 µl were incubated 30 min at 4° C. with mAb (1 µg/ml), washed and labelled 20 min at 4° C.

with PE-GaM. Table 4 shows binding of both Z199 and Z270 to cynomolgus monkey NK cells, as well as IgG1 and anti-CD16 binding demonstrating that both Z199 and Z270 bind to cynomolgus monkey NK cells. *Macaca mulatta* (rhesus monkey) NK cells (from whole blood) were incubated with mAb, washed and labelled with PE-GaM. Results, shown in Table 5, demonstrate binding of both clones Z199 and Z270 to the rhesus monkey NK cells.

It has further been observed (Biassoni et al, (2005) J. Immunol. 174: 5695-5705, see FIGS. 5 and 6) that Z199 binds cynomolgus monkey NKG2C in addition to NKG2A, and moreover that this mAb results in increase in lysis of P815 target cells in a redirected killing assay. The latter increase in lysis is the opposite observed with human NK cells and is opposite that which would be expected for an inhibitor receptor NKG2A. Thus, while not wishing to be bound by theory present inventors propose that Z199 acts through the activatory receptor NKG2C in cynomolgus monkeys. Z270 also binds cynomolgus monkey cells and results in an increase in lysis of P815 target cells in a redirected killing assay suggesting that Z270 also recognizes NKG2C in the cynomolgus monkey.

The level of binding however of the two mAbs on the same species (cynomolgus for example) is very different both in terms of percentage of cells stained and intensity of fluorescence. This means that the two antibodies bind differently to NKG2A epitopes.

TABLE 2

| mulatta | sex | weight (kg) | % N | m IgG1 % | Z270 % | MFI+ |
|---|---|---|---|---|---|---|
| CH256 | F | 8.4 | 3.5 | 0.8 | 78.1 | 6.5 |
| *8703 | F | 7.1 | 2.4 | 0.4 | 56.1 | 5.3 |
| P9215 | F | 5.85 | 4.4 | 1.4 | 89.7 | 12.9 |
| RU925 | F | 1 | 5.9 | 0.4 | 95.2 | 15 |
| 201 | M | 14.6 | 14.4 | 1.3 | 95.7 | 8.1 |
| PM021 | M | 3.7 | 5 | 0.8 | 61.7 | 5.7 |
| MM031 | M | 2.25 | 1.8 | 0.4 | 88.1 | 10 |

TABLE 2-continued

| mulatta | sex | weight (kg) | % N | m IgG1 % | Z270 % | MFI+ |
|---|---|---|---|---|---|---|
| N0401 | M | 1.75 | 2.6 | 0.5 | 87.1 | 8.99 |
| N0404 | M | 1.25 | 1.7 | 0.6 | 86.3 | 9 |
| Mean | | | | 0.7 | 83 | 9.1 |
| SD | | | | 0.4 | 12.3 | 3.2 |
| n | | | | 9 | 9 | 9 |
| Range | | | | | 61.7-95.7 | 5.3-12.9 |

TABLE 3

| Baboon | sex | birth | % NK | m IgG1 % | m IgG1 tot. MFI | Z270 % | Z270 tot. MFI |
|---|---|---|---|---|---|---|---|
| K05 | F | Jan. 1, 1994 | 6.7 | | | 34 | 0.9 |
| K938A | F | Dec. 29, 1998 | 1.3 | 0.3 | 0.3 | 8.7 | 0.9 |
| O22V | F | Jul. 7, 1998 | 2.9 | 0.5 | 0.2 | 0.4 | 0.2 |
| V992 | F | Jan. 31, 1999 | 5.1 | 0.6 | 0.3 | 41.2 | 1 |
| V997 | F | Mar. 29, 1999 | 5.5 | 0.7 | 0.2 | 32.3 | 0.8 |
| V999 | F | Apr. 4, 1999 | 5.2 | 0.3 | 0.2 | 2.3 | 0.3 |
| V9912 | F | May 7, 1999 | 4.7 | 0.2 | 0.2 | 12 | 1.4 |
| V9914 | F | May 17, 1999 | 3.8 | 0.1 | 0.3 | 10.9 | 1 |
| V9926 | F | Jun. 13, 1999 | 5.4 | 0.5 | 0.2 | 2.7 | 0.3 |
| V9929 | F | Nov. 7, 1999 | 7.9 | 0.3 | 0.2 | 0.9 | 0.2 |
| PA977 | M | Dec. 3, 1997 | 2.8 | 0.9 | 1.1 | 11.4 | 1.6 |
| PA983 | M | Aug. 13, 1998 | 4.5 | 0.1 | 0.7 | 24.6 | 2 |
| V942A | M | Jun. 10, 1999 | 0.8 | 1.7 | 1 | 14.3 | 1.6 |
| V857C | M | Oct. 29, 2000 | 7.2 | 0.8 | 1.4 | 79.7 | 9 |
| V861B | M | Jan. 7, 2000 | 0.8 | 0.2 | 0.6 | 57.1 | 2.5 |
| V914B | M | Feb. 19, 2000 | 2 | 0.4 | 1.1 | 0.8 | 1.3 |
| V918C | M | Feb. 19, 2000 | 4.2 | 0.3 | 1.1 | 79.7 | 9 |
| V9812 | M | Jul. 6, 1998 | 5.6 | 1.3 | 1.2 | 78.1 | 6.2 |
| V989 | M | Jun. 1, 1998 | 1.5 | 1.2 | 1.2 | 12.4 | 2 |
| V9920 | M | Aug. 26, 1999 | 3.7 | 0.7 | 0.8 | 14.2 | 1.6 |
| Mean | | | 4.1 | | | 30.3 | |
| SD | | | 2.1 | | | 27.35 | |
| Range | | | 0.8 to 7.9 | | | 2.3 to 79.7 | |
| n | | | 20 | | | 17 | |

TABLE 4

Analysis of NK cell subsets from peripheral rhesus monkey whole blood

| Name | Weight (kg) | % NK | | | | | Mean | IgG1 MFI | IgG1 NK+ | Z270 % MFI | Z270 % NK+ | Z270 MFI NK+ | IgG2b MFI | IgG2b % NK+ | Z199 % MFI | Z199 % NK+ | Z199 MFI NK+ |
|---|---|---|---|---|---|---|---|---|---|---|---|---|---|---|---|---|---|
| 34459 | 9.6 | 5.81 | 5.88 | 6.07 | 6.06 | 6.44 | 6.1 | 0.76 | 1.4 | 2.7 | 40.8 | 5.6 | 0.7 | 1.2 | 63.8 | 96.2 | 66.3 |
| 31828 | 7.9 | 9.9 | 9.95 | 9.09 | 9.54 | 9.44 | 9.6 | 0.65 | 0.4 | 4.3 | 88.9 | 4.6 | 0.7 | 0.5 | 101.0 | 99.8 | 101.0 |
| O967 | 10.4 | 13.2 | 14.1 | 14 | 13.5 | 13.5 | 13.7 | 0.67 | 0.5 | 2.7 | 40.8 | 5.6 | 0.7 | 0.5 | 62.3 | 84.8 | 73.4 |
| R00093 | 6.2 | 4.93 | 5.22 | 5.25 | 5.38 | 5.09 | 5.2 | 0.68 | 1.0 | 2.5 | 40.9 | 4.5 | 0.6 | 0.4 | 81.9 | 97.9 | 83.6 |
| R00013 | 7.6 | 6.2 | 7.36 | 7.34 | 7.28 | 6.21 | 6.9 | 0.66 | 0.3 | 1.4 | 12.4 | 3.8 | 0.6 | 0.2 | 38.8 | 97.8 | 39.7 |
| R00085 | 7.6 | 7.63 | 7.59 | 7.87 | 7.13 | 7.88 | 7.6 | 0.7 | 0.9 | 3.0 | 49.3 | 4.7 | 0.7 | 0.3 | 68.4 | 91.9 | 74.4 |
| R00055 | 6.8 | 8.54 | 8.04 | 8.01 | | | 8.2 | 0.7 | 0.6 | 4.0 | 65.8 | 5.3 | 0.6 | 0.9 | | | |
| R99273 | 9.4 | 10.1 | 9.85 | 8.8 | 9.8 | 9.27 | 9.6 | 0.54 | 0.5 | 2.0 | 49.5 | 2.9 | 0.4 | 0.6 | 32.7 | 98.0 | 33.4 |
| R00073 | 5.6 | 8.43 | 7.8 | 7.31 | 7.29 | 7.72 | 7.7 | 0.4 | 0.5 | 2.2 | 84.5 | 2.4 | 0.4 | 0.39 | 31.6 | 99.1 | 31.9 |
| R00073 | 6.1 | 5.65 | 5.56 | 5.45 | 5.69 | 4.28 | 5.3 | 0.59 | 0.7 | 3.3 | 84.8 | 3.7 | 0.3 | 0.3 | 31.9 | 98.0 | 32.6 |
| R00077 | 7.2 | 11.2 | 10.9 | 11.9 | 10 | 7.9 | 10.4 | 0.41 | 0.4 | 5.0 | 80.2 | 6.1 | 0.4 | 0.5 | 30.4 | 97.1 | 31.3 |
| R00025 | 6.3 | 6.91 | 6.57 | 10.3 | 9.87 | 9.27 | 8.6 | 0.45 | 0.7 | 2.2 | 79.2 | 2.5 | 0.4 | 0.4 | 30.0 | 97.3 | 30.9 |
| R00041 | 7.7 | 9.72 | 9.71 | 9.16 | 9.25 | 8.49 | 9.3 | 0.48 | 0.9 | 2.9 | 77.4 | 3.5 | 0.4 | 0.3 | 33.1 | 89.6 | 36.9 |
| R00099 | 5.8 | 6.14 | 5.8 | 6.12 | 5.45 | 5.39 | 5.8 | 0.56 | 1.2 | 2.5 | 58.5 | 3.6 | 0.5 | 0.3 | 31.1 | 97.6 | 31.8 |
| R00037 | 5.1 | 4.75 | 5.01 | 5.01 | 4.7 | 3.88 | 4.7 | 0.5 | 0.6 | 1.5 | 50.1 | 1.9 | 0.5 | 0.3 | 26.7 | 96.9 | 27.5 |
| R00023 | 5.8 | 11.8 | 11 | 10.7 | 8.46 | 11.3 | 10.6 | 0.5 | 0.3 | 4.4 | 90.9 | 4.7 | 0.3 | 0.6 | 34.0 | 96.4 | 35.3 |
| R00101 | 6.1 | 12.1 | 11.6 | 13 | 12.1 | 11.5 | 12.1 | 0.58 | 0.5 | 6.0 | 82.5 | 7.1 | 0.5 | 0.4 | 37.1 | 98.7 | 37.6 |
| R00061 | 5.7 | 5.96 | 5.26 | 5.62 | 5.6 | 5.59 | 5.6 | 0.5 | 0.5 | 5.4 | 59.4 | 8.5 | 0.6 | 0.2 | 1.6 | 40.7 | 2.4 |
| R00007 | 6.5 | 18.4 | 17.5 | 16.6 | 18 | 18.8 | 17.9 | 0.52 | 1.5 | 3.8 | 67.9 | 4.9 | 0.4 | 0.7 | 34.9 | 99.6 | 35.0 |
| Mean | | | | | | | 8.7 | 0.6 | 0.7 | 3.4 | 63.4 | 4.3 | 0.5 | 0.5 | 29.6 | 93.2 | 30.6 |
| SD | | | | | | | 3.3 | 0.1 | 0.4 | 1.5 | 21.3 | 2.0 | 0.1 | 0.3 | 9.2 | 13.6 | 9.3 |

TABLE 5

Analysis of NK cell subsets from peripheral cynomolgus monkey whole blood

|  | Kg | % NK | | | | | Mean | IgG1 MFI | % NK+ | Z270 MFI | % NK+ | MFI NK+ | IgG2b MFI | % NK+ | Z199 MFI | % NK+ | MFI NK+ |
|---|---|---|---|---|---|---|---|---|---|---|---|---|---|---|---|---|---|
| 1221 | 9.1 | 14.9 | 13.7 | 15 | 14.4 | 14.3 | 14.4 | 0.53 | 0.6 | 4.6 | 57.1 | 7.1 | 0.8 | 1.3 | 105.0 | 96.7 | 109.0 |
| M859 | 9 | 7.76 | 8.8 | 8.18 | 8.83 | 8.13 | 8.3 | 0.51 | 0.2 | 4.6 | 74.7 | 5.7 | 0.6 | 0.2 | 144.0 | 95.1 | 152.0 |
| R390 | 3.6 | 4.11 | 3.77 | 3.61 | 2.84 | 3.73 | 3.6 | 0.39 | 0.2 | 3.6 | 43.9 | 6.9 | 0.5 | 0.2 | 32.3 | 99.0 | 32.6 |
| T270 | 3.6 | 16.4 | 16.1 | 17.8 | 18.8 |  | 17.3 | 0.54 | 0.2 | 1.1 | 4.5 | 3.4 | 0.6 | 0.2 | 113.0 | 97.7 | 116.0 |
| T788 | 3.3 | 5.55 | 5.22 | 5.41 | 4.95 | 5.63 | 5.4 | 0.5 | 0.3 | 1.8 | 18.8 | 4.6 | 0.6 | 0.4 | 123.0 | 97.0 | 126.0 |
| AK565 | 3.9 | 10.7 | 10.4 | 9.82 | 9.98 | 9.59 | 10.1 | 0.66 | 0.6 | 3.4 | 41.7 | 6.7 | 0.6 | 0.3 | 28.2 | 90.7 | 31.0 |
| AK729 | 3 | 5.61 | 5.78 | 5.75 | 5.75 | 5.87 | 5.8 | 0.6 | 0.3 | 1.3 | 9.7 | 4.7 | 0.6 | 0.3 | 37.4 | 99.4 | 37.7 |
| AL210 | 3.3 | 4.68 | 4.63 | 4.85 | 5 |  | 4.8 | 0.65 | 0.4 | 3.3 | 54.4 | 5.0 | 0.7 | 0.3 | 126.0 | 92.7 | 136.0 |
| AL303 | 2.8 | 19.9 | 19.1 | 19.5 | 18.9 | 18.2 | 19.1 | 0.63 | 0.13 | 1.9 | 24.2 | 3.7 | 0.7 | 0.14 | 129.0 | 99.1 | 130.0 |
| AL389 | 5.2 | 7.53 | 7.96 | 8.23 | 7.75 | 6.49 | 7.6 | 0.63 | 0.3 | 5.3 | 78.7 | 6.3 | 0.8 | 0.4 | 223.0 | 95.5 | 234.0 |
|  |  |  |  |  |  | Mean | 9.6 | 0.6 | 0.3 | 3.1 | 40.8 | 5.4 | 0.7 | 0.4 | 106.1 | 96.3 | 110.4 |
|  |  |  |  |  |  | SD | 5.5 | 0.1 | 0.2 | 1.5 | 26.0 | 1.3 | 0.1 | 0.3 | 60.2 | 2.9 | 63.2 |
|  |  |  |  |  |  | N | 10 |  |  |  |  |  |  |  |  |  |  |

All publications and patent applications cited in this specification are herein incorporated by reference in their entireties as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

We claim:

1. A method of treating rheumatoid arthritis or multiple sclerosis in a patient, said method comprising the step of administering to said patient a monoclonal antibody or a fragment thereof that:
   a) specifically binds to NKG2A and does not specifically bind to NKG2C or NKG2E;
   b) comprises a human constant region that does not substantially bind human FcγIIIa receptor (CD16); and
   c) when bound to NKG2A on a human NK cell, causes said NK cell to lyse a target human cell bearing HLA-E on the target cell surface when said target cell comes into contact with said NK cell and the antibody heavy chain comprises amino acids 31 to 35 of SEQ ID NO:2 for CDR1, amino acids 50 to 66 of SEQ ID NO:2 for CDR2 and amino acids 99-108 of SEQ ID NO:2 for CDR3 and the light chain comprises amino acids 24-34 of SEQ ID NO:6 for CDR1, amino acids 50 to 56 of SEQ ID NO:6 for CDR2 and amino acids 89-95 of SEQ ID NO:6 for CDR3.

2. The method according to claim 1, comprising the additional step of administering to said patient a second therapeutic agent selected from: an immunosuppressant, a corticosteroid, a TNF inhibitor, an inhibitor of TGF-beta 1, a cytokine inhibitor, a hematopoietic growth factor, a pain reliever, or an anti-inflammatory agent, wherein said second therapeutic agent is administered either as a separate dosage form or as part of said composition.

3. The method according to claim 1, wherein said monoclonal antibody blocks binding of HLA-E to NKG2A.

4. The method according to claim 1, wherein the treated patient has rheumatoid arthritis.

5. The method according to claim 1, wherein the treated patient has multiple sclerosis.

* * * * *

UNITED STATES PATENT AND TRADEMARK OFFICE
CERTIFICATE OF CORRECTION

PATENT NO. : 10,160,810 B2
APPLICATION NO. : 14/594353
DATED : December 25, 2018
INVENTOR(S) : Alessandro Moretta et al.

It is certified that error appears in the above-identified patent and that said Letters Patent is hereby corrected as shown below:

In the Specification

Column 1,
Lines 9-10, "PCT/M2005/004013" should read --PCT/IB2005/004013--.

Column 3,
Line 11, "3 S9 purportedly" should read --3S9 purportedly--.

Column 4,
Line 62, "Fc gamma RITA" should read --Fc gamma RIIA--.

Column 25,
Line 46, "or F(ab)$_2$" should read --or F(ab')$_2$--.

Column 26,
Line 6, "1-3549" should read --I-3549--.

Column 36,
Line 33, "WET 293:33-41" should read --JPET 293:33-41--.

Column 57,
Line 12, "A3, All" should read --A3, A11--.
Line 58, "4-h [510]-release" should read --4-h [51Cr]-release--.

Column 58,
Line 16, "TP010" should read --TPO10--.

Signed and Sealed this
Twentieth Day of August, 2019

Andrei Iancu
*Director of the United States Patent and Trademark Office*

SEQUENCE LISTING

<160> NUMBER OF SEQ ID NOS: 8

<210> SEQ ID NO 1
<211> LENGTH: 396
<212> TYPE: DNA
<213> ORGANISM: Mus musculus
<220> FEATURE:
<221> NAME/KEY: CDS
<222> LOCATION: (1)..(372)

<400> SEQUENCE: 1

```
cag gtc caa ctg cag cag cct ggg gct gag ctg gtg agg cct ggg gct      48
Gln Val Gln Leu Gln Gln Pro Gly Ala Glu Leu Val Arg Pro Gly Ala
1               5                   10                  15 tca gtg aag ctg tcc tgc aag gct tct ggc tac acg ttc acc agc tac      96
Ser Val Lys Leu Ser Cys Lys Ala Ser Gly Tyr Thr Phe Thr Ser Tyr
            20                  25                  30 tgg atg aac tgg gtt aag cag agg cct gag caa ggc ctt cag tgg att     144
Trp Met Asn Trp Val Lys Gln Arg Pro Glu Gln Gly Leu Gln Trp Ile
        35                  40                  45 gga agg att gat cct tac gat agt gaa act cac tac agt caa aag ttc     192
Gly Arg Ile Asp Pro Tyr Asp Ser Glu Thr His Tyr Ser Gln Lys Phe
    50                  55                  60 aag gac aag gcc ata ttg act gta gac aaa tcc tcc agc aca gcc tac     240
Lys Asp Lys Ala Ile Leu Thr Val Asp Lys Ser Ser Ser Thr Ala Tyr
65                  70                  75                  80 atg cga ctc agc agc ctg aca tct gag gac tct gcg gtc tat tac tgt     288
Met Arg Leu Ser Ser Leu Thr Ser Glu Asp Ser Ala Val Tyr Tyr Cys
                85                  90                  95 gca aga ggg ggc tat gat ttc gac gta gga act ctc tac tgg ttc ttc     336
Ala Arg Gly Gly Tyr Asp Phe Asp Val Gly Thr Leu Tyr Trp Phe Phe
            100                 105                 110 gat gtc tgg ggc gca ggg acc acg gtc acc gtc tcc tcagcctcca          382
Asp Val Trp Gly Ala Gly Thr Thr Val Thr Val Ser
```

```
                                115                 120 ccaagggccc atcg                                                          396

<210> SEQ ID NO 2
<211> LENGTH: 124
<212> TYPE: PRT
<213> ORGANISM: Mus musculus

<400> SEQUENCE: 2

Gln Val Gln Leu Gln Gln Pro Gly Ala Glu Leu Val Arg Pro Gly Ala
1               5                   10                  15

Ser Val Lys Leu Ser Cys Lys Ala Ser Gly Tyr Thr Phe Thr Ser Tyr
            20                  25                  30

Trp Met Asn Trp Val Lys Gln Arg Pro Glu Gln Gly Leu Gln Trp Ile
        35                  40                  45

Gly Arg Ile Asp Pro Tyr Asp Ser Glu Thr His Tyr Ser Gln Lys Phe
    50                  55                  60

Lys Asp Lys Ala Ile Leu Thr Val Asp Lys Ser Ser Thr Ala Tyr
65                  70                  75                  80

Met Arg Leu Ser Ser Leu Thr Ser Glu Asp Ser Ala Val Tyr Tyr Cys
                85                  90                  95

Ala Arg Gly Gly Tyr Asp Phe Asp Val Gly Thr Leu Tyr Trp Phe Phe
            100                 105                 110

Asp Val Trp Gly Ala Gly Thr Thr Val Thr Val Ser
        115                 120

<210> SEQ ID NO 3
<211> LENGTH: 472
<212> TYPE: DNA
<213> ORGANISM: Artificial sequence
<220> FEATURE:
<223> OTHER INFORMATION: human heavy chain constant region
<220> FEATURE:
<221> NAME/KEY: CDS
<222> LOCATION: (2)..(448)

<400> SEQUENCE: 3 c gcc aag ctt gcc gcc acc atg gga tgg aac tat atc atc ctc ttc ttg    49
  Ala Lys Leu Ala Ala Thr Met Gly Trp Asn Tyr Ile Ile Leu Phe Leu
  1               5                   10                  15 tta gca aca gct aca tgt gtc cac tcc cag gtc caa ctg cag cag cct      97
Leu Ala Thr Ala Thr Cys Val His Ser Gln Val Gln Leu Gln Gln Pro
            20                  25                  30 ggg gct gag ctg gtg agg cct ggg gct tca gtg aag ctg tcc tgc aag     145
Gly Ala Glu Leu Val Arg Pro Gly Ala Ser Val Lys Leu Ser Cys Lys
        35                  40                  45 gct tct ggc tac acg ttc acc agc tac tgg atg aac tgg gtt aag cag    193
Ala Ser Gly Tyr Thr Phe Thr Ser Tyr Trp Met Asn Trp Val Lys Gln
    50                  55                  60 agg cct gag caa ggc ctt cag tgg att gga agg att gat cct tac gat    241
Arg Pro Glu Gln Gly Leu Gln Trp Ile Gly Arg Ile Asp Pro Tyr Asp
65                  70                  75                  80 agt gaa act cac tac agt caa aag ttc aag gac aag gcc ata ttg act    289
Ser Glu Thr His Tyr Ser Gln Lys Phe Lys Asp Lys Ala Ile Leu Thr
                85                  90                  95 gta gac aaa tcc tcc agc aca gcc tac atg cga ctc agc agc ctg aca    337
Val Asp Lys Ser Ser Ser Thr Ala Tyr Met Arg Leu Ser Ser Leu Thr
            100                 105                 110 tct gag gac tct gcg gtc tat tac tgt gca aga ggg ggc tat gat ttc    385
Ser Glu Asp Ser Ala Val Tyr Tyr Cys Ala Arg Gly Gly Tyr Asp Phe
```

```
            115                 120                 125
gac gta gga act ctc tac tgg ttc ttc gat gtc tgg ggc gca ggg acc       433
Asp Val Gly Thr Leu Tyr Trp Phe Phe Asp Val Trp Gly Ala Gly Thr
        130                 135                 140 acg gtc acc gtc tcc tcagcctcca ccaagggccc atcg                        472
Thr Val Thr Val Ser
145

<210> SEQ ID NO 4
<211> LENGTH: 149
<212> TYPE: PRT
<213> ORGANISM: Artificial sequence
<220> FEATURE:
<223> OTHER INFORMATION: human heavy chain constant region

<400> SEQUENCE: 4

Ala Lys Leu Ala Ala Thr Met Gly Trp Asn Tyr Ile Ile Leu Phe Leu
1               5                   10                  15

Leu Ala Thr Ala Thr Cys Val His Ser Gln Val Gln Leu Gln Gln Pro
            20                  25                  30

Gly Ala Glu Leu Val Arg Pro Gly Ala Ser Val Lys Leu Ser Cys Lys
        35                  40                  45

Ala Ser Gly Tyr Thr Phe Thr Ser Tyr Trp Met Asn Trp Val Lys Gln
    50                  55                  60

Arg Pro Glu Gln Gly Leu Gln Trp Ile Gly Arg Ile Asp Pro Tyr Asp
65                  70                  75                  80

Ser Glu Thr His Tyr Ser Gln Lys Phe Lys Asp Lys Ala Ile Leu Thr
                85                  90                  95

Val Asp Lys Ser Ser Ser Thr Ala Tyr Met Arg Leu Ser Ser Leu Thr
            100                 105                 110

Ser Glu Asp Ser Ala Val Tyr Tyr Cys Ala Arg Gly Gly Tyr Asp Phe
        115                 120                 125

Asp Val Gly Thr Leu Tyr Trp Phe Phe Asp Val Trp Gly Ala Gly Thr
    130                 135                 140

Thr Val Thr Val Ser
145

<210> SEQ ID NO 5
<211> LENGTH: 336
<212> TYPE: DNA
<213> ORGANISM: Mus musculus
<220> FEATURE:
<221> NAME/KEY: CDS
<222> LOCATION: (1)..(321)

<400> SEQUENCE: 5 gac atc cag atg act cag tct cca gcc tcc cta tct gca tct gtg gga       48
Asp Ile Gln Met Thr Gln Ser Pro Ala Ser Leu Ser Ala Ser Val Gly
1               5                   10                  15 gaa act gtc acc atc aca tgt cga gca agt gag aat att tac agt tat       96
Glu Thr Val Thr Ile Thr Cys Arg Ala Ser Glu Asn Ile Tyr Ser Tyr
            20                  25                  30 tta gca tgg tat cag cag aaa cag gga aaa tct cct cag ttc ttg gtc      144
Leu Ala Trp Tyr Gln Gln Lys Gln Gly Lys Ser Pro Gln Phe Leu Val
        35                  40                  45 tat aat gca aaa acc tta gca gaa ggt gtg cca tca agg ttc agt ggc      192
Tyr Asn Ala Lys Thr Leu Ala Glu Gly Val Pro Ser Arg Phe Ser Gly
    50                  55                  60 agt gga tca ggc aca cag ttt tct ctg aag atc aac agc ctg cag cct      240
Ser Gly Ser Gly Thr Gln Phe Ser Leu Lys Ile Asn Ser Leu Gln Pro
```

```
                          65                  70                  75                  80
gaa gat ttt ggg agt tat tac tgt caa cat cac tat ggt act cct cgg          288
Glu Asp Phe Gly Ser Tyr Tyr Cys Gln His His Tyr Gly Thr Pro Arg
                    85                  90                  95 acg ttc ggt gga ggc acc aag ctg gaa atc aaa cgtgagtgga tcccg            336
Thr Phe Gly Gly Gly Thr Lys Leu Glu Ile Lys
            100                 105

<210> SEQ ID NO 6
<211> LENGTH: 107
<212> TYPE: PRT
<213> ORGANISM: Mus musculus

<400> SEQUENCE: 6

Asp Ile Gln Met Thr Gln Ser Pro Ala Ser Leu Ser Ala Ser Val Gly
1               5                   10                  15

Glu Thr Val Thr Ile Thr Cys Arg Ala Ser Glu Asn Ile Tyr Ser Tyr
            20                  25                  30

Leu Ala Trp Tyr Gln Gln Lys Gln Gly Lys Ser Pro Gln Phe Leu Val
        35                  40                  45

Tyr Asn Ala Lys Thr Leu Ala Glu Gly Val Pro Ser Arg Phe Ser Gly
    50                  55                  60

Ser Gly Ser Gly Thr Gln Phe Ser Leu Lys Ile Asn Ser Leu Gln Pro
65                  70                  75                  80

Glu Asp Phe Gly Ser Tyr Tyr Cys Gln His His Tyr Gly Thr Pro Arg
                85                  90                  95

Thr Phe Gly Gly Gly Thr Lys Leu Glu Ile Lys
            100                 105

<210> SEQ ID NO 7
<211> LENGTH: 415
<212> TYPE: DNA
<213> ORGANISM: Artificial sequence
<220> FEATURE:
<223> OTHER INFORMATION: human light chain constant region
<220> FEATURE:
<221> NAME/KEY: CDS
<222> LOCATION: (2)..(400)

<400> SEQUENCE: 7 c gcc aag ctt gcc gcc acc atg agt gtg ctc act cag gtc ctg gcg ttg      49
  Ala Lys Leu Ala Ala Thr Met Ser Val Leu Thr Gln Val Leu Ala Leu
  1               5                   10                  15 ctg ctg ctg tgg ctt aca ggt gcc aga tgt gac atc cag atg tct cag        97
Leu Leu Leu Trp Leu Thr Gly Ala Arg Cys Asp Ile Gln Met Ser Gln
            20                  25                  30 act cca gcc tcc cta tct gca tct gtg gga gaa act gtc acc atc aca        145
Thr Pro Ala Ser Leu Ser Ala Ser Val Gly Glu Thr Val Thr Ile Thr
        35                  40                  45 tgt cga gca agt gag aat att tac agt tat tta gca tgg tat cag cag        193
Cys Arg Ala Ser Glu Asn Ile Tyr Ser Tyr Leu Ala Trp Tyr Gln Gln
    50                  55                  60 aaa cag gga aaa tct cct cag ttc ttg gtc tat aat gca aaa acc tta        241
Lys Gln Gly Lys Ser Pro Gln Phe Leu Val Tyr Asn Ala Lys Thr Leu
65                  70                  75                  80 gca gaa ggt gtg cca tca agg ttc agt ggc agt gga tca ggc aca cag        289
Ala Glu Gly Val Pro Ser Arg Phe Ser Gly Ser Gly Ser Gly Thr Gln
                85                  90                  95 ttt tct ctg aag atc aac agc ctg cag cct gaa gat ttt ggg agt tat        337
Phe Ser Leu Lys Ile Asn Ser Leu Gln Pro Glu Asp Phe Gly Ser Tyr
            100                 105                 110
```

```
tac tgt caa cat cac tat ggt act cct cgg acg ttc ggt gga ggc acc      385
Tyr Cys Gln His His Tyr Gly Thr Pro Arg Thr Phe Gly Gly Gly Thr
        115                 120                 125 aag ctg gaa atc aaa cgtgagtgga tcccg                                 415
Lys Leu Glu Ile Lys
    130

<210> SEQ ID NO 8
<211> LENGTH: 133
<212> TYPE: PRT
<213> ORGANISM: Artificial sequence
<220> FEATURE:
<223> OTHER INFORMATION: human light chain constant region

<400> SEQUENCE: 8

Ala Lys Leu Ala Ala Thr Met Ser Val Leu Thr Gln Val Leu Ala Leu
1               5                   10                  15

Leu Leu Leu Trp Leu Thr Gly Ala Arg Cys Asp Ile Gln Met Ser Gln
                20                  25                  30

Thr Pro Ala Ser Leu Ser Ala Ser Val Gly Glu Thr Val Thr Ile Thr
            35                  40                  45

Cys Arg Ala Ser Glu Asn Ile Tyr Ser Tyr Leu Ala Trp Tyr Gln Gln
50                  55                  60

Lys Gln Gly Lys Ser Pro Gln Phe Leu Val Tyr Asn Ala Lys Thr Leu
65                  70                  75                  80

Ala Glu Gly Val Pro Ser Arg Phe Ser Gly Ser Gly Ser Gly Thr Gln
                85                  90                  95

Phe Ser Leu Lys Ile Asn Ser Leu Gln Pro Glu Asp Phe Gly Ser Tyr
                100                 105                 110

Tyr Cys Gln His His Tyr Gly Thr Pro Arg Thr Phe Gly Gly Gly Thr
        115                 120                 125

Lys Leu Glu Ile Lys
    130
```